United States Patent [19]

Abdulla et al.

[11] Patent Number: 4,604,127

[45] Date of Patent: Aug. 5, 1986

[54] HERBICIDAL PYRIDAZINYLIMIDAZOLIDINONE COMPOUNDS

[75] Inventors: Riaz F. Abdulla, Greenfield; Jack G. Samaritoni, Knightstown, both of Ind.

[73] Assignee: Eli Lilly and Company, Indianapolis, Ind.

[21] Appl. No.: 734,365

[22] Filed: May 15, 1985

Related U.S. Application Data

[63] Continuation-in-part of Ser. No. 631,655, Jul. 17, 1984, abandoned.

[51] Int. Cl.$^4$ .................. A01N 43/58; C07D 237/20; C07D 237/22; C07D 237/12
[52] U.S. Cl. ........................................... 71/66; 71/92; 544/238; 544/239; 544/240; 544/241
[58] Field of Search ............... 544/238, 239, 240, 241; 71/92, 66

[56] References Cited

U.S. PATENT DOCUMENTS

| | | | |
|---|---|---|---|
| 3,542,798 | 11/1970 | Doebel et al. | 260/295 |
| 3,646,206 | 2/1972 | Doebel et al. | 424/263 |
| 3,723,455 | 3/1973 | Chupp | 260/309.6 |
| 3,990,883 | 11/1976 | Clapot et al. | 71/98 |
| 4,093,444 | 6/1978 | Clapot et al. | 71/92 |
| 4,099,955 | 7/1978 | Clapot et al. | 71/98 |
| 4,268,679 | 5/1981 | Lavanish | 548/247 |
| 4,314,844 | 2/1982 | Swithenbank | 71/92 |
| 4,331,807 | 5/1982 | Okamoto et al. | 544/224 |
| 4,397,678 | 8/1983 | Okamoto et al. | 71/72 |
| 4,399,137 | 8/1983 | Steiner | 424/250 |
| 4,474,962 | 10/1984 | Wepplo | 546/167 |
| 4,507,145 | 3/1985 | Lavanish | 71/92 |

FOREIGN PATENT DOCUMENTS

| | | |
|---|---|---|
| 52668 | 6/1982 | European Pat. Off. . |
| 91596 | 1/1983 | European Pat. Off. . |
| 93589 | 11/1983 | European Pat. Off. . |
| 52-031083 | 3/1977 | Japan . |
| 58-077866 | 5/1983 | Japan . |
| 2119252A | 11/1983 | United Kingdom . |

OTHER PUBLICATIONS

Crossland, I., *Acta. Chem. Scand.*, vol. 22, pp. 2700–2702, (1968).
Castle, R. ed., "Pyridazines", John Wiley & Sons, pp. 25, 245–248, (1973).
Ach, A., *Liebig's Ann. der Chemie*, vol. 253, pp. 44–57, (1889).
Horning et al., *J. Org. Chem.*, vol. 20, pp. 707–713, (1955).
Bianchi, M. et al., "Compounds with antiulcer and antisecretory activity. II, 3-Heteroaryl-benzimidazolin-2-ones *Eur. J. Med. Chem.-Chim. Ther.*, 18(6), 495–500, (1983).
Nagarajan, K. et al., "Nitroimidazoles: Part XIX. Structure Activity Relationships", *Indian J. Chem. Sect. B*, 23B(4), 342–362, (1984).
AbuOuf, A. et al., "Nitropyridine Derivatives, I. Synthesis of 1-(5-nitro-2-pyridyl)-2-imidazolidinone and imidazolidinethione", *Drug Res.*, 1(1), 183–188, (1968).
Nagarajan, K. et al., "Nitroimidazoles, Part IV, 1-Sulfonyl-(carbamoyl/thiocarbamoyl)-3-(1-methyl-5-nitroimidazol-2-yl)-2-imidazolidinones", *Indian J. Chem. Sect. B*, 21B(10), 928–940, (1982).

*Primary Examiner*—Donald G. Daus
*Assistant Examiner*—Stephen M. Kapner
*Attorney, Agent, or Firm*—Kathleen R. S. Page; Arthur R. Whale

[57] ABSTRACT

This invention describes novel pyridazinylimidazolidinone compounds, which are useful as herbicides.

39 Claims, No Drawings

HERBICIDAL PYRIDAZINYLIMIDAZOLIDINONE COMPOUNDS

This application is a continuation-in-part application of Ser. No. 631,655, filed July 17, 1984 now abandoned.

BACKGROUND OF THE INVENTION

This invention belongs to the field of agricultural chemistry and provides a class of new herbicidal compounds, herbicidal methods, and formulations making use of the compounds.

SUMMARY OF THE INVENTION

This invention provides pyridazinylimidazolidinone compounds of the formula (I):

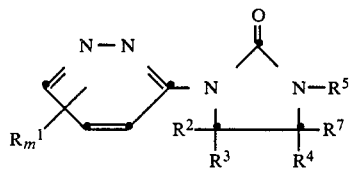

wherein $R^1$ is halo, $C_1$–$C_8$ alkyl, $C_1$–$C_6$ alkoxy, $C_2$–$C_6$ alkenyl, $C_2$–$C_6$ alkynyl, $C_3$–$C_6$ cycloalkyl, ($C_1$–$C_3$ alkyl)$C_3$–$C_6$ cycloalkyl, ($C_1$–$C_3$ alkoxy)$C_1$–$C_8$ alkyl, adamantyl, phenyl, halo-substituted phenyl, (phenyl)$C_1$–$C_8$ alkyl, phenoxy, or (phenoxy)$C_1$–$C_8$ alkyl;

$R^2$ is hydrogen, hydroxy, $C_1$–$C_6$ alkyl, $C_1$–$C_6$ alkoxy, or

wherein $R^6$ is $C_1$–$C_{15}$ alkyl, $C_2$–$C_{15}$ alkenyl, $C_2$–$C_{15}$ alkynyl, $C_3$–$C_6$ cycloalkyl, di($C_1$–$C_6$ alkyl)amino, di(phenyl)amino, naphthyl, ($C_1$–$C_6$ alkyl)(phenyl)amino, or

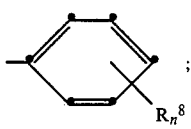

wherein $R^8$ is halo, $C_1$–$C_6$ alkyl, $C_1$–$C_6$ alkoxy, halo($C_1$–$C_6$ alkyl), cyano, nitro, acetyl, phenyl, benzoyl, phenoxy, phenylthio, ($C_1$–$C_6$ alkyl)thio, $CF_3O$, $CF_3S$, or carboxy, optionally esterified with $C_1$–$C_6$ alkanol;

$R^3$ is hydrogen or $C_1$–$C_6$ alkyl;

$R^4$ is hydrogen, hydroxy, $C_1$–$C_6$ alkyl, or

or $R^3$ and $R^4$ together form a double bond;

$R^5$ is hydrogen, $C_1$–$C_6$ alkyl, $C_1$–$C_6$ alkoxy, or benzyl;

$R^7$ is hydrogen or $C_1$–$C_6$ alkyl; and m and n are independently integers from 0 to 3.

Also provided by this invention are methods of use for these compounds as herbicides. Further provided are formulations comprising the pyridazinylimidazolidinone compounds and agriculturally-acceptable carriers therefor.

DETAILED DESCRIPTION OF THE INVENTION

In addition to the compounds of formula (I), there is also provided a preferred group of compounds wherein:

$R^1$ is halo or $C_1$–$C_6$ alkyl;

$R^2$ is hydrogen, hydroxy, $C_1$–$C_4$ alkyl, $C_1$–$C_4$ alkoxy, or

wherein $R^6$ is $C_1$–$C_6$ alkyl or

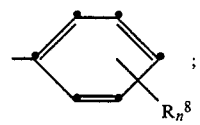

$R^8$ is halo, methyl, or methoxy;

$R^3$ is hydrogen or $C_1$–$C_3$ alkyl;

$R^4$ is hydrogen, hydroxy, or $C_1$–$C_3$ alkyl;

or $R^3$ and $R^4$ together form a double bond;

$R^5$ is hydrogen or $C_1$–$C_3$ alkyl;

$R^7$ is hydrogen; and m and n are independently 1 or 2.

These compounds include:

3-[6-chloro-5-(1,1-dimethylbutyl)-3-pyridazinyl]-4-hydroxy-1-methyl-2-imidazolidinone;

3-[6-chloro-5-(1,1-dimethylethyl)-3-pyridazinyl]-1-methyl-4-(1-oxopropoxy)-2-imidazolidinone;

2-methylpropanoic acid, 3-[6-chloro-5-(1,1-dimethylethyl)-3-pyridazinyl]-1-methyl-2-oxo-4-imidazolidinyl ester; and 2,2-dimethylpropanoic acid, 3-[6-chloro-5-(1,1-dimethylethyl)-3-pyridazinyl]-1-methyl-2-oxo-4-imidazolidinyl ester.

A more preferred group of compounds include those wherein:

$R^1$ is chloro or 1,1-dimethylethyl;

$R^2$ is hydroxy or

wherein $R^6$ is

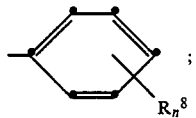

$R^8$ is halo or methoxy;

$R^3$ and $R^4$ are hydrogen; and $R^5$ is methyl.

Some of the most preferred compounds include:

3-[6-chloro-5-(1,1-dimethylethyl)-3-pyridazinyl]-4-hydroxy-1-methyl-2-imidazolidinone;

3-[6-(1,1-dimethylethyl)-3-pyridazinyl]-4-hydroxy-1-methyl-2-imidazolidinone;

3-[5-(1,1-dimethylethyl)-3-pyridazinyl]-4-hydroxy-1-methyl-2-imidazolidinone;

4-chlorobenzoic acid, 3-[6-chloro-5-(1,1-dimethylethyl)-3-pyridazinyl]-1-methyl-2-oxo-4-imidazolidinyl ester; and 4-methoxybenzoic acid, 3-[6-chloro-5-(1,1-dimethylethyl)-3-pyridazinyl]-1-methyl-2-oxo-4-imidazolidinyl ester.

The following defines the various terms used in this application.

The term "$C_1$–$C_{15}$ alkyl" refers to the straight and branched aliphatic groups of one to fifteen carbon atoms including ethyl, propyl, isopropyl (1-methylethyl), butyl, methyl, isobutyl (2-methylpropyl), sec-butyl (1-methylpropyl), tert-butyl (1,1-dimethylethyl), pentyl, isopentyl (3-methylbutyl), sec-pentyl (1-methylbutyl), 1,1-dimethylpropyl, 1,2-dimethylpropyl, neopentyl (2,2-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, undecyl, dodecyl, tridecyl, neopentyl, 1-methylbutyl, 2-ethylbutyl, 3-methylbutyl, 4-methylhexyl, 2,2-diethylpentyl, 3-propylhexyl, 1,3-diethylpentyl, 2-methyloctyl, 3-propyloctyl, 4-ethylheptyl, 2-butylheptyl, 3-methyldecyl, 1-ethylundecyl, 2,4-diethylnonyl, 1-pentylhexyl, 5-propyldecyl and the like. The terms "$C_1$–$C_8$ alkyl", "$C_1$–$C_6$ alkyl", "$C_1$–$C_4$ alkyl", and "$C_1$–$C_3$ alkyl" are also included in this definition.

The term "$C_1$–$C_6$ alkoxy" refers to the aliphatic groups of one to six carbon atoms attached to the remainder of the molecule by an oxygen atom, such as methoxy, ethoxy, propoxy, butoxy, and the like. The terms "$C_1$–$C_4$ alkoxy" and "$C_1$–$C_3$ alkoxy" are also included in this definition.

The halogens include bromine, chlorine, fluorine, and iodine.

The term "$C_3$–$C_6$ cycloalkyl" refers to saturated aliphatic rings of three to six carbon atoms, such as cyclopropyl, cyclobutyl, cyclopentyl, and cyclohexyl.

The term "$C_2$–$C_{15}$ alkenyl" refers to straight and branched unsaturated aliphatic groups of two to fifteen carbon atoms, wherein one carbon to carbon double bond exists in the group, and includes ethenyl, propenyl, 1-butenyl, 2-butenyl, 2-methylpropenyl, 1-pentenyl, 2-pentenyl, 3-pentenyl, 3-methyl-1-butenyl, 2-methyl-2-butenyl, 1-hexenyl, 2-hexenyl, 3-hexenyl, 2,3-dimethyl-2-butenyl, 4-heptenyl, 3-octenyl, 5-decenyl, and the like. The term "$C_2$–$C_6$ alkenyl" is also included in this definition.

The term "$C_2$–$C_{15}$ alkynyl" refers to straight and branched unsaturated aliphatic groups of two to fifteen carbon atoms, wherein one carbon to carbon triple bond exists in the group, and includes ethynyl, propynyl, 1-butynyl, 2-butynyl, 1-pentynyl, 2-pentynyl, 3-methyl-1-butynyl, 1-hexynyl, 2-hexynyl, 3,3-dimethyl-1-butynyl, 3-hexynyl, 1-heptynyl, 1-octynyl, 4-octynyl, 1-nonynyl, 1-decynyl, 5-decynyl, and the like. The term "$C_2$–$C_6$ alkynyl" is also included in this definition.

The term "di($C_1$–$C_6$ alkyl)amino" refers to two like or unlike alkyl groups of one to six carbon atoms long attached to the remainder of the molecule through an amine group, and includes dimethylamino, diethylamino, and the like.

The term "halo($C_1$–$C_6$ alkyl)" refers to an alkyl group, which is substituted by one to three halogen atoms, such as trifluoromethyl, and the like.

The term "($C_1$–$C_3$ alkyl)$C_3$–$C_6$ cycloalkyl" refers to an alkyl group of one to three carbon atoms long attached to the remainder of the molecule through a cycloalkyl group of three to six carbon atoms.

The term ($C_1$–$C_3$ alkoxy)$C_1$–$C_8$ alkyl" refers to an alkoxy group of one to three carbon atoms long attached to the remainder of the molecule through an alkyl group of one to eight carbon atoms.

The term "halo-substituted phenyl" refers to a phenyl group, which is substituted by one to three halogen atoms.

The term "(phenyl)$C_1$–$C_8$ alkyl" refers to a phenyl group attached to the remainder of the molecule through an alkyl group of one to eight carbon atoms.

The term "(phenoxy)$C_1$–$C_8$ alkyl" refers to a phenoxy group attached to the remainder of the molecule through an alkyl group of one to eight carbon atoms.

The term "di(phenyl)amino" refers to two phenyl groups attached to the remainder of the molecule through an amine group.

The term "($C_1$–$C_6$ alkyl)(phenyl)amino" refers to an alkyl group of one to six atoms long and a phenyl group both attached to the remainder of the molecule through an amine group.

The term "($C_1$–$C_6$ alkyl)thio" refers to an alkyl group of one to six carbons attached to the remainder of the molecule through a sulfur atom.

The term "$C_1$–$C_6$ alkanol" refers to an alcohol of one to six carbon atoms.

PREPARATION OF THE COMPOUNDS OF FORMULA (I)

The processes for making the pyridazinylimidazolidinone compounds of formula (I) are outlined below.

Preparation 1

Most of the pyridazinylimidazolidinone compounds provided by this invention are prepared by cyclization of a suitably substituted pyridazinylurea of the formula:

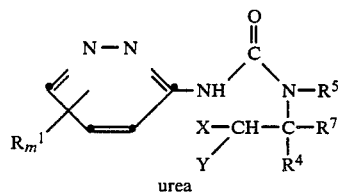

urea wherein $R^1$, $R^4$, $R^5$, $R^7$, and m are as defined above, and X and Y are $C_1$–$C_6$ alkoxy, such as methoxy, ethoxy, propoxy, and the like.

The cyclization of the urea intermediate can be accomplished by simply heating the intermediate in the presence of an acid. Commonly used acids include mineral acids, such as hydrochloric, hydrobromic, sulfuric, phosphoric, nitric, and related acids. Organic acids, such as acetic acid, can also be utilized if desired. The amount of acid commonly employed to effect the cyclization is about an equimolar amount or an excess, and routinely the reaction is simply carried out in a dilute aqueous acid solution having an acid concentration of about 0.5 to about 5 percent by weight. If desired, the cyclization reaction can be carried out in a solvent medium other than water, such as dioxane, dimethylsulfoxide (DMSO), dimethylformamide (DMF), and the like, with an equimolar or excess amount of suitable acid added. The cyclization reaction generally is substantially complete within about 10 to about 90 minutes when carried out at an elevated temperature of about 40° to about 100° C. The reaction provides a pyridazinylimidazolidinone, which is readily isolated by cooling the reaction mixture, for instance to 0° to about 5° C., and then collecting the precipitate. The precipitated pyridazinylimidazolidinone can be further purified, if desired, by conventional means, including chromatography and crystallization from common solvents, such as ethanol, acetone, dioxane, water, and the like.

Preparation 2

The compounds of formula (I) can also be prepared by cyclization of a pyridazinylurea of the formula:

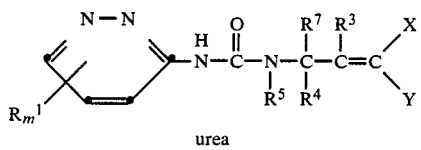

urea using ozonation, followed by reduction. This reaction can be carried out by oxidizing the urea starting compound with ozone. Ozone may be supplied to the reaction in the usual way, diluted with air as it is formed in typical ozonators. It has been found that no particular excess of ozone is necessary, if the air-ozone mixture is efficiently dispersed in the reaction mixture with good agitation. Chemists usually monitor reactions in which ozone is used by testing the off-gas from the reactor with an indicator, such as starch/iodine paper, and adjusting the addition rate of the ozone to minimize wasting it. (The reaction can also be monitored by the use of dyes.) Completion of the reaction is easily observed in the same way, because it is signaled by a sudden increase in the concentration of ozone leaving the reactor.

No particular precautions need be observed in the ozone reaction, except that reaction mixtures have often been observed to foam vigorously as the reaction proceeds. Adequate head space in the reactor must be allowed to accommodate foaming; small amounts of antifoam materials, such as silicone, may be used.

After the oxidation with ozone is complete, a sufficient amount of reducing agent is added to reduce residual ozone dissolved in the mixture, and to reduce the oxidized intermediate itself. In general, from about 1.1 to about 2.0 equivalents of reducing agent should be added per mole of starting compound. The usual types of reducing agents are used for the reduction. It is unnecessary to use catalytic or electrolytic reduction; inexpensive reducing agents, such as $C_1$-$C_4$ dialkyl sulfides, thiosulfate salts, sulfite salts, hydrosulfite salts, phosphite salts, alkali metal iodides, sulfur dioxide, stannous chloride, zinc or magnesium metal, formaldehyde, and the like, are entirely satifactory. Dialkyl sulfides, especially dimethyl sulfide, are most preferred.

The process is carried out in an organic solvent, which is inert to the oxidizing and reducing agents. Solvents, such as halogenated alkanes, lower alkanols, alkyl ketones, aromatics, esters, and the like, may be used as is convenient in the circumstances. It is preferred to use a water-immiscible solvent, or a substantial amount (at least enough to dissolve the product) of a water-immiscible solvent, if a solvent mixture is used, to facilitate isolation of the product. Relatively minor amounts of lower alkanoic acids or water may also be used in the mixture. Useful specific solvents include, for example, dichloromethane (methylene chloride), 1,2-dichloroethane, methanol, isopropanol, methyl ethyl ketone, methyl isobutyl ketone, diisopropyl ketone, ethyl acetate, 1,1,2-trichloroethane, benzene, toluene, propyl butyrate, ethylbenzene, and the like. Particularly preferred solvents are mixtures of halogenated alkanes and alkanols, especially dichloromethane/methanol mixtures.

Both the oxidation and reduction steps are preferably carried out in the same solvent, by merely adding the reducing agent to the mixture.

The oxidation step is preferably carried out at a relatively low temperature, in the range of from about $-100°$ to about $-50°$ C. Good results are obtained, however at temperatures in the broad range from about $-100°$ C. to about the ambient temperature. It is not necessary to use a reduced temperature during the reduction step, however, and the mixture may be allowed to warm to ambient, or even to be moderately heated in the range from about the ambient temperature to about 90° C., while the reducing agent is added and the reduction is carried out.

Both steps of the process are quite rapid. The speed of the oxidation step is apparently limited only by the speed with which the ozone can be dispersed and dissolved in the reaction mixture.

Preparation 3

The compounds of this invention can also be prepared by condensation of a halopyridazine and an imidazolidinone.

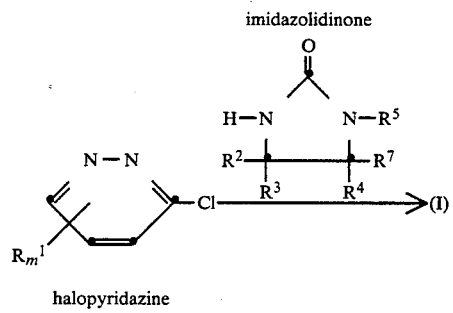

halopyridazine

Commonly a base is used to ensure deprotonation of the imidazolidinone, such a base includes sodium hydride. The reaction is carried out in an inert solvent, such as tetrahydrofuran (THF), DMF, toluene, and the like at temperatures from 25° to 100° C. for about ½ to 24 hours. Upon completion of the reaction, dilute hydrochloric acid or water is added and the organic phase is dried and concentrated. The resulting material can be purified by recrystallization or chromatography.

Preparation 4

Pyridazinylimidazolidinones wherein $R^2$ and $R^4$ are hydroxy can be prepared by reacting a pyridazinylurea with glyoxal to form the pyridazinyl-4,5-dihydroxyimidazolidinone. Typically, the glyoxal is in the form of an aqueous solution, which has been adjusted to a pH of between 7 and 8 with a suitable inorganic base, such as sodium hydroxide, potassium hydroxide, and the like. The reaction of the urea and glyoxal is carried at temperatures from 15° to 80° C., preferably from 20° to 40° C., for a period of 10 to 24 hours, preferably for about 18 hours. In addition, an inert organic solvent, such as THF, ethanol, and the like, is used.

The pyridazinylimidazolidinones thus described are useful not only as herbicides, but also as intermediates in the synthesis of other imidazolidinones of this invention.

Preparation 5

The pyridazinyl-4-hydroxyimidazolidinones are useful in the preparation of those imidazolidinones of the above general formula wherein $R^2$ is

For example, the pyridazinyl-4-hydroxyimidazolidinones of the invention are readily acylated with an acylating agent such as an acid halide. Commonly used acylating agents include acetyl chloride, butyryl iodide, hexanoyl bromide, and the like. Other acylating agents commonly employed include anhydrides, such as acetic anhydride, acetic formic anhydride, propanoic formic anhydride, and the like.

The acylation of a pyridazinyl-4-hydroxyimidazolidinone can be accomplished by reacting about equimolar quantities of a 4-hydroxyimidazolidinone and the acylating agent. An excess of the acylating agent can be employed if desired. Sodium hydride is added to the reaction in order to generate the corresponding alkoxide.

The reaction typically is conducted in a solvent, such as benzene, acetone, THF, dichloromethane, chloroform, or the like. The acylation reaction is generally subtantially complete after about 2 to about 24 hours when carried out at a temperature of about −20° to about 80° C. The acylated product can be isolated by simply removing the reaction solvent, for instance, by evaporation under reduced pressure. The acylated imidazolidinone can be purified, if needed, by conventional means, including washing with dilute acid and dilute base, chromatography, crystallization, and the like.

Preparation 6

The unsaturated imidazolinones or imidazolones of the invention, i.e. compounds of the above formula wherein $R^3$ and $R^4$ together form a double bond, are preferably prepared by dehydrating a hydroxyimidazolidinone according to the following sequence:

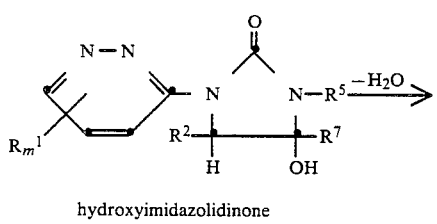

hydroxyimidazolidinone

-continued

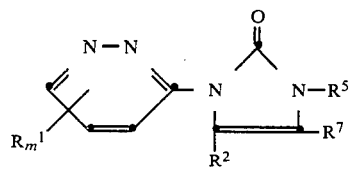

imidazolone

Such dehydration can be effected by reacting the hydroxyimidazolidinone with an acid, such as a mineral acid, or preferably with an equimolar amount or slight excess of a halogenating agent, such as thionyl chloride. For example, reaction of a 5-hydroxyimidazolidinone with about an equimolar amount of thionyl chloride in a solvent, such as chloroform or methylene chloride, for about 1 to about 24 hours at a temperature of about 0° to about 50° C. provides the corresponding imidazolone or unsaturated imidazolinone. The product can be recovered by simply removing the reaction solvent, for instance by evaporation, and further purification can be achieved, if desired, by routine procedures, such as crystallization from common solvents like acetone or diethyl ether.

Preparation 7

Halide groups on the pyridazine ring of the compounds of this invention can be removed to form the unsubstituted pyridazine by a slight pressure of hydrogen gas in the presence of a metal catalyst, such as platinum, palladium on carbon, and Raney nickel.

Preparation 8

The compounds of this invention wherein $R^2$ is hydroxy can also be prepared from the corresponding ketone. The ketone is reduced either by catalytic hydrogenation or by use of chemical reducing agents, such as lithium aluminum hydride, sodium borohydride, and the like. If a metal hydride is used, then a mineral acid, such as sulfuric acid, is used to form the hydroxy or alcohol group.

Preparation of Intermediates

Pyridazinylurea intermediates can be prepared by any of several procedures. In a typical procedure, a substituted pyridazine is reacted with a haloformate, such as phenyl chloroformate, to give an pyridazinyl carbamate, which when reacted with a suitably substituted ethylamine gives the pyridazinylurea. Such procedure can be illustrated by the following sequence:

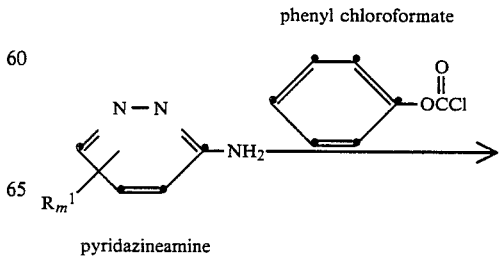

pyridazineamine

-continued

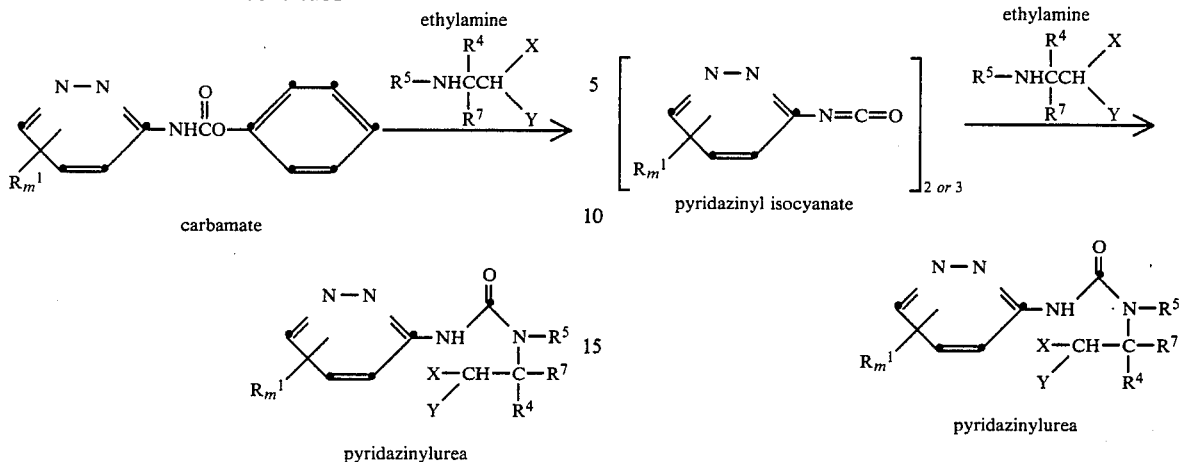

carbamate pyridazinyl isocyanate pyridazinylurea pyridazinylurea

The ethylamines of the formula $R^5NHC(R^4)(R^7)CHXY$ are well known in the art and some are commercially available.

The reaction of a haloformate, such as phenyl chloroformate, and a pyridazineamine generally is carried out by combining a slight excess of haloformate with the pyridazine in an organic solvent, such as pyridine or triethylamine, and stirring the mixture for about 1 to about 24 hours at a temperature of about 0° to about 30° C. The product of the reaction, a pyridazinyl carbamate, is generally isolated by acidifying the reaction mixture, for instance by the addition of a mineral acid, such as hydrochloric acid or sulfuric acid, and collecting by filtration the precipitate which forms. The carbamate normally needs no further purification, but if desired it can be crystallized from common solvents, such as benzene, acetone, ethyl acetate, and the like.

The carbamate and the ethylamine generally are combined in a mutual organic solvent, such as toluene, benzene, and THF. The reactants can be utilized in about equimolar amounts, or if desired the ethylamine derivative can be employed in excess. The reaction routinely is substantially complete within about 2 to about 5 hours when carried out at a temperature of about 50° to about 100° C. Isolation of the product, a pyridazinylurea intermediate, usually is accomplished by simply removing the reaction solvent, for instance, by evaporation under reduced pressure. The urea can be further purified, if needed, by routine methods, including crystallization and chromatography.

An alternative procedure for preparing the intermediates of the invention comprises reacting a suitably substituted ethylamine with a pyridazinyl isocyanate. The isocyanate is conveniently prepared by reacting a pyridazine with phosgene in the presence of an acid, such as hydrochloric acid, to give the corresponding pyridazinylcarbamoyl chloride. The latter compound undergoes dehydrohalogenation in situ to provide the corresponding pyridazinyl isocyanate. (The isocyanate is formed as the dimer or trimer). The reaction of the isocyanate with an ethylamine derivative is illustrated by the following sequence:

The reaction of an ethylamine with a pyridazinyl isocyanate generally is carried out by combining approximately equimolar quantities of the reactants in a suitable solvent, such as benzene, toluene, or THF. The reaction normally is complete within about 2 to about 5 hours when carried out at a temperature of about 50° to about 100° C. Isolation of the product generally is achieved by simply removing the reaction solvent by evaporation under reduced pressure. Further purification, if needed, can be accomplished by crystallization, chromatography, or similar conventional methods.

The halopyridazine intermediate can be prepared by the reaction of a less substituted pyridazine with a carboxylic acid in the presence of peroxydisulfate ion, a catalytic amount of silver ion, and mineral acid, whose anion will not cause precipitation of the corresponding silver salt, all in an aqueous solvent system at a temperature from about 40° to about 80° C.

A pyridazine is reacted with a carboxylic acid. Silver (II) ion, generated from silver (I) ion and peroxydisulfate, is used in the oxidative decarboxylation of the carboxylic acid. The reaction is carried out in an aqueous solvent system with a mineral acid at a temperature from about 40° to about 80° C.

The silver ion is obtained from a water-soluble silver (I) salt, such as silver nitrate, silver fluoride, silver trifluoroacetate, silver perchlorate, and the like, with silver nitrate being preferred. The silver (I) salt is used in catalytic amounts in the reaction, but the actual catalyst generated is silver (II) ion.

Typical of the carboxylic acids are pivalic acid (trimethylacetic acid), n-butyric acid, isobutyric acid, propanoic acid, acetic acid, cyclobutanecarboxylic acid, cyclopropanecarboxylic acid, cyclopentanecarboxylic acid, 1-adamantanecarboxylic acid, phenoxyacetic acid, glycolic acid, and the like, with pivalic acid being preferred. The source of peroxydisulfate (persulfate) ion is an ammonium peroxydisulfate or an alkali peroxydisulfate. Ammonium peroxydisulfate is preferred.

Typical of the aqueous solvent systems which can be used are water, water-acetonitrile, and the like with water being preferred. The mineral acids that can be used must be those whose anion will not cause precipitation of the corresponding silver salt. Such mineral acids include perchloric, trifluoroacetic, sulfuric, and the like with sulfuric being preferred.

The reaction goes rapidly, and no unusual excess of reagents is necessary. In general, stoichiometric amounts of the reagents are adequate. As is usual in organic chemistry, it may be economical to use an excess of less expensive reagents to assure that more expensive reagents are fully consumed.

The amount of reactants used varies with the particular reactants, but typically 0.05 to 1.0 equivalent of silver ion; 1.0 to 5.0 equivalents of carboxylic acid; 1.0 to 3.0 equivalents of mineral acid; and 1.0 to 2.0 equivalents of peroxydisulfate ion are used with respect to the pyridazine. The preferred amounts used are 0.1 equivalent of silver and 1.0 to 1.75 equivalents of peroxydisulfate. The amounts of reactants used also vary with the desired amount of alkylation. In the case of dialkylation, the amount of peroxydisulfate, silver, and carboxylic acid used can be increased.

Usually the pyridazine starting material, silver salt, carboxylic acid, and mineral acid are all in an aqueous solvent system and heated to about 40° to 80° C. Maintaining the temperature, a solution of peroxydisulfate in water is added dropwise. The reaction is well stirred and heating is continued for about 1 to 2 hours. After cooling the mixture with ice-water, it is made basic in order to facilitate isolation of the product.

Preferably, the reaction is heated to about 50° C. and then the peroxydisulfate is added. The addition of the peroxydisulfate must be at a rate sufficient to control the exotherm of the reaction. In order to maximize the yield of product, the temperature of the reaction must be maintained below 80° C. Once the addition of peroxydisulfate is complete, the reaction is stirred or agitated for about 10 minutes to 1 hour at a temperature from 70° to 80° C. It is important to keep the reaction mixture well agitated. Therefore, it is advisable to use an air-driven stirrer and Morton flask for the reaction.

The products of this process are most easily isolated by using a base, such as ammonium hydroxide, sodium hydroxide, sodium carbonate, potassium carbonate, and the like, which make the reaction solution basic. The products are then extracted with an inert organic solvent, such as methylene chloride, and the like, and dried with magnesium sulfate, sodium sulfate, and the like. The concentrated solutions are then chromatographed, if necessary, over silica gel with eluting solvents composed of mixtures of alkanes and ethers, such as hexanes and ethyl ether.

Certain substituted pyridazines, such as 3-halo-6-alkylpyridazines, can be prepared by established routes starting with γ-ketoacids. The ketoacid is reacted with hydrazine by heating in a solvent. This reaction results in the cyclization and the formation of a substituted dihydropyridazinone. The dihydropyridazinone compound is then oxidized to form pyridazinone, using a reagent, such as bromine, in a solvent, such as acetic acid. Halogenation of the pyridazinone using, for example, phosphorus oxychloride forms the desired substituted pyridazine.

Alkoxy or aryloxy derivatives can be prepared from the reaction of the alkali metal salt of the corresponding alcohol or phenol with a pyridazine, such as 3,6-dichloropyridazine. This reaction is conducted in a solvent, such as the corresponding alcohol, DMF, DMSO, and the like. The salt used in the reaction can be preformed, for example, by the reaction of the alcohol and sodium hydride, or can be generated in situ. Typically, the temperature of the reaction is from room temperature to about the reflux temperature of the solvent.

Pyridazineamines can be prepared from the corresponding chloro derivative by reacting the derivative with ammonia under suitable conditions.

The following examples are illustrative of this invention. However, these examples are not to be construed as limitations on the invention. The temperatures are reported in degrees Celsius.

EXAMPLE 1

3-[6-Chloro-5-(1,1-dimethylethyl)-3-pyridazinyl]-4-hydroxy-1-methyl-2-imidazolidinone One hundred milliliters (ml) of 0.5N hydrochloric acid was added to 2.76 grams (g) (0.00302 mole) of N'-[6-chloro-5-(1,1-dimethylethyl)-3-pyridazinyl]-N-methyl-N-[2,2-(dimethoxy)ethyl]urea. The reaction mixture was heated to 55° for about 45 minutes. After cooling to 20°, a precipitate was collected and chromatographed on silica gel, using a 90/10 ratio of chloroform and ether as the eluent.

The material collected was recrystallized from a mixture of acetone and hexanes to give 1.1 g (46%) of a product with a melting point (MP) of 147°–149°. The molecular weight (MW) was 284.75. Nuclear magnetic resonance (NMR), infrared (IR), and mass spectra were consistent with the structure of the desired product.

The following elemental analysis was obtained:

Calculated for $C_{12}H_{17}ClN_4O_2$: Theory: C, 50.62; H, 6.02; N, 19.68; O, 11.24; Cl, 12.45; Found: C, 50.65; H, 6.14; N, 19.64; O, 11.54; Cl, 12.38.

The following examples were prepared using the general procedure of Example 1.

EXAMPLE 2

3-[6-Chloro-5-(1,1-dimethylbutyl)-3-pyridazinyl]-4-hydroxy-1-methyl-2-imidazolidinone Yield = 0.42 g (61%)
MP = 132°–137°
NMR, IR, and mass spectra were consistent with the structure of the desired product.
MW = 312.80
Calculated for $C_{14}H_{21}ClN_4O_2$: Theory: C, 53.76; H, 6.77; N, 17.91; Found: C, 54.67; H, 7.13; N, 17.22.

EXAMPLE 3

1-(6-Chloro-4,5-dimethyl-3-pyridazinyl)-1,3-dihydro-3-methyl-2H-imidazol-2-one

Yield = 0.7 g (89%)
NMR and mass spectra were consistent with the structure of the desired product.
Calculated for $C_{10}H_{11}ClN_4O$: Theory: C, 50.32; H, 4.65; N, 23.47; Found: C, 50.19; H, 4.65; N, 23.36.

EXAMPLE 4

3-[6-Chloro-5-(1,1-dimethylethyl)-3-pyridazinyl]-4-hydroxy-1-(phenylmethyl)-2-imidazolidinone Yield = 0.88 g (33%)
MP = 116°–121°
NMR and mass spectra were consistent with the structure of the desired product.
MW = 360.84
Calculated for $C_{18}H_{22}ClN_4O_2$: Theory: C, 59.91; H, 5.87; N, 15.53; Found: C, 60.12; H, 5.87; N, 15.74.

EXAMPLE 5

3-[6-(1,1-Dimethylethyl)-3-pyridazinyl]-4-hydroxy-1-methyl-2-imidazolidinone

Yield=1.8 g (77%)
MP=163°-166°
NMR, IR, and mass spectra were consistent with the structure of the desired product.
MW=250.29
Calculated for $C_{12}H_{18}N_4O_2$: Theory: C, 57.58; H, 7.25; N, 22.38; O, 12.78; Found: C, 57.82; H, 7.47; N, 22.34; O, 13.09.

EXAMPLE 6

3-(6-Chloro-3-pyridazinyl)-4-hydroxy-1-methyl-2-imidazolidinone

Yield=0.3 g (65%)
MP=163°-165.5°
NMR, IR, and mass spectra were consistent with the structure of the desired product.
MW=228.64
Calculated for $C_8H_9ClN_4O_2$: Theory: C, 42.01; H, 3.94; N, 24.51; O, 14.00; Cl, 15.54; Found: C, 42.18; H, 4.15; N, 24.24; O, 13.77; Cl, 15.67.

EXAMPLE 7

3-[6-Chloro-5-(1,1-dimethylethyl)-3-pyridazinyl]-4-hydroxy-1-methoxy-2-imidazolidinone To a solution of 3.82 g (0.0728 mole) of N'-[6-chloro-5-(1,1-dimethylethyl)-3-pyridazinyl]-N-methoxy-N-(2-propenyl)urea in 50 ml of methylene chloride and 10 ml of methanol was added a trace of Sudan III (pH indicator). Using a dry ice-acetone bath, the solution was lowered to a temperature of about −60° and ozone was bubbled in through a fritted glass tube.

After about 20-30 minutes, when the indicator was colorless, air was bubbled in to remove any dissolved ozone and then 1.2 ml (1.03 g, 0.0166 mole, 1.30 equivalents) of methyl sulfide was added. The solution was allowed to warm to near room temperature and was diluted to 400 ml with methylene chloride. After washing with three 30-ml portions of water, the solution was dried with magnesium sulfate.

The solution was concentrated, affording an oil, which was triturated under hexane to give 3.0 g of an off-white powder. The powder was recrystallized from a mixture of hexane and benzene to afford a product weighing 1.7 g (44%) with a melting point of 125°-128°. The molecular weight was 300.75 and NMR and mass spectra were consistent with the structure of the desired product.

The following elemental analysis was obtained:
Calculated for $C_{12}H_{17}ClN_4O_3$: Theory: C, 47.93; H, 5.70; N, 18.63; Found: C, 48.20; H, 5.73; N, 18.50.

The following examples were prepared using the general procedure of Example 7.

EXAMPLE 8

3-[6-Chloro-5-(1,1-dimethylethyl)-3-pyridazinyl]-1,5-dimethyl-4-hydroxy-2-imidazolidinone Yield=1.23 g (47%)
MP=124°-126°
NMR and mass spectra were consistent with the structure of the desired product.
MW=298.77
Calculated for $C_{13}H_{19}ClN_4O_2$: Theory: C, 52.26; H, 6.41; N, 18.75; Found: C, 52.35; H, 6.22; N, 18.64.

EXAMPLE 9

3-[6-Chloro-5-(1,1-dimethylethyl)-3-pyridazinyl]-4-hydroxy-1,4-dimethyl-2-imidazolidinone Yield=0.57 g (23%)
MP=112°-116°
NMR, IR and mass spectra were consistent with the structure of the desired product.
MW=298.77
Calculated for $C_{13}H_{19}ClN_4O_2$: Theory: C, 52.26; H, 6.41; N, 18.75; Found: C, 52.54; H, 6.19; N, 18.73.

EXAMPLE 10

3-[6-Chloro-5-(1,1-dimethylethyl)-3-pyridazinyl]-1,3-dihydro-1,4-dimethyl-2H-imidazol-2-one Yield=0.56 g (24%)
MP=188°-190°
NMR and mass spectra were consistent with the structure of the desired product.
Calculated for $C_{13}H_{17}ClN_4O$: Theory: C, 55.62; H, 6.10; N, 19.96; Found: C, 55.54; H, 5.84; N, 19.75.

EXAMPLE 11

1-[6-Chloro-5-(1,1-dimethylethyl)-3-pyridazinyl]-5-hydroxy-2-imidazolidinone

Yield=0.57 g (30%)
MP=196°-197°
NMR, IR, and mass spectra were consistent with the structure of the desired product.
MW=270.72
Calculated for $C_{11}H_{15}ClN_4O_2$: Theory: C, 48.80; H, 5.58; N, 20.70; Found: C, 48.69; H, 5.31; N, 20.47.

EXAMPLE 12

3-[6-Chloro-5-(1,1-dimethylethyl)-3-pyridazinyl]-4-hydroxy-1-(1-methylethyl)-2-imidazolidinone Yield=3.22 g (84%)
MP=124°-126°
NMR, IR, and mass spectra were consistent with the structure of the desired product.
MW=342.5
Calculated for $C_{14}H_{21}ClN_4O_2$: Theory: C, 53.83; H, 6.78; N, 17.95; Found: C, 53.77; H, 6.50; N, 18.04.

EXAMPLE 13

3-[6-Chloro-5-(1,1-dimethylethyl)-3-pyridazinyl]-4-methoxy-1-(1-methylethyl)-2-imidazolidinone Yield=0.7 g (15%)
NMR, IR, and mass spectra were consistent with the structure of the desired product.
Calculated for $C_{15}H_{23}ClN_4O_2$: Theory: C, 55.12; H, 7.09; N, 17.14; Found: C, 54.67; H, 6.74; N, 17.18.

EXAMPLE 14

3-[6-Chloro-5-(1,1-dimethylethyl)-3-pyridazinyl]-1-ethyl-4-hydroxy-2-imidazolidinone Yield=1.05 g (24%)
MP=68°-70°
NMR, IR, and mass spectra were consistent with the structure of the desired product.
MW=298.5
Calculated for $C_{13}H_{19}ClN_4O$: Theory: C, 52.26; H, 6.41; N, 18.75; Found: C, 50.46; H, 6.47; N, 17.88.

EXAMPLE 15

1-[6-Chloro-5-(1,1-dimethylethyl)-3-pyridazinyl]-3-ethyl-1,3-dihydro-2H-imidazol-2-one Yield=0.85 g (20%)
MP=124°-126°
NMR, IR, and mass spectra were consistent with the structure of the desired product.
MW=280.5
Calculated for $C_{13}H_{17}ClN_4O$: Theory: C, 55.62; H, 6.10; N, 19.96; Cl, 12.63; Found: C, 55.87; H, 6.30; N, 19.95; Cl, 12.80.

EXAMPLE 16

4-Hydroxy-1-methyl-3-(6-phenoxy-3-pyridazinyl)-2-imidazolidinone

Yield=0.72 g (56%)
MP=180.5°-182.5°
NMR, IR, and mass spectra were consistent with the structure of the desired product.
MW=286.28
Calculated for $C_{14}H_{14}N_4O_3$: Theory: C, 58.74; H, 4.93; N, 19.57; Found: C, 58.45; H, 4.66; N, 19.31.

EXAMPLE 17

3-[6-(4-Chlorophenyl)-3-pyridazinyl]-1-methyl-4-hydroxy-2-imidazolidinone

Yield=0.25 g (40%)
MP=212°-214°
NMR, IR, and mass spectra were consistent with the structure of the desired product.
MW=304.73
Calculated for $C_{14}H_{13}ClN_4O_2$: Theory: 55.18; H, 4.30; N, 18.39; Found: 55.31; H, 4.51; N, 18.10.

EXAMPLE 18

3-[6-Chloro-5-(1,1-dimethylethyl)-3-pyridazinyl]-1-methyl-2-imidazolidinone

Under a nitrogen purge, 0.3 g (0.0075 moles) of sodium hydride was washed twice with 10-ml portions of hexane. Twenty ml of toluene was added, followed by 0.75 g (0.0075 moles) of 1-methyl-2-imidazolidinone. After 15 minutes, 1.0 g (0.005 mole) of 3,6-dichloro-4-(1,1-dimethylethyl)pyridazine was added as a solid. The solution was heated to 70° for about 4.5 hours and then cooled. A 10-ml portion of 1N hydrochloric acid was added and the solution was mixed thoroughly. After adding 20 ml of ether and separating the layers, the aqueous layer was washed with 20 ml of ether. The organic layer was dried with sodium sulfate, then stripped to obtain 1.22 g (91%) of a white solid. After recrystallizing from a mixture of ethyl acetate and hexane, 0.90 g of a soft white solid was obtained. The product had a melting point of 180°-182°. NMR, IR, and mass spectra were consistent with the structure of the desired product.

The following elemental analysis was obtained:
Calculated for $C_{12}H_{17}ClN_4O$: Theory: C, 53.63; H, 6.38; N, 20.85; Found: C, 53.84; H, 6.21; N, 20.89.

EXAMPLE 19

3-[6-Chloro-5-(1,1-dimethylethyl)-3-pyridazinyl]-1-methyl-4,5-dihydroxy-2-imidazolidinone A solution of 5.97 g (0.0412 mole, 5.0 equivalents) of 40% aqueous glyoxal, adjusted to a pH of 5 using 1.0N sodium hydroxide, was added to a solution of 2.0 g (0.00824 mole) of N'-[6-chloro-5-(1,1-dimethylethyl)-3-pyridazinyl]-N-methylurea and 100 ml of THF. The mixture was stirred for about 20 hours at room temperature and then was concentrated to a residue, which was triturated in water.

A white powder was collected, dissolved in 500 ml of ethyl acetate, and dried with magnesium sulfate. Concentration afforded 2.12 g (85%) of a white material, which had a melting point of 176°-176.5°. The molecular weight was 300.75 and NMR and mass spectra were consistent with the structure of the desired product.

The following elemental analysis was obtained:
Calculated for $C_{12}H_{17}ClN_4O_3$: Theory: C, 47.93; H, 5.70; N, 18.63; Found: C, 48.14; H, 5.41; N, 18.53.

EXAMPLE 20

4-(Acetyloxy)-3-[6-chloro-5-(1,1-dimethylethyl)-3-pyridazinyl]-1-methyl-2-imidazolidinone A solution 1.50 g (0.00527 mole) of 3-[6-chloro-5-(1,1-dimethylethyl)-3-pyridazinyl]-4-hydroxy-1-methyl-2-imidazolidinone in 10 ml of THF was added dropwise to a suspension of 0.253 g (0.00632 mole, 1.20 equivalents) of 60% sodium hydride in 20 ml of dry THF, keeping the temperature below 5°. While maintaining the temperature below 5°, 0.455 g (0.00580 mole, 1.10 equivalents) of acetyl chloride was added in a dropwise manner. The reaction mixture was allowed to warm to room temperature and was stirred for about 16 hours.

The mixture was filtered and the filtrate was concentrated to an oil. This oil was chromatographed on silica gel using a 90/10 ratio of methylene chloride and ether as the eluent. A fraction weighing 1.33 g was triturated under pentane, affording 1.19 g (69%) of a white powder with a melting point of 136°-136.5°. NMR, IR, and mass spectra were consistent with the structure of the desired product. The molecular weight was 326.78.

The following elemental analysis was obtained:
Calculated for $C_{14}H_{19}ClN_4O_3$: Theory: C, 51.46; H, 5.86; N, 17.14; Found: C, 51.28; H, 5.62; N, 17.29.

The following examples were prepared using the general procedure of Example 20.

EXAMPLE 21

3-[6-Chloro-5-(1,1-dimethylethyl)-3-pyridazinyl]-1-methyl-4-(1-oxopropoxy)-2-imidazolidinone Yield=1.18 g (66%)
MP=100°-101°
NMR, IR, and mass spectra were consistent with the structure of the desired product.
MW=340.81
Calculated for $C_{15}H_{21}ClN_4O_2$: Theory: C, 52.86; H, 6.21; N, 16.44; Found: C, 53.13; H, 6.18; N, 16.51.

EXAMPLE 22

4-(Benzoyloxy)-3-[6-chloro-5-(1,1-dimethylethyl)-3-pyridazinyl]-1-methyl-2-imidazolidinone Yield=1.77 g (86%)
MP=142°-143°
NMR, IR, and mass spectra were consistent with the structure of the desired product.
MW=388.85
Calculated for $C_{19}H_{21}ClN_4O_3$: Theory: C, 58.69; H, 5.44; N, 14.41; Found: C, 58.96; H, 5.38; N, 14.32.

EXAMPLE 23

2,2-Dimethylpropanoic acid,
3-[6-chloro-5-(1,1-dimethylethyl)-3-pyridazinyl]-1-methyl-2-oxo-4-imidazolidinyl ester Yield=1.33 g (68%)
MP=153°–154°
NMR, IR, and mass spectra were consistent with the structure of the desired product.
MW=368.86
Calculated for $C_{17}H_{25}ClN_4O_3$: Theory: C, 55.36; H, 6.83; N, 15.19; Found: C, 55.36; H, 6.73; N, 15.35.

EXAMPLE 24

2-Methylpropanoic acid,
3-[6-chloro-5-(1,1-dimethylethyl)-3-pyridazinyl]-1-methyl-2-oxo-4-imidazolidinyl ester Yield=1.18 g (79%)
MP=103°–105°
NMR, IR, and mass spectra were consistent with the structure of the desired product.
MW=354.83
Calculated for $C_{16}H_{23}ClN_4O_3$: Theory: C, 54.16; H, 6.53; N, 15.79; Found: C, 54.16; H, 6.32; N, 15.90.

EXAMPLE 25

2-Butenoic acid,
3-[6-chloro-5-(1,1-dimethylethyl)-3-pyridazinyl]-1-methyl-2-oxo-4-imidazolidinyl ester Yield=0.63 g (73%)
MP=120°–122°
NMR and mass spectra were consistent with the structure of the desired product.
MW=352.82
Calculated for $C_{16}H_{21}ClN_4O_3$: Theory: C, 54.47; H, 6.00; N, 15.88; Found: C, 54.29; H, 6.00; N, 15.88.

EXAMPLE 26

Hexadecanoic acid,
3-[6-chloro-5-(1,1-dimethylethyl)-3-pyridazinyl]-1-methyl-2-oxo-4-imidazolidinyl ester Yield=1.2 g (65%)
MP=66°–67°
NMR and mass spectra were consistent with the structure of the desired product.
Calculated for $C_{28}H_{47}ClN_4O_3$: Theory: C, 64.28; H, 9.06; N, 10.71; Found: C, 64.54; H, 8.86; N, 10.74.

EXAMPLE 27

Dimethylcarbamic acid,
3-[6-chloro-5-(1,1-dimethyethyl)-3-pyridazinyl]-1-methyl-2-oxo-4-imidazolidinyl ester Yield=1.0 g (80%)
NMR, IR, and mass spectra were consistent with the structure of the desired product.
MW=355.83
Calculated for $C_{15}H_{22}ClN_5O_3$: Theory: C, 50.63; H, 6.23; N, 19.68; Found: C, 50.34; H, 5.99; N, 19.47.

EXAMPLE 28

Hexanoic acid,
3-[6-chloro-5-(1,1-dimethylethyl)-3-pyridazinyl]-1-methyl-2-oxo-4-imidazolidinyl ester Yield=0.97 g (60%)
MP=83°–85°
NMR, IR, and mass spectra were consistent with the structure of the desired product.
MW=382.89
Calculated for $C_{18}H_{27}ClN_4O_3$: Theory: C, 56.46; H, 7.11; N, 14.63; Found: C, 56.55; H, 7.30; N, 14.58.

EXAMPLE 29

Octanoic acid,
3-[6-chloro-5-(1,1-dimethylethyl)-3-pyridazinyl]-1-methyl-2-oxo-4-imidazolidinyl ester Yield=1.29 g (75%)
NMR, IR, and mass spectra were consistent with the structure of the desired product.
MW=410.94
Calculated for $C_{20}H_{31}ClN_4O_3$: Theory: C, 58.46; H, 7.60; N, 13.63; Found: C, 58.67; H, 7.53; N, 13.41.

EXAMPLE 30

Diethylcarbamic acid,
3-[6-chloro-5-(1,1-dimethylethyl)-3-pyridazinyl]-1-methyl-2-oxo-4-imidazolidinyl ester Yield: 1.1 g (54%)
MP=103°–104.5°
NMR, IR, and mass spectra were consistent with the structure of the desired product.
MW=383.88
Calculated for $C_{17}H_{26}ClN_5O_3$: Theory: C, 53.18; H, 6.83; N, 18.24; Found: C, 53.22; H, 7.12; N, 18.01.

EXAMPLE 31

3-[6-Chloro-5-(1,1-dimethylethyl)-3-pyridazinyl]-1,3-dihydro-1-methyl-2H-imidazol-2-one To a solution of 1.8 g of 3-[6-chloro-5-(1,1-dimethylethyl)-3-pyridazinyl]-4-hydroxy-1-methyl-2-imidazolidinone in about 20 ml of dry benzene was added 0.83 g (0.105 mole, 2.0 equivalents) of pyridine, followed by 0.63 g (0.0079 mole, 1.5 equivalents) of acetyl chloride. The reaction mixture was heated to 60°–65° for about 1.5 hours and then allowed to cool. After diluting with benzene, washing with 40 ml of water, and washing with 45 ml of 0.1N hydrochloric acid, the solution was filtered through phase separating paper and concentrated to give 1.3 g of a white solid. The solid was chromatographed on silica gel using a 90/10 ratio of methylene chloride and ether as the eluent.

The yield was 1.3 g (75%) and the product had a melting point of 184.5°–185.5°. The molecular weight was 326.78 and NMR, IR, and mass spectra were consistent with the structure of the desired product.

The following elemental analysis was obtained:
Calculated for $C_{12}H_{15}ClN_4O$: Theory: C, 54.04; H, 5.67; N, 21.00; Found: C, 54.32; H, 5.44; N, 21.04.

EXAMPLE 32

3-[5-(1,1-Dimethylethyl)-3-pyridazinyl]-1-methyl-4-hydroxy-2-imidazolidinone

A mixture of 2.0 g (0.00702 mole) of 3-[6-chloro-5-(1,1-dimethylethyl)-3-pyridazinyl]-4-hydroxy-1-methyl-2-imidazolidinone, 2.0 ml of concentrated ammonium hydroxide, 300 milligrams (mg) of 10% palladium on carbon, and 100 ml of 2B ethanol was placed on a Parr shaker apparatus at 50 pounds of hydrogen. After one hour, when the consumption of hydrogen exceeded the theoretical amount, the mixture was filtered and concentrated, giving 2.15 g of a white solid, which was partitioned between 400 ml of methylene chloride and 40 ml of water. The layers were separated and the organic layer was dried with magnesium sulfate.

Upon concentration, 1.6 g (91%) of a white powder was collected, which had a melting point of 165°–167.5°. The product had a molecular weight of 250.30 and NMR and mass spectra were consistent with the structure of the desired product.

The following elemental analysis was obtained:
Calculated for $C_{12}H_{18}N_4O_2$: Theory: C, 57.58; H, 7.25; N, 22.38; Found: C, 57.35; H, 7.11; N, 22.21.

The following example was prepared using the general procedure of Example 7.

EXAMPLE 33

3-[6-Chloro-5-(1,1-dimethylethyl)-3-pyridazinyl]-5-hydroxy-1-methyl-2-imidazolidinone Yield = 1.15 g (43%)
MP = 176°–177°
NMR, IR, and mass spectra were consistent with structure of the desired product.
MW = 284.5
Calculated for $C_{12}H_{17}ClN_4O_2$: Theory: C, 50.62; H, 6.02; N, 19.68; Cl, 12.45; Found: C, 50.46; H, 5.90; N, 19.53; Cl, 12.49.

EXAMPLE 34

1-[6-Chloro-5-(1,1-dimethylethyl)-3-pyridazinyl]-5-hydroxy-3,4,4-trimethyl-2-imidazolidinone A mixture of 0.159 g (0.00418 mole) of lithium aluminum hydride in 40 ml of ether was cooled in ice water. A solution of 1.30 g (0.00418 mole) of 1-[6-chloro-5-(1,1-dimethylethyl)-3-pyridazinyl]-5-oxo-3,4,4-trimethyl-2-imidazolidinone in 15 ml of ether and 10 ml of dry THF was added dropwise to the mixture. After allowing the reaction to warm to room temperature for about 1 hour, 0.32 g (0.0084 mole) of lithium aluminum hydride was added.

The reaction then was cooled in ice. Ten ml of water was cautiously added, followed by 5 ml of 30% aqueous sulfuric acid and then 10 ml of 0.5N sodium hydroxide. The resulting layers were separated and the aqueous layer was extracted with ether. The organic layers were combined, washed with saturated brine, and dried with magnesium sulfate. The concentrated material was recrystallized from an ethyl acetate/hexane mixture. The product weighed 0.21 g (15%) and had a melting point of 170°–171°. NMR, IR, and mass spectra were consistent with the structure of the desired product. The molecular weight was 312.80.

The following elemental analysis was obtained:
Calculated for $C_{14}H_{21}ClN_4O_2$: Theory: C, 53.76; H, 6.77; N, 17.91; Found: C, 53.99; H, 6.83; N, 18.00.

The following examples were prepared using one of the general procedures described above.

EXAMPLE 35

4-Hydroxy-1-methyl-3-(3-pyridazinyl)-2-imidazolidinone

Yield = 0.58 g (61%)
MP = 166.5°–167.5°
NMR, IR, and mass spectra were consistent with the structure of the desired product.
MW = 194.19
Calculated for $C_8H_{10}N_4O_2$: Theory: C, 49.48; H, 5.19; N, 28.85; Found: C, 49.26; H, 5.30; N, 28.61.

EXAMPLE 36

2-Chlorobenzoic acid, 3-[6-chloro-5-(1,1-dimethylethyl)-3-pyridazinyl]-1-methyl-2-oxo-4-imidazolidinyl ester Yield = 0.53 g (36%)
MP = 121.5°–122°
NMR, IR, and mass spectra were consistent with the structure of the desired product.
Calculated for $C_{19}H_{20}Cl_2N_4O_3$: Theory: C, 53.91; H, 4.76; N, 13.24; Found: C, 54.19; H, 4.51; N, 13.49.

EXAMPLE 37

3-(Trifluoromethyl)benzoic acid, 3-[6-chloro-5-(1,1-dimethylethyl)-3-pyridazinyl]-1-methyl-2-oxo-4-imidazolidinyl ester Yield = 1.23 g (78%)
MP = 122°–123°
NMR, IR, and mass spectra were consistent with the structure of the desired product.
MW = 456.85
Calculated for $C_{20}H_{20}ClF_3N_4O_3$: Theory: C, 52.58; H, 4.41; N, 12.26; Found: C, 52.31; H, 4.50; N, 12.06.

EXAMPLE 38

2,4-Dichlorobenzoic acid, 3-[6-chloro-5-(1,1-dimethylethyl)-3-pyridazinyl]-1-methyl-2-oxo-4-imidazolidinyl ester Yield = 0.66 g (50%)
MP = 122.5°–123°
NMR, IR, and mass spectra were consistent with the structure of the desired product.
MW = 457.74
Calculated for $C_{19}H_{19}Cl_3N_4O_3$: Theory: C, 49.86; H, 4.18; N, 12.24; Found: C, 50.13; H, 4.35; N, 12.20.

EXAMPLE 39 cis-4-Chlorobenzoic acid, 1-[6-chloro-5-(1,1-dimethylethyl)-3-pyridazinyl]-3-methyl-2-oxo-4,5-imidazolidinediyl ester Yield = 0.47 g (22%)
NMR, IR, and mass spectra were consistent with the structure of the desired product.
Calculated for $C_{26}H_{23}ClN_4O_5$: Theory: C, 54.04; H, 4.01; N, 9.79; Found: C, 54.27; H, 4.21; N, 9.63.

EXAMPLE 40

4-Fluorobenzoic acid, 3-[6-chloro-5-(1,1-dimethylethyl)-3-pyridazinyl]-1-methyl-2-oxo-4-imidazolidinyl ester Yield = 0.57 g (45%)
MP = 152°
NMR, IR, and mass spectra were consistent with the structure of the desired product.
MW = 406.84
Calculated for $C_{19}H_{20}ClFN_4O_3$: Theory: C, 56.09; H, 4.96; N, 13.77; Found: C, 56.20; H, 4.85; N, 13.89.

EXAMPLE 41

4-(Trifluoromethyl)benzoic acid, 3-[6-chloro-5-(1,1-dimethylethyl)-3-pyridazinyl]-1-methyl-2-oxo-4-imidazolidinyl ester Yield = 0.47 g (33%)
MP = 154°

NMR, IR, and mass spectra were consistent with the structure of the desired product.
MW=456.85
Calculated for $C_{20}H_{20}ClF_3N_4O_3$: Theory: C, 52.58; H, 4.41; N, 12.26; Found: C, 52.60; H, 4.33; N, 12.19.

EXAMPLE 42

4-Methylbenzoic acid, 3-[6-chloro-5-(1,1-dimethylethyl)-3-pyridazinyl]-1-methyl-2-oxo-4-imidazolidinyl ester Yield=0.42 g (32%)
MP=144.5°-146.5°
NMR and mass spectra were consistent with the structure of the desired product.
MW=402.88
Calculated for $C_{20}H_{23}ClN_4O_3$: Theory: C, 59.63; H, 5.75; N, 13.91; Found: C, 59.81; H, 5.66; N, 13.69.

EXAMPLE 43

2,6-Dichlorobenzoic acid, 3-[6-chloro-5-(1,1-dimethylethyl)-3-pyridazinyl]-1-methyl-2-oxo-4-imidazolidinyl ester Yield=0.67 g (46%)
MP=108°-109°
NMR and mass spectra were consistent with the structure of the desired product.
MW=457.74
Calculated for $C_{19}H_{19}Cl_3N_4O_3$: Theory: C, 49.86; H, 4.18; N, 12.24; Found: C, 49.63; H, 4.08; N, 12.03.

EXAMPLE 44

3,4-Dichlorobenzoic acid, 3-[6-chloro-5-(1,1-dimethylethyl)-3-pyridazinyl]-1-methyl-2-oxo-4-imidazolidinyl ester Yield=0.74 g (42%)
MP=147°
NMR, IR, and mass spectra were consistent with the structure of the desired product.
MW=457.74
Calculated for $C_{19}H_{20}Cl_3N_4O_3$: Theory: C, 49.86; H, 4.18; N, 12.24; Found: C, 49.94; H, 4.13; N, 12.21.

EXAMPLE 45

3-Chlorobenzoic acid, 3-[6-chloro-5-(1,1-dimethylethyl)-3-pyridazinyl]-1-methyl-2-oxo-4-imidazolidinyl ester Yield=1.20 g (82%)
MP=130.5°-131.5°
NMR, IR, and mass spectra were consistent with the structure of the desired product.
MW=423.29
Calculated for $C_{19}H_{21}Cl_2N_4O_3$: Theory: C, 53.91; H, 4.76; N, 13.24; Found: C, 53.80; H, 4.52; N, 13.35.

EXAMPLE 46

4-Methoxybenzoic acid, 3-[6-chloro-5-(1,1-dimethylethyl)-3-pyridazinyl]-1-methyl-2-oxo-4-imidazolidinyl ester Yield=1.24 g (85%)
MP=161°
NMR, IR, and mass spectra were consistent with the structure of the desired product.
MW=418.88
Calculated for $C_{20}H_{23}ClN_4O_4$: Theory: C, 57.35; H, 5.53; N, 13.38; Found: C, 58.45; H, 5.70; N, 13.40.

EXAMPLE 47

3-Methylbenzoic acid, 3-[6-chloro-5-(1,1-dimethylethyl)-3-pyridazinyl]-1-methyl-2-oxo-4-imidazolidinyl ester Yield=0.71 g (61%)
MP=143°-144°
NMR, IR, and mass spectra were consistent with the structure of the desired product.
MW=402.88
Calculated for $C_{20}H_{20}ClN_4O_3$: Theory: C, 59.63; H, 5.75; N, 13.91; Found: C, 59.73; H, 5.63; N, 14.15.

EXAMPLE 48

4-Cyanobenzoic acid, 3-[6-chloro-5-(1,1-dimethylethyl)-3-pyridazinyl]-1-methyl-2-oxo-4-imidazolidinyl ester Yield=0.62 g (48%)
MP=154°
NMR and mass spectra were consistent with the structure of the desired product.
MW=413.86
Calculated for $C_{20}H_{20}ClN_5O_3$: Theory: C, 58.04; H, 4.87; N, 16.92; Found: C, 58.32; H, 4.73; N, 16.93.

EXAMPLE 49

4-Bromobenzoic acid, 3-[6-chloro-5-(1,1-dimethylethyl)-3-pyridazinyl]-1-methyl-2-oxo-4-imidazolidinyl ester Yield=0.91 g (60%)
MP=166° (dec)
NMR and mass spectra were consistent with the structure of the desired product.
MW=467.76
Calculated for $C_{19}H_{20}BrClN_4O_3$: Theory: C, 48.79; H, 4.31; N, 11.98; Found: C, 48.99; H, 4.06; N, 11.97.

EXAMPLE 50

4-Nitrobenzoic acid, 3-[6-chloro-5-(1,1-dimethylethyl)-3-pyridazinyl]-1-methyl-2-oxo-4-imidazolidinyl ester Yield=0.54 g (37%)
MP=143° (dec)
NMR and mass spectra were consistent with the structure of the desired product.
MW=433.85
Calculated for $C_{19}H_{20}ClN_5O_5$: Theory: C, 52.60; H, 4.65; N, 16.14; Found: C, 52.84; H, 4.70; N, 16.30.

EXAMPLE 51

3-Methoxybenzoic acid, 3-[6-chloro-5-(1,1-dimethylethyl)-3-pyridazinyl]-1-methyl-2-oxo-4-imidazolidinyl ester Yield=1.13 g (79%)
MP=138°-139°
NMR and mass spectra were consistent with the structure of the desired product.
MW=418.88
Calculated for $C_{20}H_{20}ClN_4O_4$: Theory: C, 57.35; H, 5.53; N, 13.38; Found: C, 58.68; H, 6.03; N, 14.01.

EXAMPLE 52

3,5-Dimethoxybenzoic acid,
3-[6-chloro-5-(1,1-dimethylethyl)-3-pyridazinyl]-1-methyl-2-oxo-4-imidazolidinyl ester Yield=1.24 g (78%)
MP=146°-147°
NMR and mass spectra were consistent with the structure of the desired product.
MW=448.90
Calculated for $C_{21}H_{26}ClN_4O_5$: Theory: C, 56.19; H, 5.61; N, 12.48; Found: C, 56.36; H, 5.87; N, 12.29.

EXAMPLE 53

1-Naphthalenecarboxylic acid,
3-[6-chloro-5-(1,1-dimethylethyl)-3-pyridazinyl]-1-methyl-2-oxo-4-imidazolidinyl ester Yield=1.26 g (81%)
MP=143°-143.5°
NMR and mass spectra were consistent with the structure of the desired product.
MW=438.91
Calculated for $C_{23}H_{23}ClN_4O_3$: Theory: C, 62.94; H, 5.28; N, 12.76; Found: C, 62.81; H, 5.40; N, 12.61.

EXAMPLE 54

Methylphenylcarbamic acid,
3-[6-chloro-5-(1,1-dimethylethyl)-3-pyridazinyl]-1-methyl-2-oxo-4-imidazolidinyl ester Yield=1.75 g (79%)
MP=142° (dec)
NMR, IR, and mass spectra were consistent with the structure of the desired product.
MW=417.89
Calculated for $C_{20}H_{24}ClN_5O_3$: Theory: C, 57.48; H, 5.79; N, 16.76; Found: C, 57.34; H, 5.65; N, 16.64.

EXAMPLE 55

Diphenylcarbamic acid,
3-[6-chloro-5-(1,1-dimethylethyl)-3-pyridazinyl]-1-methyl-2-oxo-4-imidazolidinyl ester Yield=0.975 g (38%)
MP=140°-141.5°
NMR, IR, and mass spectra were consistent with the structure of the desired product.
MW=479.96
Calculated for $C_{25}H_{26}ClN_5O_3$: Theory: C, 64.46; H, 5.46; N, 14.59; Found: C, 62.33; H, 5.40; N, 14.40.

EXAMPLE 56

4-Chlorobenzoic acid,
3-[6-chloro-5-(1,1-dimethylethyl)-3-pyridazinyl]-1-methyl-2-oxo-4-imidazolidinyl ester Yield=0.84 g (56)
MP=159°
NMR, IR, and mass spectra were consistent with the structure of the desired product.
MW=387.84
Calculated for $C_{19}H_{20}Cl_2N_4O_3$: Theory: C, 53.91; H, 4.76; N, 13.24; Found: C, 54.01; H, 4.57; N, 12.99.

EXAMPLE 57

Methylphenylcarbamic acid,
3-[5-(1,1-dimethylethyl)-3-pyridazinyl]-1-methyl-2-oxo-4-imidazolidinyl ester Yield=1.16 g (38%)
MP=140°-141° (dec)
NMR, IR, and mass spectra were consistent with the structure of the desired product.
MW=383.44
Calculated for $C_{20}H_{25}N_5O_3$: Theory: C, 62.65; H, 6.57; N, 18.26; Found: C, 62.75; H, 6.29; N, 17.97.

EXAMPLE 58

2-Methoxybenzoic acid,
3-[6-chloro-5-(1,1-dimethylethyl)-3-pyridazinyl]-1-methyl-2-oxo-4-imidazolidinyl ester Yield=1.15 g (78%)
MP=145°-146°
NMR and mass spectra were consistent with the structure of the desired product.
MW=418.88
Calculated for $C_{19}H_{23}ClN_4O_4$: Theory: C, 57.35; H, 5.53; N, 13.38; Found: C, 57.55; H, 5.61; N, 13.45.

EXAMPLE 59

3,5-Dichlorobenzoic acid,
3-[6-chloro-5-(1,1-dimethylethyl)-3-pyridazinyl]-1-methyl-2-oxo-4-imidazolidinyl ester Yield=0.90 g (55%)
MP=116°-117°
NMR and mass spectra were consistent with the structure of the desired product.
MW=457.74
Calculated for $C_{19}H_{19}Cl_3N_4O_3$: Theory: C, 49.86; H, 4.18; N, 12.24; Found: C, 49.61; H, 4.00; N, 12.38.

EXAMPLE 60

2-Methylbenzoic acid,
3-[6-chloro-5-(1,1-dimethylethyl)-3-pyridazinyl]-1-methyl-2-oxo-4-imidazolidinyl ester Yield=1.06 g (80%)
MP=138°-139°
NMR and mass spectra were consistent with the structure of the desired product.
MW=402.88
Calculated for $C_{20}H_{23}ClN_4O_3$: Theory: C, 59.63; H, 5.75; N, 13.91; Found: C, 59.65; H, 5.54; N, 14.07.

EXAMPLE 61

2-(Trifluoromethyl)benzoic acid,
3-[6-chloro-5-(1,1-dimethylethyl)-3-pyridazinyl]-1-methyl-2-oxo-4-imidazolidinyl ester Yield=1.13 g (79%)
MP=125°-125.5°
NMR and mass spectra were consistent with the structure of the desired product.
MW=456.85
Calculated for $C_{20}H_{20}ClF_3N_4O_3$: Theory: C, 52.58; H, 4.41; N, 12.26; Found: C, 52.80; H, 4.64; N, 12.39.

EXAMPLE 62

3-Fluorobenzoic acid,
3-[6-chloro-5-(1,1-dimethylethyl)-3-pyridazinyl]-1-methyl-2-oxo-4-imidazolidinyl ester Yield = 0.31 g (23%)
MP = 134°-135°
NMR spectrum was consistent with the structure of the desired product.
MW = 406.84
Calculated for $C_{19}H_{20}ClFN_4O_3$: Theory: C, 56.09; H, 4.96; N, 13.77; Found: C, 56.36; H, 4.69; N, 13.78.

EXAMPLE 63

2,6-Dimethoxybenzoic acid,
3-[6-chloro-5-(1,1-dimethylethyl)-3-pyridazinyl]-1-methyl-2-oxo-4-imidazolidinyl ester Yield = 0.63 g (42%)
MP = 151.5°-152°
NMR and mass spectra were consistent with the structure of the desired product.
MW = 448.90
Calculated for $C_{21}H_{25}ClN_4O_5$: Theory: C, 56.19; H, 5.61; N, 12.48; Found: C, 56.33; H, 5.84; N, 12.55.

TERRESTRIAL HERBICIDAL METHOD

Also provided by this invention is a method of inhibiting the growth of unwanted vegetation which comprises contacting the vegetation or the soil in which the vegetation is growing with a herbicidally-effective amount of a compound of the formula (I). The pyridazinylimidazolidinones provided by this invention exhibit terrestrial herbicidal activity and accordingly are useful in the control and elimination of unwanted vegetative growth.

The herbicides of the invention are effective terrestrially in both preemergent and postemergent control of a wide variety of grasses, broadleaf weeds, and sedges. Commonly encountered unwanted terrestrial vegetation, which is subject to control with the herbicidal compounds of this invention include:

Wild Oat (*Avena fatua*)
Catchweed Bedstraw (*Galium aparine*)
Scentless Mayweed (*Matricaria inodora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthemum (Chrysantheum spp.)
Common Purslane (*Portulaca oleracea*)
Sida (Sida spp.)
Bristly Starbur (*Acanthospermum hispidum*)
Goosegrass (*Elusine indica*)
Smooth Pigweed (*Amaranthus hybridus*)
Alexandergrass (*Brachiaria plantaginea*)
Tall Morningglory (*Ipomoea purpurea*)
Common Lambsquarter (*Chenopodium album*)
Green Smartweed (*Polygonum scabrum*)
Green Foxtail (*Setaria viridis*)
Redroot Pigweed (*Amaranthus retroflexus*)
Wild Buckwheat (*Polygonum convolvulus*)
Brazil Calalilly (*Richardia brasiliensis*)
Natal Grass (*Rhynchelytrum roseum*)
Ryegrass (*Lolium rigidum*)
Kapeweed (*Cryptostemma calendula*)
Purple Loosestrife (*Lythrum salicaria*)
Wild Radish (*Raphanus raphanistrum*)
Wireweed (*Polygonum aviculare*)
Henbit (*Lamium amplexicaule*)
Swild Mustard (*Brassica kaber*)
Barnyard Grass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annual Bluegrass (*Poa annua*)
Buttercup (Ranunculus spp.)
Field Speedwell (*Veronica agrestis*)
Field Violet (*Viola arvensis*)
Field Pennycress (*Thlaspi arvense*)
Wild Violet (*Viola tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sandbur (*Cenchrus echinatus*)
Large Crabgrass (*Digitaria sanguinalis*)
Cheat (*Bromus secalinus*)
Morningglory (Ipomea spp.)
Common Ragweed (*Ambrosia artemisiifolia*)
Common Milkweed (*Asclepias syriaca*)
Giant Foxtail (Setaria faberi)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Prickly Sida (*Sida spinosa*)
Corn Gromwell (*Lithospermum arvense*)
Yellow Foxtail (*Setaria glauca*)
Tansymustard (*Descurainia pinnata*)
Pepperweed (Lepidium spp.)
Bromegrass (Bromus spp.)
Garden Spurge (*Euphorbia hirta*)
Crowfootgrass (*Dactyloctenium aegyptium*)
Florida Beggarweed (*Desmodium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella bursa-pastoris*)
Italian Ryegrass (*Lolium multiflorum*)
London Rocket (*Sisymbrium irio*)
Redmaids Rockpurslane (*Calandrinia caulescens*)
Common Groundsel (*Senecio vulgaris*)
Ivyleaf Morningglory (*Ipomoea hederacea*)
Fall Panicum (*Panicum dichotomiflorum*)
Powell Amaranth (*Amaranthus powellii*)
Texas Panicum (*Panicum texanum*)
Hemp Sesbania (*Sesbania exaltata*)
Annual Sowthistle (*Sonchus oleraceus*)
Field Bindweed (*Convolvulus arvensis*)
Erect Knotweed (*Polygonum erectum*)
Venice Mallow (*Hibiscus trionum*)
Zinnia (*Zinnia elegens*)
Nightshade (Solanum spp.)
Browntop Panicum (*Panicum fasciculatum*)
Seedling Johnsongrass (*Sorghum halepense*)
Wild Proso Millet (*Panicum miliaceum*)

The present compounds have also been found safe on a wide variety of desirable plant species, thereby exhibiting their unique selective capacity. Representative examples of relatively tolerant plant species, depending on the concentration of active ingredient employed and the means of application, include the following:

Corn (*Zea mays*) (Corn is the preferred crop for treatment.)
Wheat (*Triticum aestivum*)
Soybean (*Glycine max*)
Rice (*Oryza sativa*)
Barley (*Hordeum vulgare*)
Cotton (*Gossypium hirsutum*)
Sorghum (*Sorghum vulgare v. saccharatum*)
Sugarcane (*Saccharum officinarum*)
Peanut (*Arachis hypogaea*)
Alfalfa (*Medicago sativa*)
Cucumber (*Cucumis sativus*)
Tomato (*Lycopersicon esculentum*)
Sugar Beets (*Beta vulgaris*)

A test used to evaluate herbicidal efficacy was conducted at a compound concentration of 15 pounds per acre (16.8 kilograms per hectare). In this test a standard sand/soil mixture (1:1) was sterilized and added to separate containers and tomato, large crabgrass, and pigweed seeds were planted by row.

The test compounds were formulated for application by dissolving the compound into a solvent, containing acetone, ethanol, and a blend of anionic and nonionic surfactants. The solvent/compound solution was diluted with deionized water and applied postemergence to some planted containers and preemergence to others. Postemergent treatment was made 11 to 13 days after planting, while preemergent treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury, and "5" indicates death to the plant or no seedling emergence.

Table I, which follows, presents the terrestrial herbicidal activity of the compound at 15 pounds per acre (lb/A).

TABLE I

| Compound of Example No. | Terrestrial Herbicidal Activity Plant Species | | | | | |
|---|---|---|---|---|---|---|
| | Preemergence | | | Postemergence | | |
| | Tomato | Large Crab-grass | Pig-weed | Tomato | Large Crab-grass | Pig-weed |
| 1 | 3 | 1 | 3 | 5 | 5 | 5 |
| 4 | 1 | 1 | 1 | 1 | 1 | 1 |
| 5 | 4 | 3 | 3 | 5 | 5 | 5 |
| 6 | 2 | 4 | 4 | 4 | 3 | 4 |
| 7 | 4 | 3 | 3 | 5 | 5 | 5 |
| 8 | 5 | 4 | 4 | 5 | 5 | 5 |
| 19 | 5 | 4 | 5 | 5 | 5 | 5 |
| 20 | 4 | 2 | 4 | 5 | 5 | 5 |
| 21 | 5 | 4 | 4 | 5 | 5 | 5 |
| 22 | 3 | 4 | 4 | 5 | 5 | 5 |

TABLE I-continued

| Compound of Example No. | Terrestrial Herbicidal Activity Plant Species | | | | | |
|---|---|---|---|---|---|---|
| | Preemergence | | | Postemergence | | |
| | Tomato | Large Crab-grass | Pig-weed | Tomato | Large Crab-grass | Pig-weed |
| 23 | 4 | 4 | 4 | 5 | 5 | 5 |
| 24 | 2 | 4 | 4 | 5 | 5 | 5 |
| 27 | 4 | 4 | 5 | 5 | 5 | 5 |
| 28 | 4 | 4 | 4 | 5 | 5 | 5 |
| 29 | 5 | 4 | 4 | 5 | 5 | 5 |
| 30 | 4 | 4 | 4 | 5 | 5 | 5 |
| 31 | 1 | 2 | 2 | 5 | 5 | 5 |
| 32 | 4 | 4 | 4 | 5 | 5 | 5 |
| 37 | 4 | 4 | 4 | 5 | 5 | 5 |
| 45 | 3 | 5 | 5 | 5 | 5 | 5 |
| 46 | 4 | 5 | 4 | 5 | 5 | 5 |
| 49 | 3 | 5 | 3 | 3 | 5 | 5 |
| 51 | 5 | 5 | 4 | 5 | 5 | 5 |
| 52 | 4 | 4 | 4 | 5 | 5 | 5 |
| 53 | 5 | 4 | 4 | 5 | 5 | 5 |
| 54 | 5 | 5 | 5 | 5 | 5 | 5 |
| 55 | 3 | 4 | 4 | 5 | 5 | 5 |
| 56 | 3 | 4 | 4 | 5 | 5 | 5 |
| 57 | 4 | 5 | 5 | 5 | 5 | 5 |
| 58 | 4 | 4 | 4 | 5 | 5 | 5 |
| 60 | 4 | 4 | 3 | 5 | 5 | 5 |
| 61 | 3 | 4 | 4 | 5 | 5 | 5 |

The herbicidal activity of some of the compounds of the present invention was further evaluated at various application rates in a multiple-species greenhouse test. Several additional weed and crop species were utilized to determine the herbicidal activity and selectivity of the test compounds. Lower concentrations of the test compounds were obtained by serial dilution of the above-described formulation with a mixture of the surfactant and deionized water. The compounds were evaluated according to the general procedure outlined above. See Table II.

The following code was used in Table II:
A=Corn
B=Cotton
C=Soybean
D=Wheat
E=Alfalfa
F=Sugar Beets
G=Rice
H=Cucumber
I=Tomato
J=Barnyard Grass
K=Lambsquarter
L=Large Crabgrass
M=Mustard
N=Pigweed
O=Foxtail
P=Wild Oat
Q=Velvetleaf
R=Jimsonweed
S=Morningglory
T=Zinnia

[Note: 8 lb/A=8.96 kilograms per hectare (kg/ha)
4 lb/A=4.48 kg/ha
2 lb/A=2.24 kg/ha
1 lb/A=1.12 kg/ha
0.5 lb/A=0.56 kg/ha
0.25 lb/A=0.28 kg/ha
0.125 lb/A=0.14 kg/ha
0.062 lb/A=0.07 kg/ha
0.031 lb/A=0.035 kg/ha
0.016 lb/A=0.017 kg/ha.]

TABLE II

PLANT SPECIES

| Compound of Example No. | Appln. Rate lbs/A | Preemergence | | | | | | | | | | | | | | | | | | | | Postemergence | | | | | | | | | | | |
|---|---|---|---|---|---|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | I | J | A | L | M | N | O | P | Q | S | T |
| 1 | 8 | 4 | 5 | 4 | 4 | 5 | 4 | — | 5 | 4 | 4 | — | 4 | 5 | 5 | 5 | 5 | 5 | — | 4 | 5 | 5 | 4 | — | 5 | 5 | 5 | 5 | 5 | 4 | 5 | 5 |
| | 4 | 4 | 5 | 4 | 4 | 5 | 4 | — | 5 | 5 | 4 | 4 | 5 | 5 | 5 | 5 | 5 | 5 | 5 | 5 | 5 | 5 | 4 | — | 4 | 5 | 5 | 5 | 5 | 5 | 5 | 5 |
| | 2 | 1 | 1 | 1 | 2 | 3 | 5 | 2 | 2 | 5 | 4 | 5 | 4 | 4 | 5 | 5 | 4 | 5 | 4 | 5 | 5 | 5 | 4 | — | 4 | 5 | 5 | 4 | 3 | 5 | 5 | 5 |
| | 1 | 2 | 2 | 2 | 3 | 5 | 5 | 2 | 3 | 3 | 4 | 5 | 4 | 4 | 4 | 4 | 3 | 3 | 4 | 4 | 5 | 5 | 4 | — | 4 | 5 | 5 | 2 | 2 | 5 | 5 | 5 |
| | 0.5 | 1 | 1 | 2 | 1 | 4 | 3 | 2 | 2 | 3 | 3 | 4 | 4 | 4 | 4 | 5 | 4 | 3 | 4 | 5 | 4 | 5 | 5 | — | 4 | 4 | 4 | 3 | 2 | 4 | 4 | 4 |
| | 0.25 | 1 | 1 | 1 | 1 | 2 | 3 | 1 | 2 | 2 | 2 | 4 | 3 | 4 | 3 | 4 | 2 | 2 | 4 | 3 | 3 | 4 | 3 | — | 4 | 4 | 3 | 2 | 3 | 3 | 4 | 4 |
| | 0.25 | 1 | 1 | 3 | 2 | 2 | 2 | 2 | 5 | 3 | 2 | 5 | 4 | 3 | 3 | 3 | 3 | 3 | 4 | 3 | 3 | 3 | 2 | — | 3 | 3 | 3 | 3 | 2 | 3 | 3 | 3 |
| | 0.125 | 1 | 1 | 2 | 1 | 2 | 3 | 1 | 2 | 2 | 2 | 4 | 3 | 2 | 3 | 3 | 2 | 2 | 3 | 2 | 3 | 3 | 3 | — | 3 | 3 | 3 | 2 | 2 | 3 | 3 | 3 |
| | 0.062 | 1 | 1 | 1 | 1 | 2 | 1 | 1 | 1 | 2 | 2 | 2 | 2 | 2 | 3 | 3 | 2 | 2 | 2 | 2 | 2 | 2 | 2 | — | 3 | 2 | 2 | 2 | 2 | 2 | 3 | 2 |
| | 0.062 | 1 | 1 | 1 | 1 | 1 | 1 | 1 | 1 | 1 | 1 | 1 | — | 1 | 1 | 1 | 1 | 1 | 1 | 1 | 1 | 1 | 1 | — | 3 | 2 | 2 | 2 | 2 | 2 | 2 | 2 |
| | 0.031 | 1 | 1 | 1 | 1 | 1 | 1 | 1 | 1 | 1 | 1 | 1 | — | 1 | 1 | 1 | 1 | 1 | — | 1 | 1 | 1 | 1 | — | 2 | 2 | 1 | 1 | 1 | 1 | 1 | 1 |
| | 0.016 | — | — | — | — | — | — | — | — | — | — | — | — | — | — | — | — | — | — | — | — | — | — | — | 1 | 1 | 1 | 1 | 1 | 1 | 1 | 1 |
| 2 | 8 | 1 | 1 | 1 | 3 | 5 | 2 | 2 | 3 | 3 | 4 | 5 | 5 | 5 | 5 | 5 | 5 | 5 | — | 5 | 5 | 5 | 3 | — | 5 | 5 | 5 | 5 | 5 | 5 | 5 | 5 |
| | 4 | 1 | 1 | 1 | 3 | 5 | 1 | 3 | 2 | 2 | 4 | 5 | 5 | 5 | 4 | 5 | 4 | 5 | 3 | 5 | 3 | 5 | 5 | — | 5 | 5 | 5 | 5 | 5 | 5 | 5 | 5 |
| | 2 | 1 | 2 | 1 | 2 | 4 | 1 | — | 2 | 4 | 5 | 5 | 4 | 5 | 4 | 4 | 3 | 3 | 2 | 2 | 3 | 3 | 5 | — | 5 | 3 | 3 | 5 | 3 | 5 | 4 | 5 |
| | 1 | 1 | 1 | 1 | 1 | 2 | 1 | 1 | 1 | 1 | 1 | 4 | — | — | 4 | — | — | — | 1 | 2 | — | — | 3 | — | 3 | 3 | 2 | 2 | 2 | 2 | 3 | 3 |
| | 0.5 | — | — | — | — | — | — | — | — | 3 | — | — | — | — | — | — | — | — | 1 | — | — | — | — | — | — | — | — | — | — | — | — | — |
| | 0.25 | — | — | — | — | — | — | — | — | 2 | — | — | — | — | — | — | — | — | 1 | — | — | — | — | — | — | — | — | — | — | — | — | — |
| | 0.125 | — | — | — | — | — | — | — | — | 1 | — | — | — | — | — | — | — | — | — | — | — | — | — | — | — | — | — | — | — | — | — | — |
| 3 | 8 | 3 | 5 | 4 | 3 | 5 | 5 | 4 | 5 | 5 | 5 | 5 | 5 | 5 | 5 | 5 | 5 | 5 | 4 | 5 | 5 | 5 | 5 | — | 5 | 5 | 5 | 5 | 5 | 5 | 5 | 5 |
| 4 | 8 | 2 | 5 | 3 | 3 | 5 | 5 | 3 | 5 | 5 | 4 | 5 | 4 | 5 | 5 | 5 | 4 | 5 | 3 | 5 | 5 | 5 | 5 | — | 5 | 5 | 5 | 5 | 5 | 5 | 5 | 5 |
| 5 | 8 | 2 | 2 | 3 | 3 | 5 | 5 | 3 | 5 | 5 | 3 | 5 | 3 | 4 | 4 | 4 | 4 | 5 | 5 | 4 | 4 | 5 | 5 | — | 5 | 5 | 5 | 5 | 4 | 4 | 4 | 4 |
| | 4 | 2 | 4 | 4 | 4 | 5 | 5 | 3 | 5 | 4 | 3 | 5 | 4 | 4 | 4 | 4 | 4 | 4 | 3 | 3 | 3 | 4 | 4 | — | 4 | 4 | 4 | 3 | 2 | 4 | 4 | 4 |
| | 2 | 1 | 3 | 3 | 3 | 3 | 5 | 3 | 3 | 3 | 3 | 5 | 4 | 3 | 3 | 3 | 3 | 3 | — | 3 | 3 | 3 | 3 | — | 4 | 3 | 3 | 2 | 2 | 3 | 3 | 3 |
| | 1 | 1 | 1 | 1 | 1 | 2 | 3 | 1 | 2 | 3 | 3 | 3 | — | 2 | 2 | 2 | 2 | 2 | — | 2 | 2 | 2 | 2 | — | 3 | 3 | — | 2 | 2 | 2 | 2 | 2 |
| | 0.5 | — | — | — | — | — | — | — | — | 5 | — | — | — | — | — | — | — | — | — | 5 | — | — | 5 | — | 5 | 5 | 4 | 5 | 4 | 5 | 4 | 5 |
| | 0.25 | — | — | — | — | — | — | — | — | 5 | — | — | — | — | — | — | — | — | — | 4 | — | — | 5 | — | 5 | 5 | 5 | 4 | 4 | 5 | 5 | 4 |
| | 0.25 | — | — | — | — | — | — | — | — | 5 | — | — | — | — | — | — | — | — | — | 4 | — | — | 5 | — | 5 | 5 | 5 | 3 | 2 | 5 | 3 | 3 |
| | 0.125 | — | — | — | — | — | — | — | — | 5 | — | — | — | — | — | — | — | — | — | 2 | — | — | 4 | — | 3 | 3 | 2 | 2 | 2 | 4 | 2 | 2 |
| | 0.062 | — | — | — | — | — | — | — | — | 3 | — | — | — | — | — | — | — | — | — | 2 | — | — | 2 | — | 3 | 2 | 1 | — | 2 | 1 | 2 | 1 |
| 6 | 8 | 1 | 1 | 1 | 1 | 2 | 2 | 1 | 4 | 5 | 4 | 3 | 5 | 3 | 5 | 5 | 4 | 5 | 4 | 5 | 5 | 5 | 5 | — | 4 | 4 | 5 | 2 | 1 | 4 | 5 | 5 |
| | 4 | 1 | 1 | 1 | 1 | 2 | 2 | 1 | 2 | 5 | 4 | 3 | 5 | 3 | 5 | 5 | 4 | 4 | 3 | 4 | 5 | 5 | 5 | — | 3 | 3 | 5 | 2 | 2 | 3 | 5 | 5 |
| | 2 | 1 | 1 | 1 | 1 | 2 | 2 | 1 | 2 | 5 | 4 | 3 | 5 | 2 | 4 | 4 | 4 | 4 | 3 | 4 | 4 | 5 | 2 | — | 2 | 2 | 2 | 2 | 1 | 2 | 2 | 2 |
| | 1 | — | — | — | — | — | — | — | — | — | — | — | — | — | — | — | — | — | — | — | — | — | 2 | — | 2 | 2 | 2 | 2 | 1 | 2 | 2 | 2 |
| 7 | 8 | 4 | 5 | 4 | 4 | 5 | 5 | 4 | 5 | 5 | 4 | 5 | 5 | 5 | 5 | 5 | 5 | 5 | 5 | 5 | 5 | 5 | 5 | — | 5 | 5 | 5 | 5 | 4 | 5 | 5 | 5 |
| | 4 | 3 | 4 | 4 | 3 | 5 | 5 | 3 | 5 | 5 | 4 | 5 | 4 | 5 | 5 | 5 | 4 | 5 | 4 | 4 | 5 | 5 | 5 | — | 5 | 5 | 5 | 5 | 3 | 5 | 5 | 5 |
| | 2 | 1 | 1 | 2 | 2 | 5 | 5 | 3 | 4 | 5 | 3 | 5 | 4 | 5 | 5 | 5 | 4 | 4 | 3 | 4 | 4 | 5 | 5 | — | 4 | 4 | 4 | 3 | 2 | 4 | 5 | 4 |
| | 1 | 1 | 1 | 2 | 2 | 4 | 4 | 2 | 2 | 5 | 4 | 5 | 5 | 5 | 5 | 4 | 3 | 4 | 2 | 4 | 4 | 4 | 4 | — | 4 | 4 | 3 | 2 | 2 | 4 | 4 | 4 |
| | 0.5 | 1 | 2 | 4 | 3 | 4 | 3 | 2 | 2 | 4 | 3 | 5 | 4 | 4 | 4 | 4 | 3 | 3 | — | 2 | 2 | 3 | 3 | — | 3 | 3 | 3 | 2 | 2 | 3 | 2 | 3 |
| | 0.25 | 1 | 1 | 2 | 1 | 1 | 1 | 1 | 2 | 3 | 2 | 4 | 3 | 3 | 3 | 2 | 2 | 2 | — | 2 | 2 | 2 | 2 | 5 | 3 | 2 | 3 | 2 | 2 | 2 | 2 | 2 |
| | 0.25 | 1 | 1 | 1 | 3 | 2 | 2 | 2 | 2 | 3 | 2 | — | — | — | — | — | — | — | — | — | — | — | 2 | — | 2 | 2 | 2 | 2 | 2 | 2 | 2 | 2 |
| | 0.125 | — | — | — | — | — | — | — | — | — | — | — | — | — | — | — | — | — | — | — | — | — | 2 | — | 3 | 2 | 3 | 3 | 3 | 3 | 3 | 3 |
| | 0.062 | — | — | — | — | — | — | — | — | — | — | — | — | — | — | — | — | — | — | — | — | — | 5 | — | 5 | 5 | 5 | 5 | 4 | 5 | 5 | 5 |
| 8 | 8 | 3 | 3 | 3 | 2 | 2 | 4 | 4 | 5 | 5 | 4 | — | 5 | 5 | 5 | 5 | 5 | 5 | — | 5 | 5 | — | 5 | — | 5 | 5 | 5 | 3 | 5 | 5 | 5 | 5 |
| | 4 | 3 | 3 | 3 | 2 | 2 | 4 | — | 5 | 5 | 4 | 5 | 5 | 5 | 5 | 5 | 5 | 5 | 4 | 4 | 5 | 5 | 5 | — | 5 | 5 | 5 | 3 | 4 | 5 | 4 | 5 |

TABLE II-continued
PLANT SPECIES

| Compound of Example No. | Appln. Rate lbs/A | Preemergence | | | | | | | | | | | | | | | | | | | | Postemergence | | | | | | | | | | | |
|---|---|---|---|---|---|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | I | J | A | L | M | N | O | P | Q | S | T |
| | 2 | 3 | 3 | 2 | 2 | 3 | 5 | 4 | 5 | 5 | 4 | 5 | 5 | 5 | 5 | 5 | 4 | 5 | 5 | 5 | 5 | 4 | 4 | — | 5 | 5 | 5 | 5 | 4 | 5 | 5 | 5 |
| | 1 | 2 | 3 | 2 | 2 | 4 | 4 | 3 | 5 | 5 | 4 | 5 | 5 | 5 | 5 | 5 | 4 | 5 | 5 | 4 | 5 | 4 | 4 | — | 4 | 5 | 5 | 4 | 3 | 5 | 5 | 5 |
| | 1 | 5 | 5 | 5 | 5 | 5 | 5 | 5 | 5 | 5 | 4 | 5 | 5 | 5 | 5 | 5 | 5 | 5 | 5 | 4 | 5 | 5 | 4 | — | 5 | 5 | 5 | 5 | 4 | 5 | 5 | 5 |
| | 0.5 | 3 | 3 | 4 | 5 | 5 | 5 | 5 | 5 | 5 | 4 | 5 | 5 | 5 | 5 | 5 | 5 | 4 | 4 | 4 | 4 | 5 | 3 | — | 5 | 5 | 5 | 5 | 4 | 5 | 5 | 5 |
| | 0.25 | 1 | 2 | 1 | 2 | 3 | 5 | 5 | 5 | 5 | 4 | 5 | 5 | 5 | 5 | 5 | 5 | 5 | 4 | 4 | 4 | 2 | 1 | — | 4 | 5 | 3 | 3 | 2 | 4 | 4 | 4 |
| | 0.25 | 1 | 1 | 1 | 1 | 1 | 5 | 5 | 5 | 5 | 4 | 5 | 5 | 5 | 5 | 5 | 5 | 4 | 4 | 4 | 4 | 2 | — | — | 4 | 5 | 5 | 3 | 2 | 4 | 4 | 4 |
| | 0.125 | 1 | — | 1 | 2 | 3 | 5 | 3 | 4 | 4 | 3 | 4 | 3 | 3 | 5 | 5 | 3 | 4 | 4 | 4 | 2 | 1 | — | — | 3 | 3 | 3 | 2 | 2 | 4 | 3 | 3 |
| | 0.062 | — | 1 | — | 1 | 1 | 1 | 1 | 2 | 3 | 2 | 3 | 3 | 3 | 4 | 4 | 5 | 5 | 2 | 2 | 2 | — | — | 4 | 2 | 2 | 2 | 2 | — | 3 | 2 | 2 |
| | 0.062 | — | — | — | — | — | — | — | 1 | 1 | — | 2 | 2 | 2 | 2 | 1 | 1 | 2 | — | — | — | 4 | 2 | — | 4 | 5 | 5 | 4 | 4 | 5 | 4 | 4 |
| | 0.031 | — | — | — | — | — | — | — | — | 1 | — | 1 | 1 | 1 | 1 | 1 | 1 | — | 1 | — | — | 4 | 2 | — | 2 | 3 | 2 | 2 | 2 | 5 | 4 | 3 |
| | 0.016 | — | — | — | — | — | — | — | — | — | — | — | — | — | — | — | — | — | — | — | — | 3 | — | — | — | 3 | 3 | 3 | 3 | 5 | 3 | 2 |
| 9 | 8 | 3 | 3 | 2 | 2 | 5 | 5 | 4 | 5 | 5 | 4 | 5 | 5 | 5 | 5 | 5 | 5 | 5 | 5 | 5 | 5 | | | | | | | | | | | |
| | 4 | 2 | 2 | 2 | 2 | 4 | 4 | 3 | 5 | 5 | 4 | 5 | 5 | 5 | 5 | 5 | 5 | 4 | 4 | 4 | 4 | | | | | | | | | | | |
| | 2 | 1 | 1 | 1 | 2 | 2 | 2 | 3 | 4 | 4 | 2 | 5 | 5 | 3 | 3 | 4 | 4 | 4 | 4 | 4 | 5 | | | | | | | | | | | |
| | 1 | 5 | 5 | 5 | 5 | 5 | 5 | 5 | 5 | 5 | 4 | 5 | 5 | 5 | 5 | 5 | 5 | 5 | 5 | 5 | 5 | 4 | 4 | — | 4 | 5 | 4 | 4 | 4 | 5 | 5 | 5 |
| | 0.5 | 1 | 1 | 1 | 1 | 2 | 3 | 2 | 2 | 2 | 2 | 3 | 3 | 3 | 3 | 2 | 2 | 3 | 3 | 2 | 3 | 2 | 2 | — | 2 | 3 | 3 | 3 | 3 | 5 | 4 | 3 |
| | 0.25 | 1 | 1 | 1 | 1 | 2 | 1 | 2 | 2 | 3 | 1 | 3 | 2 | 3 | 3 | 3 | 3 | 2 | 3 | 3 | 3 | 2 | 2 | — | 2 | 3 | 3 | 3 | 2 | 5 | 4 | 3 |
| | 0.25 | 1 | — | 1 | 1 | 1 | 1 | 1 | 1 | 3 | 1 | 2 | 2 | 2 | 2 | 1 | 1 | 2 | 3 | 2 | 3 | 2 | — | — | 2 | 2 | 2 | 2 | 1 | 4 | 3 | 2 |
| | 0.125 | — | — | — | — | — | — | — | 1 | 1 | — | — | 1 | 1 | 1 | 1 | 1 | 1 | — | 1 | 1 | 4 | 3 | — | 3 | 3 | 3 | 3 | 4 | 5 | 4 | 4 |
| | 0.062 | — | — | — | — | — | — | — | — | — | — | — | — | — | — | — | — | — | — | — | — | — | — | — | — | — | — | — | — | — | — | — |
| 10 | 8 | 1 | 1 | 2 | 2 | 5 | 4 | 3 | 2 | 3 | 2 | — | 2 | 2 | 3 | 2 | — | 2 | — | 2 | 4 | — | — | — | — | — | — | — | — | — | — | 1 |
| | 4 | — | — | 2 | 2 | 4 | 3 | 2 | 2 | 2 | 2 | — | 2 | 2 | 2 | — | — | 2 | 3 | 2 | 3 | | | | | | | | | | | |
| | 2 | — | — | — | — | — | — | — | — | — | — | — | — | — | — | — | — | — | — | — | — | | | | | | | | | | | |
| | 1 | — | — | — | — | — | — | — | — | — | — | — | — | — | — | — | — | — | — | — | — | | | | | | | | | | | |
| 11 | 8 | 1 | 1 | 1 | 1 | 3 | 4 | 2 | 4 | 3 | 2 | 4 | 4 | 4 | 3 | 2 | 3 | 3 | 3 | 3 | 3 | — | — | — | 2 | 2 | 2 | 2 | 2 | — | 2 | 2 |
| 12 | 8 | 2 | 1 | 1 | 1 | 1 | 3 | 2 | 3 | 3 | 3 | 4 | 4 | 3 | 3 | 3 | 3 | 3 | — | 3 | 3 | 2 | 1 | — | 2 | 4 | 2 | 2 | 2 | — | 2 | 4 |
| | 4 | 2 | — | 1 | 1 | 1 | — | 1 | 3 | 2 | 2 | 3 | 3 | 3 | 2 | 2 | — | 2 | — | — | 2 | — | 2 | — | 2 | 4 | 2 | 2 | 2 | — | 2 | 5 |
| | 2 | — | — | — | — | — | — | — | 2 | 2 | — | 2 | 2 | 2 | — | — | — | — | — | — | — | — | 1 | — | 2 | 4 | 2 | 2 | 2 | — | 2 | 3 |
| 13 | 8 | — | — | — | — | — | — | — | — | — | — | — | — | — | — | — | — | — | — | — | — | — | 2 | — | 2 | 5 | 2 | 2 | 2 | — | 2 | 2 |
| | 4 | — | — | — | — | — | — | — | — | — | — | — | — | — | — | — | — | — | — | — | — | | | | | | | | | | | |
| 14 | 8 | 2 | 3 | 3 | — | 3 | 4 | 3 | 5 | 5 | 4 | 5 | 5 | 5 | 5 | 5 | 5 | 5 | 5 | 5 | 5 | 5 | 4 | — | 5 | 5 | 5 | 5 | 4 | 5 | 5 | 5 |
| | 4 | 1 | 1 | 1 | 1 | 2 | 5 | 3 | 3 | 3 | 2 | 5 | 4 | 4 | 5 | 3 | 4 | 5 | 5 | 5 | 4 | 4 | 3 | — | 4 | 4 | 3 | 3 | 3 | 3 | 4 | 4 |
| | 2 | — | 1 | — | — | 2 | 2 | 2 | 3 | 2 | 2 | 3 | 3 | 2 | 3 | 2 | 2 | 2 | 2 | 4 | 2 | 3 | 2 | — | 3 | 2 | 2 | 2 | 2 | 2 | 2 | 3 |
| | 1 | — | — | — | — | — | — | — | — | — | — | — | — | — | 2 | — | — | 1 | — | 1 | 1 | 1 | 1 | — | 2 | 2 | 2 | — | 1 | — | — | 2 |
| 15 | 0.5 | 1 | 1 | 2 | 1 | 2 | 3 | 1 | 4 | 2 | 3 | 5 | 5 | 5 | 5 | 5 | 5 | 5 | — | — | 3 | 3 | — | — | 3 | 3 | 3 | 3 | 2 | — | — | — |
| 16 | 0.25 | 1 | 1 | 2 | 1 | 2 | 2 | 2 | 3 | 2 | 2 | 5 | 2 | 3 | 2 | 2 | 2 | 2 | — | — | 2 | — | — | — | — | — | — | — | — | — | — | — |
| 17 | 8 | — | — | — | — | — | — | — | — | — | — | — | — | — | — | — | — | — | — | — | — | | | | | | | | | | | |
| | 4 | — | — | — | — | — | — | — | — | — | — | — | — | — | — | — | — | — | — | — | — | | | | | | | | | | | |
| | 2 | — | — | — | — | — | — | — | — | — | — | — | — | — | — | — | — | — | — | — | — | | | | | | | | | | | |
| 19 | 8 | — | — | — | — | — | — | — | 5 | 5 | 4 | 5 | 5 | 5 | 5 | 5 | 5 | 5 | — | 5 | 5 | 5 | 1 | — | 5 | 4 | 4 | 3 | 2 | 3 | 4 | 4 |

TABLE II-continued

PLANT SPECIES

| Compound of Example No. | Appln. Rate lbs/A | Preemergence | | | | | | | | | | | | | | | | | | | | Postemergence | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | A | B | C | D | E | F | G | H | I | J | K | L | M | N | O | P | Q | R | S | T |
| | 4 | 2 | 5 | 4 | 3 | 5 | 5 | 4 | 5 | 4 | 3 | 4 | 4 | 4 | 5 | 4 | 4 | 4 | 4 | 5 | 5 | 4 | 5 | 4 | 4 | 5 | 5 | 4 | 5 | 5 | 5 | — | 4 | 5 | 5 | 5 | 3 | 3 | 4 | 4 | 5 |
| | 2 | 2 | 3 | 3 | 2 | 3 | 4 | 3 | 5 | 4 | 4 | 4 | 5 | 5 | 4 | 4 | 5 | 5 | 4 | 5 | 4 | 4 | 5 | 4 | 3 | 4 | 5 | 4 | 5 | 4 | 4 | — | 3 | 3 | 5 | 5 | 3 | 3 | 5 | 4 | 5 |
| | 1 | 1 | 2 | 1 | — | 3 | 3 | 2 | 5 | 4 | 1 | 4 | 4 | 5 | 4 | 5 | 2 | 3 | 3 | 4 | 2 | 4 | 4 | 3 | 4 | 5 | 5 | 4 | 5 | 5 | 4 | — | 3 | 5 | 4 | 4 | 3 | 3 | 5 | 5 | 5 |
| | 0.5 | — | 1 | 2 | 4 | 2 | 3 | 2 | 4 | 4 | 2 | 5 | 4 | 5 | 3 | 4 | 2 | 3 | 3 | 4 | 3 | 3 | 3 | 2 | 3 | 2 | 4 | 2 | 4 | 4 | 4 | — | 2 | 3 | 3 | 3 | 1 | 2 | 2 | 4 | 3 |
| | 0.25 | — | — | 2 | 2 | 2 | 2 | 2 | 4 | 3 | 2 | 4 | 3 | 5 | 3 | 5 | 2 | 2 | 3 | 3 | 4 | 3 | 3 | 3 | 2 | 3 | 3 | 2 | 4 | 3 | 2 | — | 2 | 2 | 3 | 2 | 1 | 2 | 2 | 3 | 3 |
| | 0.125 | — | — | 1 | — | — | 1 | 1 | 4 | 3 | — | 3 | 3 | 3 | 1 | 5 | 1 | 2 | 2 | 3 | 2 | 3 | 2 | 2 | 2 | 2 | 2 | 1 | 3 | 2 | 2 | — | 1 | 3 | 2 | 2 | — | 2 | 2 | 2 | 3 |
| | 0.062 | — | — | — | — | — | — | — | 2 | 1 | — | 1 | — | 3 | — | 4 | 1 | — | 1 | 3 | 1 | 2 | 1 | — | 1 | — | 1 | — | 2 | — | — | — | 1 | 1 | 2 | — | — | 1 | 1 | — | 2 |
| 20 | 8 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | — | 5 | 5 | 5 | 5 | 5 | 5 | 5 | 5 | 5 |
| | 4 | — | 2 | 2 | 4 | 5 | 4 | 4 | 5 | 5 | 4 | 5 | 5 | 5 | 5 | 5 | 5 | 4 | 4 | 5 | 5 | 5 | 4 | 3 | 3 | 5 | 4 | 4 | 5 | 5 | 5 | — | 4 | 5 | 5 | 5 | 3 | 5 | 5 | 5 | 5 |
| | 2 | 2 | 2 | 3 | 2 | 5 | 4 | 4 | 5 | 5 | 4 | 5 | 4 | 5 | 5 | 5 | 4 | 5 | 5 | 4 | 5 | 4 | 4 | 2 | 2 | 3 | 3 | 2 | 5 | 4 | 3 | — | 3 | 4 | 3 | 3 | 3 | 4 | 4 | 4 | 4 |
| | 1 | — | 1 | 2 | 2 | 4 | 2 | 3 | 5 | 4 | 3 | 4 | 5 | 5 | 5 | 5 | 3 | 3 | 4 | 4 | 3 | 3 | 2 | 2 | — | 2 | 3 | 2 | 3 | 2 | 2 | — | 2 | 2 | 2 | 2 | 2 | 2 | 2 | 2 | 4 |
| | 0.5 | 1 | 1 | 2 | 1 | 2 | 4 | 2 | 3 | 2 | 2 | 4 | 3 | 5 | 3 | 5 | 2 | 2 | 2 | 2 | 2 | 1 | 2 | 2 | — | 2 | 2 | 2 | 2 | 2 | 2 | — | 3 | 3 | 3 | 3 | 2 | 2 | 2 | 2 | 2 |
| | 0.25 | — | 1 | 2 | 1 | 1 | — | 2 | 2 | 2 | 1 | 3 | 3 | 5 | 3 | 5 | 3 | — | — | 4 | — | 1 | 1 | — | — | — | 1 | 1 | 2 | 1 | 1 | — | 2 | 1 | 2 | 2 | 2 | — | — | — | — |
| | 0.125 | 1 | 1 | — | 1 | 1 | 1 | — | — | — | — | 1 | 1 | 2 | — | 3 | 1 | — | — | 1 | — | 1 | — | — | — | — | — | — | 1 | — | — | — | — | — | 1 | 1 | — | — | — | — | — |
| | 0.062 | — | — | — | — | — | — | — | — | — | — | — | — | — | — | — | — | — | — | — | — | — | — | — | — | — | — | — | — | — | — | — | — | — | — | — | — | — | — | — | — |
| 21 | 8 | 4 | 5 | 5 | 3 | 5 | 5 | 5 | 5 | 5 | 5 | 5 | 5 | 5 | 5 | 5 | 5 | 5 | 5 | 5 | 5 | 5 | 5 | 5 | 4 | 4 | 5 | 5 | 5 | 5 | 5 | — | 5 | 5 | 5 | 5 | 4 | 5 | 5 | 5 | 5 |
| | 4 | 2 | 2 | 2 | 2 | 5 | 5 | 3 | 5 | 4 | 4 | 4 | 5 | 5 | 5 | 5 | 5 | 4 | 4 | 5 | 5 | 5 | 4 | 4 | 3 | 5 | 5 | 4 | 5 | 5 | 4 | — | 4 | 5 | 5 | 5 | 4 | 5 | 4 | 4 | 5 |
| | 2 | 2 | 2 | 2 | 2 | 4 | 4 | 3 | 5 | 5 | 4 | 4 | 5 | 5 | 5 | 5 | 4 | 2 | 2 | 4 | 5 | 2 | 2 | 2 | 2 | 2 | 3 | 3 | 4 | 5 | 3 | — | 3 | 3 | 3 | 2 | 2 | 2 | 2 | 4 | 4 |
| | 1 | 1 | 2 | 2 | 1 | 3 | 3 | 2 | 5 | 4 | 3 | 4 | 4 | 5 | 5 | 5 | 4 | 2 | 2 | 4 | 3 | 2 | 2 | 2 | 1 | 1 | 2 | 2 | 3 | 2 | 2 | — | 2 | 2 | 2 | 2 | 2 | 2 | 2 | 2 | 2 |
| | 0.5 | — | 1 | 3 | 1 | 2 | 3 | 2 | 3 | 2 | 2 | 3 | 3 | 3 | 3 | 5 | 2 | 2 | 2 | 2 | 3 | 2 | 2 | 2 | 2 | — | 2 | 2 | 2 | 2 | 2 | — | 2 | 2 | 2 | 2 | 2 | 2 | 2 | 2 | 2 |
| | 0.25 | — | — | 1 | — | 1 | 1 | 1 | 2 | 2 | 1 | 1 | 1 | 2 | 3 | 5 | 3 | 1 | — | 4 | 2 | — | 1 | 1 | — | — | — | — | 1 | — | — | — | 1 | 1 | 1 | 1 | 1 | — | — | 1 | 1 |
| | 0.125 | — | — | 1 | — | — | 1 | — | 2 | — | 1 | — | — | 2 | — | 3 | 2 | — | — | 2 | 2 | — | — | — | — | — | — | — | — | — | — | — | — | — | — | — | — | — | — | — | — |
| | 0.062 | — | — | 1 | — | — | — | — | — | — | — | — | — | 2 | 2 | 3 | — | — | — | — | — | 2 | — | — | — | — | — | — | — | — | — | — | — | — | — | — | — | — | — | — | — |
| 22 | 8 | 2 | 2 | 2 | 2 | 4 | 4 | 4 | 5 | 4 | 4 | 5 | 5 | 5 | 5 | 5 | 4 | 5 | 5 | 5 | 5 | 5 | 4 | 4 | 4 | 4 | 5 | 5 | 5 | 5 | 5 | — | 5 | 5 | 5 | 5 | 4 | 5 | 5 | 5 | 5 |
| | 4 | 2 | 2 | 2 | 2 | 4 | 4 | 2 | 5 | 4 | 4 | 4 | 3 | 5 | 4 | 5 | 3 | 3 | 5 | 5 | 5 | 5 | 3 | 2 | 2 | 2 | 2 | 3 | 5 | 4 | 4 | — | 2 | 3 | 5 | 5 | 2 | 5 | 5 | 5 | 5 |
| | 2 | 2 | 2 | 2 | 2 | 3 | 2 | 2 | 2 | 3 | 2 | 4 | 4 | 2 | 5 | 4 | 2 | 2 | 2 | 3 | 3 | 2 | 2 | 2 | 2 | 2 | 2 | — | 3 | 2 | 3 | — | 2 | 2 | 2 | 2 | 2 | 2 | 2 | 2 | 2 |
| | 1 | — | — | 2 | — | 1 | 2 | 1 | 2 | 2 | 2 | 3 | 1 | — | 2 | 5 | 1 | 1 | — | — | 2 | — | 1 | 1 | — | — | — | 1 | 2 | 2 | 1 | — | 2 | 2 | 2 | 2 | 1 | 1 | 1 | — | 2 |
| | 0.5 | — | 1 | 1 | 1 | — | — | — | 2 | 2 | 2 | 2 | 3 | 2 | 3 | 5 | 1 | — | — | 2 | 2 | — | — | — | — | — | — | — | 1 | — | — | — | 2 | 2 | 2 | 2 | — | — | — | — | 2 |
| | 0.25 | — | — | — | — | — | — | — | 2 | 1 | — | — | 2 | 2 | 2 | 5 | — | — | — | — | — | — | — | — | — | — | — | — | 1 | — | — | — | — | — | — | — | — | — | — | — | 2 |
| | 0.125 | — | — | — | — | — | — | — | — | — | — | — | — | — | 3 | 5 | — | — | — | — | — | — | — | — | — | — | — | — | — | — | — | — | — | — | — | — | — | — | — | — | 2 |
| | 0.062 | — | — | — | — | — | — | — | — | — | — | — | — | — | 2 | 5 | — | — | — | — | — | — | — | — | — | — | — | — | — | — | — | — | — | — | — | — | — | — | — | — | — |
| 23 | 8 | 4 | 5 | 5 | 4 | 5 | 5 | 4 | 5 | 5 | 4 | 5 | 5 | 5 | 5 | 5 | 4 | 5 | 5 | 5 | 5 | 5 | 4 | 5 | 4 | 4 | 5 | 5 | 5 | 5 | 5 | — | 5 | 5 | 5 | 5 | 5 | 5 | 5 | 5 | 5 |
| | 4 | 3 | 4 | 3 | 3 | 3 | 4 | 3 | 5 | 5 | 4 | 4 | 4 | 5 | 3 | 5 | 2 | 4 | 5 | 5 | 4 | 4 | 4 | 4 | 3 | 3 | 4 | 4 | 4 | 5 | 4 | — | 2 | 3 | 4 | 4 | 4 | 4 | 5 | 4 | 4 |
| | 2 | 2 | 2 | 2 | 2 | 3 | 3 | 4 | 4 | 3 | 3 | 4 | 4 | 5 | 3 | 5 | 2 | 2 | 2 | 2 | 3 | 5 | 2 | 2 | 2 | 2 | 2 | 2 | 3 | 4 | 3 | — | 3 | 3 | 3 | 3 | 2 | 3 | 3 | 4 | 4 |
| | 1 | 2 | 2 | 3 | 3 | 2 | 4 | 4 | 4 | 5 | 4 | 5 | 5 | 5 | 5 | 5 | 2 | 4 | 4 | 3 | 3 | 5 | 2 | 2 | 2 | 2 | 2 | 2 | 3 | 3 | 4 | — | 2 | 2 | 2 | 2 | 2 | 2 | 2 | 2 | 3 |

TABLE II-continued
PLANT SPECIES

| Compound of Example No. | Appln. Rate lbs/A | Preemergence | | | | | | | | | | | | | | | | | | | | Postemergence | | | | | | | | | | | |
|---|---|---|---|---|---|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | I | J | A | L | M | N | O | P | Q | S | T |
| 24 | 0.5 | 1 | 2 | 1 | 1 | 1 | 4 | 2 | 2 | 4 | 4 | 5 | 5 | 5 | 5 | 5 | 2 | 4 | 2 | 1 | 2 | 5 | 4 | — | 5 | 5 | 5 | 5 | 5 | 4 | 4 | 5 |
| | 0.25 | 1 | 1 | 1 | 1 | 1 | — | 1 | — | 3 | 3 | 5 | 4 | 5 | 5 | 3 | 1 | 2 | 1 | 1 | 2 | 5 | 4 | — | 4 | 5 | 5 | 5 | 4 | 5 | 5 | 5 |
| | 0.125 | 1 | 1 | 1 | 1 | 1 | 5 | 1 | 2 | 2 | 3 | 4 | 4 | 5 | 5 | 2 | 1 | 4 | 4 | 2 | 3 | 5 | 3 | — | 5 | 4 | 4 | 5 | 2 | 5 | 4 | 5 |
| | 0.125 | 1 | 1 | 1 | 1 | 1 | — | 1 | 1 | 2 | 2 | 2 | 4 | 5 | 2 | 1 | 1 | 2 | 1 | 2 | 1 | 5 | 3 | — | 5 | 4 | 4 | 3 | 2 | 5 | 3 | 5 |
| | 0.062 | 1 | 1 | 1 | 1 | 1 | — | 1 | 1 | 2 | 2 | 2 | 2 | 4 | 2 | 1 | 1 | 1 | — | 1 | — | 5 | 2 | — | 4 | 3 | 3 | 2 | 2 | 4 | 3 | 4 |
| 25 | 8 | 5 | 5 | 4 | 5 | 5 | 5 | 5 | 5 | 5 | 5 | 5 | 5 | 5 | 5 | 5 | 5 | 5 | 5 | 5 | 5 | 5 | 5 | — | 5 | 5 | 5 | 5 | 5 | 5 | 5 | 5 |
| | 4 | 2 | 5 | 4 | 4 | 4 | 5 | 5 | 5 | 5 | 5 | 5 | 5 | 5 | 5 | 5 | 5 | 5 | 4 | 4 | 5 | 5 | 4 | — | 5 | 5 | 5 | 4 | 5 | 5 | 5 | 5 |
| | 2 | 1 | 2 | 2 | 2 | 3 | 4 | 3 | 5 | 4 | 3 | 5 | 4 | 5 | 5 | 4 | 4 | 4 | 4 | 5 | 5 | 5 | 3 | — | 5 | 5 | 4 | 3 | 4 | 5 | 4 | 3 |
| | 1 | 1 | 1 | 1 | 1 | 2 | 2 | 2 | 3 | 4 | 3 | 5 | 5 | 5 | 5 | 3 | 3 | 3 | 2 | 4 | 3 | 5 | 2 | — | 4 | 4 | 4 | 3 | 2 | 4 | 4 | 3 |
| | 0.5 | 1 | 1 | 1 | 1 | — | 2 | 1 | 2 | 2 | 2 | 4 | 4 | 5 | 4 | 2 | 2 | 3 | 2 | 3 | 3 | 5 | 2 | — | 4 | 4 | 4 | 2 | 2 | 3 | 3 | 4 |
| | 0.25 | 1 | 1 | 1 | 1 | — | 2 | 1 | 2 | 2 | 2 | 3 | 4 | 4 | 4 | 2 | 1 | 2 | 1 | 3 | 2 | 5 | 2 | — | 4 | 3 | 2 | 2 | 2 | 2 | 2 | 3 |
| | 0.125 | 1 | 1 | 1 | — | 1 | — | 1 | 2 | 2 | 2 | 2 | 2 | 4 | 3 | 2 | 1 | 2 | 1 | 2 | 2 | 4 | 2 | — | 3 | 3 | 2 | 2 | 1 | 2 | 2 | 3 |
| | 0.062 | 1 | 1 | 1 | — | 1 | — | 1 | 1 | 1 | 1 | 2 | 1 | 2 | 2 | 1 | 1 | 1 | — | 1 | 1 | 3 | 1 | — | 2 | 2 | 2 | 1 | — | 1 | 1 | 3 |
| 26 | 8 | 4 | 4 | 4 | 4 | 4 | 5 | 5 | 5 | 5 | 5 | 5 | 5 | 5 | 5 | 5 | 5 | 5 | 4 | 5 | 5 | 5 | 5 | — | 5 | 5 | 5 | 5 | 5 | 5 | 5 | 5 |
| | 4 | 2 | 3 | 2 | 5 | 4 | 5 | 4 | 5 | 5 | 5 | 5 | 5 | 5 | 5 | 5 | 3 | 5 | 4 | 5 | 5 | 5 | 4 | — | 5 | 5 | 5 | 4 | 4 | 5 | 4 | 5 |
| | 2 | 1 | 1 | 2 | 2 | 2 | 4 | 2 | 5 | 4 | 3 | 5 | 4 | 5 | 5 | 3 | 3 | 3 | 3 | 4 | 4 | 5 | 3 | — | 5 | 4 | 4 | 3 | 3 | 4 | 3 | 4 |
| | 1 | 1 | 1 | 1 | 1 | 1 | 2 | 1 | 3 | 2 | 2 | 4 | 3 | 5 | 4 | 2 | 2 | 3 | 2 | 3 | 3 | 5 | 2 | — | 4 | 4 | 3 | 2 | 2 | 3 | 3 | 4 |
| | 0.5 | 1 | 2 | 2 | 2 | 2 | 2 | 2 | 2 | 2 | 2 | 4 | 2 | 4 | 4 | 2 | 2 | 2 | 2 | 3 | 3 | 4 | 2 | — | 4 | 3 | 3 | 2 | 1 | 3 | 2 | 4 |
| | 0.25 | 1 | 1 | 1 | 1 | 1 | 1 | 1 | 2 | 1 | 1 | 3 | 2 | 3 | 2 | 2 | 1 | 2 | 1 | 2 | 2 | 3 | 2 | — | 3 | 3 | 3 | 2 | 1 | 3 | 2 | 4 |
| | 0.125 | 1 | 1 | 1 | 1 | 1 | 1 | 1 | 1 | 1 | 1 | 2 | 1 | 2 | 2 | 2 | 1 | 2 | — | 1 | — | 2 | 1 | — | 2 | 3 | 3 | 1 | — | 1 | 1 | 3 |
| | 0.062 | 1 | 1 | 1 | 1 | 1 | 1 | 1 | 1 | 1 | 1 | 1 | 1 | 2 | 2 | 2 | 1 | 1 | — | 1 | — | 2 | 1 | — | 1 | 2 | 2 | 1 | — | 1 | 1 | 3 |
| 27 | 8 | 5 | 5 | 5 | 5 | 4 | 5 | 4 | 4 | 5 | 5 | 5 | 5 | 5 | 5 | 5 | 4 | 5 | 4 | 5 | 5 | 5 | 5 | — | 5 | 5 | 5 | 5 | 5 | 5 | 5 | 5 |
| | 4 | 5 | 5 | 5 | 5 | 5 | 5 | 5 | 5 | 5 | 5 | 5 | 5 | 5 | 5 | 5 | 3 | 5 | 4 | 5 | 5 | 5 | 4 | — | 5 | 5 | 5 | 3 | 3 | 5 | 3 | 4 |
| | 2 | 5 | 5 | 4 | 3 | 3 | 3 | 2 | 2 | 3 | 3 | 4 | 4 | 4 | 4 | 4 | 2 | 3 | 3 | 4 | 2 | 5 | 3 | — | 4 | 4 | 4 | 2 | 2 | 3 | 2 | 4 |
| | 1 | 1 | 1 | 1 | 1 | 1 | 2 | 1 | 1 | 2 | 2 | 4 | 2 | 3 | 3 | 2 | — | 2 | — | 3 | 1 | 3 | 2 | — | 3 | 5 | 3 | 1 | 1 | 1 | 2 | 4 |
| | 0.5 | 1 | 1 | 1 | 1 | 1 | 2 | 1 | 1 | 1 | 1 | 2 | 1 | 2 | 2 | 2 | — | 2 | — | 2 | — | 2 | 1 | — | 2 | 3 | 2 | 1 | — | 2 | 2 | 4 |
| | 0.25 | 1 | 1 | 1 | 1 | 1 | 1 | 1 | 1 | 1 | 1 | 1 | 1 | 2 | 2 | 1 | — | 1 | — | 1 | — | 2 | — | — | 1 | 2 | 2 | — | — | 1 | 2 | 4 |
| 28 | 8 | 4 | 4 | 4 | 4 | 4 | 5 | 5 | 5 | 5 | 5 | 5 | 5 | 5 | 5 | 5 | 4 | 5 | 5 | 5 | 5 | 5 | 5 | — | 5 | 5 | 5 | 5 | 4 | 5 | 5 | 5 |
| | 4 | 4 | 1 | 1 | 2 | 4 | 5 | 3 | 5 | 5 | 5 | 5 | 5 | 5 | 5 | 5 | 4 | 5 | 5 | 5 | 5 | 5 | 4 | — | 5 | 5 | 5 | 5 | 4 | 5 | 5 | 5 |
| | 2 | 2 | 1 | 1 | 1 | 2 | 3 | 2 | 4 | 4 | 3 | 4 | 4 | 5 | 4 | 4 | 2 | 3 | 1 | 5 | 5 | 5 | 3 | — | 5 | 5 | 5 | 4 | 4 | 5 | 5 | 5 |
| 29 | 8 | 1 | 2 | 2 | 4 | 5 | 3 | 5 | 5 | 5 | 5 | 5 | 5 | 5 | 5 | 4 | 5 | 5 | — | 5 | 5 | 5 | 5 | — | 5 | 5 | 5 | 5 | 5 | 5 | 5 | 5 |
| | 4 | 2 | 2 | 1 | 2 | 1 | — | 2 | 4 | 4 | 5 | 5 | 5 | 5 | 5 | 4 | 4 | 5 | — | 5 | 5 | 5 | 5 | — | 5 | 5 | 5 | 5 | 5 | 5 | 5 | 5 |

TABLE II-continued

PLANT SPECIES

| Compound of Example No. | Appln. Rate lbs/A | Preemergence | | | | | | | | | | | | | | | | | | | | Postemergence | | | | | | | | | | |
|---|---|---|---|---|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | I | J | A | L | M | N | O | P | Q | S | T |
| 30 | 2 | 1 | 1 | 2 | 2 | 2 | 5 | 4 | 5 | 4 | 4 | 5 | 5 | 5 | 5 | 5 | 4 | 5 | 5 | 4 | 5 | 5 | 3 | — | — | 5 | 4 | 4 | 5 | 5 | 5 | 5 |
| | 1 | 1 | 1 | 2 | 2 | 1 | 2 | 3 | 5 | 3 | 5 | 5 | 4 | 5 | 5 | 5 | 2 | 3 | 4 | 3 | 4 | 5 | 5 | 2 | — | 4 | 5 | 5 | 2 | 4 | 4 | 5 |
| 31 | 8 | 3 | 2 | 3 | 3 | 5 | 5 | 4 | — | 5 | 5 | — | 5 | 5 | 5 | 5 | 5 | 3 | 5 | — | 5 | 5 | 5 | 5 | — | 5 | 5 | 5 | 4 | 4 | 5 | 5 | 5 |
| | 2 | 2 | 1 | 2 | 3 | 5 | 5 | 4 | 3 | 4 | 5 | 5 | 5 | 5 | 5 | 5 | 3 | 5 | — | 5 | 4 | 5 | 5 | 2 | — | 3 | 5 | 3 | 4 | 3 | 2 | 5 | 5 |
| | 1 | — | — | — | — | — | — | — | — | — | — | — | — | — | — | — | — | — | — | — | — | — | — | — | — | — | — | — | — | — | — | — | — |
| | 8 | 2 | 2 | 2 | 4 | 4 | 4 | 2 | 3 | 4 | 4 | 4 | 4 | 4 | 4 | 4 | 2 | 4 | 4 | 4 | 4 | 4 | 5 | 3 | — | 4 | 4 | 5 | 4 | 3 | 2 | 4 | 4 |
| | 4 | 2 | 2 | 1 | 1 | — | 3 | 3 | 2 | 2 | 2 | 4 | 3 | 5 | 3 | 5 | 3 | 2 | 3 | 4 | 4 | 5 | 5 | 2 | — | 5 | 5 | 5 | 3 | 2 | 2 | 4 | 4 |
| | 2 | 2 | 2 | 1 | 1 | 2 | 3 | 2 | 2 | 2 | 2 | 4 | 4 | 5 | 4 | 5 | 2 | 2 | 4 | 4 | 4 | 4 | 4 | 3 | — | 2 | 3 | 3 | 2 | 2 | 2 | 3 | 4 |
| | 1 | 2 | 1 | 1 | 1 | 1 | 2 | 1 | 2 | 2 | 1 | 3 | 2 | 4 | 2 | 4 | 1 | 1 | 2 | 3 | 3 | 3 | 5 | 1 | — | 2 | 4 | 4 | 2 | 2 | 3 | 4 | 4 |
| | 0.5 | 1 | — | 1 | 1 | — | 2 | 1 | 1 | 1 | 1 | 2 | 2 | 3 | 2 | 2 | 1 | 1 | 1 | 3 | 2 | 2 | 4 | 1 | — | 2 | 2 | 2 | 2 | 2 | 2 | 3 | 3 |
| | 0.25 | 1 | — | 1 | 1 | — | 1 | 1 | 1 | 1 | 1 | 1 | 2 | 2 | 2 | 2 | 1 | 1 | 1 | 3 | 2 | 2 | 3 | 1 | — | 2 | 2 | 2 | 1 | 2 | 2 | 2 | 2 |
| 32 | 8 | 4 | 5 | 3 | 4 | 5 | 5 | 4 | 5 | 5 | 4 | 5 | 5 | 5 | 5 | 5 | 4 | 5 | 5 | 5 | 5 | 5 | 5 | — | 5 | 5 | 5 | 5 | 4 | 5 | 5 | 5 | 5 |
| | 4 | 3 | 2 | 2 | 3 | 5 | 5 | 4 | 5 | 5 | 4 | 5 | 5 | 5 | 5 | 5 | 5 | 5 | 5 | 4 | 4 | 5 | 5 | 3 | — | 5 | 5 | 5 | 5 | 4 | 5 | 5 | 5 |
| | 2 | 1 | 2 | 1 | 2 | 4 | 5 | 2 | 3 | 3 | 4 | 4 | 5 | 5 | 5 | 5 | 2 | 3 | 5 | 3 | 5 | 5 | 5 | 3 | — | 5 | 4 | 4 | 3 | 3 | 5 | 4 | 5 |
| | 1 | — | 1 | 2 | 2 | 2 | 4 | 2 | 5 | 5 | 2 | 4 | 4 | 3 | 4 | 2 | 2 | 2 | 2 | 2 | 2 | 5 | 4 | 1 | — | 4 | 4 | 4 | 2 | 3 | 4 | 4 | 5 |
| | 0.5 | 1 | — | 1 | 1 | 2 | 4 | 1 | 1 | 2 | 2 | 4 | 4 | 4 | 4 | 4 | 2 | 2 | 2 | 2 | 2 | 4 | 3 | 2 | — | 2 | 2 | 2 | 2 | 2 | 2 | 4 | 3 |
| | 0.25 | — | — | — | — | — | 2 | — | 1 | 2 | 2 | — | 2 | 2 | 2 | 2 | 1 | 1 | — | 1 | — | 3 | — | 1 | — | — | — | — | — | — | — | — | — |
| | 0.25 | 1 | 1 | — | 1 | — | — | — | — | 1 | — | — | 1 | 1 | 1 | 1 | — | — | — | — | 1 | — | — | — | — | — | — | — | — | — | — | — | — |
| | 0.062 | 1 | 1 | — | 1 | — | — | — | — | 1 | — | — | 1 | 1 | 1 | 1 | — | — | — | — | — | — | — | — | — | — | — | — | — | — | — | — |
| 33 | 8 | 1 | — | — | — | 5 | 3 | — | — | 2 | 2 | 2 | — | 3 | — | — | — | — | — | 4 | — | 3 | 2 | — | — | 3 | — | — | — | — | 1 | — | 2 |
| | 4 | 1 | 1 | 1 | 1 | 4 | 2 | — | — | 1 | — | — | 1 | 1 | 1 | 1 | — | — | — | — | — | — | — | — | — | — | — | — | — | — | 1 | — | — |
| | 2 | 1 | 1 | 1 | 1 | 1 | 2 | — | — | 1 | — | — | 1 | 1 | 1 | 1 | — | — | — | — | — | — | — | — | — | — | — | — | — | — | — | — | — |
| | 1 | 1 | 1 | 1 | 1 | 1 | — | — | — | 1 | — | — | 1 | 1 | 1 | 1 | — | — | — | — | — | — | — | — | — | — | — | — | — | — | — | — |

The following code was used in Tables III and IV:
A = Corn
B = Cotton
C = Soybean
D = Wheat
E = Alfalfa
F = Sugar Beets
G = Rice
H = Cucumber
I = Tomato
J = Barley
K = Barnyard Grass
L = Lambsquarter
M = Cocklebur
N = Large Crabgrass
O = Mustard
P = Pigweed
Q = Ryegrass
R = Small Crabgrass
S = Foxtail Millet
T = Bindweed
U = Wild Oat
V = Nutgrass
W = Velvetleaf
X = Jimsonweed
Y = Smartweed
Z = Morningglory
a = Zinnia

TABLE III

| Ex. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 34 | 2 | 1 | 1 | 1 | 2 | 3 | 5 | 2 | 3 | 3 | | 4 | 5 | | 4 | 4 | 3 | | 5 | | 2 | | 5 | 5 | | 3 | 5 | |
| | 1 | 1 | 1 | 1 | 2 | 2 | 5 | 3 | 2 | 4 | | 3 | 5 | | 4 | 3 | 2 | | 5 | | 2 | | 4 | 4 | | 3 | 4 | |
| | 0.50 | 1 | 1 | 1 | 2 | 1 | 5 | 2 | 2 | 2 | | 3 | 5 | | 5 | 3 | 3 | | 4 | | 1 | | 4 | 5 | | 3 | 5 | |
| 35 | 8 | | | | | | | | | 2 | | 1 | | | 3 | 3 | 4 | | 2 | | 2 | | 4 | | | 2 | 2 | |
| | 4 | 1 | 1 | 1 | 1 | 3 | 2 | 1 | 2 | 1 | | 1 | 1 | | 1 | 2 | 3 | | 1 | | 1 | | 2 | 1 | | 1 | 1 | |
| | 2 | 1 | 1 | 1 | 1 | 2 | 1 | 1 | 1 | 1 | | 1 | 1 | | 1 | 1 | 3 | | 1 | | 1 | | 1 | 1 | | 1 | 1 | |
| | 1 | 1 | 1 | 1 | 1 | 1 | 1 | 1 | 1 | 1 | | 1 | 1 | | 1 | 1 | 1 | | 1 | | 1 | | 1 | 1 | | 1 | 1 | |
| 36 | 8 | | | | | | | | | 5 | | 5 | | | 5 | 5 | 5 | | 5 | | 5 | | 5 | | | 5 | 5 | |
| | 4 | 4 | 5 | 4 | 5 | 5 | 5 | 4 | 5 | 5 | | 5 | 5 | | 5 | 5 | 5 | | 5 | | 5 | | 5 | 5 | | 5 | 5 | |
| | 2 | 3 | 3 | 4 | 5 | 5 | 5 | 3 | 5 | 5 | | 5 | 5 | | 5 | 5 | 5 | | 5 | | 4 | | 5 | 5 | | 5 | 5 | |
| | 1 | 2 | 2 | 2 | 4 | 5 | 5 | 4 | 5 | 5 | | 5 | 5 | | 5 | 5 | 5 | | 5 | | 4 | | 5 | 5 | | 5 | 5 | |
| | 1 | 2 | 1 | 3 | 4 | 5 | 5 | 5 | 5 | 5 | | 5 | 5 | | 5 | 4 | 5 | | 5 | | 4 | | 5 | 5 | | 4 | 5 | |
| | 0.50 | 2 | 1 | 2 | 2 | | 5 | 2 | | 5 | 1 | | 5 | | 5 | 5 | 5 | | 5 | | 3 | | 5 | 5 | | 4 | | |
| | 0.50 | 2 | 2 | 2 | 2 | 4 | 5 | 3 | 5 | 4 | | 5 | 5 | | 5 | 4 | 5 | | 5 | | 4 | | 5 | 5 | | 4 | 5 | |
| | 0.25 | 1 | 1 | 1 | 2 | | 5 | 1 | | 2 | 1 | | | 5 | 4 | 2 | 5 | | 5 | | 3 | | 4 | 3 | | 2 | | |
| | 0.25 | 1 | 2 | 1 | 2 | 1 | 5 | 3 | 4 | 2 | | 3 | 5 | | 5 | 4 | 5 | | 5 | | 4 | | 3 | 4 | | 3 | 5 | |
| | 0.125 | 1 | 1 | 1 | 1 | | 5 | 1 | | 2 | 1 | | | 5 | 4 | 2 | 5 | | 5 | | 1 | | 1 | 3 | | 2 | | |
| | 0.062 | 1 | 1 | 1 | 1 | | 4 | 1 | | 1 | 1 | | | 5 | 1 | 1 | 5 | | 1 | | 1 | | 1 | 1 | | 1 | | |
| 37 | 8 | | | | | | | | | 5 | | 4 | | | 5 | 5 | 5 | | 5 | | 5 | | 5 | | | 5 | 5 | |
| | 4 | 3 | 5 | 5 | 5 | 5 | 5 | 4 | 5 | 5 | | 5 | 5 | | 5 | 5 | 5 | | 5 | | 5 | | 5 | 5 | | 5 | 5 | |
| | 2 | 3 | 2 | 3 | 5 | 5 | 5 | 4 | 5 | 5 | | 5 | 5 | | 5 | 5 | 5 | | 5 | | 5 | | 5 | 5 | | 5 | 5 | |
| | 1 | 3 | 2 | 1 | 2 | 4 | 5 | 4 | 4 | 3 | | 5 | 5 | | 5 | 2 | 5 | | 5 | | 4 | | 5 | 4 | | 4 | 5 | |
| | 1 | 2 | 1 | 2 | 4 | 5 | 5 | 4 | 5 | 5 | | 5 | 5 | | 5 | 5 | 5 | | 5 | | 2 | | 5 | 5 | | 5 | 5 | |
| | 0.50 | 1 | 1 | 2 | 3 | 3 | 5 | 3 | 3 | 3 | | 5 | 5 | | 5 | 4 | 5 | | 5 | | 2 | | 5 | 3 | | 5 | 5 | |
| | 0.25 | 1 | 1 | 1 | 2 | 1 | 4 | 1 | 4 | 3 | | 3 | 5 | | 5 | 2 | 5 | | 5 | | 1 | | 4 | 2 | | 2 | 3 | |
| 38 | 8 | | | | | | | | | 5 | | 4 | | | 5 | 5 | 5 | | 5 | | 4 | | 5 | | | 4 | 5 | |
| | 4 | 4 | 5 | 5 | 5 | 5 | 5 | 5 | 5 | 5 | | 5 | 5 | | 5 | 5 | 5 | | 5 | | 5 | | 5 | 5 | | 5 | 5 | |
| | 2 | 3 | 4 | 5 | 5 | 5 | 5 | 5 | 5 | 5 | | 5 | 5 | | 5 | 5 | 5 | | 5 | | 5 | | 5 | 5 | | 5 | 5 | |
| | 1 | 3 | 2 | 4 | 3 | | 5 | 4 | | | | 3 | | | 5 | 5 | 5 | | 5 | | 3 | | 5 | 4 | | 5 | 5 | |
| | 1 | 2 | 3 | 4 | 4 | 5 | 5 | 4 | 5 | 5 | | 5 | 5 | | 5 | 5 | 5 | | 5 | | 5 | | 5 | 5 | | 5 | 5 | |
| | 0.50 | 1 | 2 | 1 | 2 | | 5 | 3 | | | | 3 | | | 5 | 5 | 5 | | 5 | | 1 | | 4 | 3 | | 5 | 4 | |
| | 0.25 | 1 | 1 | 1 | 1 | | 5 | 2 | | | | 1 | | | 3 | 3 | 4 | | 4 | | 1 | | 2 | 3 | | 2 | 2 | |
| 39 | 8 | | | | | | | | | 1 | | 1 | | | 2 | 3 | 4 | | 4 | | 1 | | 4 | | | 2 | 4 | |
| | 4 | 1 | 1 | 1 | 1 | 1 | 1 | 1 | 1 | 1 | | 1 | 1 | | 1 | 1 | 1 | | 1 | | 1 | | 1 | 1 | | 1 | 1 | |
| | 2 | 1 | 1 | 1 | 1 | 1 | 1 | 1 | 1 | 1 | | 1 | 1 | | 1 | 1 | 1 | | 1 | | 1 | | 1 | 1 | | 1 | 1 | |
| | 1 | 1 | 1 | 1 | 1 | 1 | 1 | 1 | 1 | 1 | | 1 | 1 | | 1 | 1 | 1 | | 1 | | 1 | | 1 | 1 | | 1 | 1 | |
| 40 | 8 | | | | | | | | | 5 | | 5 | | | 5 | 5 | 5 | | 5 | | 5 | | 5 | | | 5 | 5 | |
| | 4 | 4 | 4 | 5 | 5 | 5 | 5 | 5 | 5 | 5 | | 5 | 5 | | 5 | 5 | 5 | | 5 | | 5 | | 5 | 5 | | 5 | 5 | |
| | 2 | 4 | 3 | 5 | 4 | 5 | 5 | 5 | 5 | 5 | | 5 | 5 | | 5 | 5 | 5 | | 5 | | 5 | | 5 | 5 | | 5 | 5 | |
| | 1 | 2 | 2 | 3 | 4 | 5 | 5 | 5 | 5 | 5 | | 5 | 5 | | 5 | 4 | 5 | | 5 | | 5 | | 5 | 5 | | 5 | 5 | |
| | 1 | 2 | 2 | 3 | 2 | 4 | 5 | 2 | 4 | 5 | | 5 | 5 | | 5 | 5 | 5 | | 5 | | 2 | | 5 | 4 | | 5 | 5 | |
| | 0.50 | 2 | 1 | 1 | 1 | 3 | 5 | 2 | 3 | 3 | | 4 | 5 | | 5 | 5 | 5 | | 5 | | 2 | | 5 | 4 | | 3 | 5 | |
| | 0.25 | 1 | 1 | 2 | 1 | 4 | 5 | 2 | 4 | 2 | | 4 | 5 | | 4 | 2 | 4 | | 5 | | 1 | | 4 | 1 | | 2 | 4 | |
| 41 | 8 | | | | | | | | | 5 | | 4 | | | 5 | 5 | 5 | | 5 | | 3 | | 5 | | | 5 | 5 | |
| | 4 | 4 | 2 | 4 | 5 | 5 | 5 | 5 | 5 | 5 | | 5 | 5 | | 5 | 5 | 5 | | 5 | | 5 | | 5 | 5 | | 5 | 5 | |
| | 2 | 3 | 1 | 2 | 3 | 5 | 5 | 5 | 5 | 5 | | 5 | 5 | | 5 | 3 | 5 | | 5 | | 5 | | 5 | 5 | | 5 | 5 | |
| | 1 | 2 | 2 | 2 | 3 | 5 | 5 | 5 | 5 | 4 | | 5 | 5 | | 5 | 3 | 5 | | 5 | | 4 | | 5 | 5 | | 5 | 5 | |
| | 0.50 | 2 | 1 | 1 | 2 | | 5 | 3 | | 2 | 1 | | | 5 | 5 | 4 | 5 | | 5 | | 2 | | 3 | 5 | | 4 | | |
| | 0.25 | 1 | 1 | 1 | 1 | | 4 | 1 | | 1 | 1 | | | 2 | 1 | 3 | 1 | | 2 | | 1 | | 1 | 1 | | 1 | | |
| | 0.125 | 1 | 1 | 1 | 1 | | 3 | 1 | | 1 | 1 | | | 1 | 1 | 3 | 1 | | 1 | | 1 | | 1 | 1 | | 1 | | |
| 42 | 8 | | | | | | | | | 5 | | 5 | | | 5 | 5 | 5 | | 5 | | 4 | | 5 | | | 5 | 5 | 5 |
| | 4 | 3 | 2 | 2 | 4 | 5 | 5 | 5 | 5 | 5 | | 5 | 5 | | 5 | 5 | 5 | | 5 | | 5 | | 5 | 5 | | 5 | 5 | 5 |
| | 2 | 2 | 2 | 3 | 4 | 5 | 5 | 5 | 5 | 5 | | 5 | 5 | | 5 | 5 | 5 | | 5 | | 3 | | 5 | 5 | | 4 | 5 | 5 |
| | 1 | 1 | 2 | 3 | 3 | 4 | 5 | 5 | 5 | 5 | | 5 | 5 | | 5 | 4 | 5 | | 5 | | 4 | | 5 | 5 | | 4 | 5 | 5 |
| | 0.50 | 3 | 1 | 1 | 1 | | 5 | 3 | | 4 | 1 | | | 5 | 3 | 3 | 2 | | 5 | | 1 | | 3 | 1 | | 3 | | |
| | 0.25 | 1 | 1 | 1 | 1 | | 5 | 1 | | 2 | 1 | | | 5 | 1 | 2 | 4 | | 5 | | 1 | | 2 | 1 | | 1 | | |
| | 0.125 | 1 | 1 | 1 | 1 | | 4 | 1 | | 1 | 1 | | 4 | | 1 | 3 | 3 | | 2 | | 1 | | 2 | 1 | | 1 | | |
| | 0.062 | 1 | 1 | 1 | 1 | | 3 | 1 | | 1 | 1 | | 1 | | 1 | 3 | 3 | | 1 | | 1 | | 1 | 1 | | 1 | | |
| 43 | 8 | | | | | | | | | 5 | | 5 | | | 5 | 5 | 5 | | 5 | | 5 | | 5 | | | 5 | 5 | 5 |
| | 4 | 4 | 4 | 4 | 4 | 5 | 5 | 4 | 5 | 5 | | 5 | 5 | | 5 | 5 | 5 | | 5 | | 5 | | 5 | 5 | | 5 | 5 | 5 |
| | 2 | 4 | 3 | 3 | 3 | 4 | 5 | 4 | 5 | 5 | | 5 | 5 | | 5 | 5 | 5 | | 5 | | 5 | | 5 | 5 | | 5 | 5 | |

TABLE III-continued

| | | PLANT SPECIES Preemergence | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Ex. No. | Rate lbs/A | A | B | C | D | E | F | G | H | I | J | K | L | M | N | O | P | Q | R | S | T | U | V | W | X | Y | Z | a |
| | 1 | 2 | 3 | 3 | 3 | 3 | 5 | 3 | 3 | 3 | | 4 | 5 | | 5 | 5 | 5 | | | 5 | | 2 | | 5 | 4 | | 5 | 5 |
| | 0.50 | 1 | 1 | 1 | 1 | | 5 | 1 | | 2 | 1 | | 5 | | 4 | 3 | 5 | | | 4 | | 1 | | 1 | 2 | | 3 | |
| | 0.25 | 1 | 1 | 1 | 1 | | 5 | 1 | | 1 | 1 | | 5 | | 3 | 2 | 4 | | | 3 | | 1 | | 1 | 1 | | 3 | |
| | 0.125 | 1 | 1 | 1 | 1 | | 4 | 1 | | 1 | 1 | | 5 | | 2 | 2 | 3 | | | 3 | | 1 | | 1 | 1 | | 3 | |
| | 0.062 | 1 | 1 | 1 | 1 | | 2 | 1 | | 1 | 1 | | 1 | | 1 | 1 | 1 | | | 1 | | 1 | | 1 | 1 | | 1 | |
| 44 | 8 | | | | | | | | | 5 | | 5 | | | 5 | 5 | 5 | | | 5 | | 5 | | 5 | | | 5 | 5 |
| | 4 | 2 | 4 | 4 | 2 | 5 | 5 | 3 | 4 | 5 | | 5 | 5 | | 5 | 5 | 5 | | | 5 | | 2 | | 4 | 4 | | 5 | 5 |
| | 2 | 2 | 3 | 3 | 3 | 5 | 5 | 3 | 4 | 3 | | 4 | 5 | | 5 | 5 | 5 | | | 5 | | 2 | | 5 | 4 | | 3 | 5 |
| | 1 | 1 | 1 | 1 | 3 | 4 | 5 | 1 | 3 | 2 | | 2 | 5 | | 3 | 3 | 5 | | | 4 | | 1 | | 5 | 3 | | 3 | 5 |
| | 1 | 1 | 1 | 1 | 1 | 4 | 5 | 1 | 2 | 3 | | 3 | 5 | | 5 | 5 | 5 | | | 5 | | 1 | | 5 | 3 | | 2 | 5 |
| | 0.50 | 1 | 1 | 1 | 2 | 1 | 5 | 1 | 1 | 1 | | 2 | 5 | | 3 | 4 | 5 | | | 3 | | 1 | | 4 | 3 | | 3 | 5 |
| | 0.25 | 1 | 1 | 1 | 1 | 1 | 2 | 1 | 1 | 1 | | 2 | 4 | | 3 | 3 | 5 | | | 3 | | 1 | | 3 | 2 | | 1 | 3 |
| 45 | 8 | | | | | | | | | 5 | | 5 | | | 5 | 5 | 5 | | | 5 | | 5 | | 5 | | | 5 | 5 |
| | 4 | 4 | 5 | 5 | 5 | 5 | 5 | 5 | 5 | 5 | | 5 | 5 | | 5 | 5 | 5 | | | 5 | | 5 | | 5 | 5 | | 5 | 5 |
| | 2 | 3 | 5 | 5 | 5 | 5 | 5 | 5 | 5 | 5 | | 5 | 5 | | 5 | 5 | 5 | | | 5 | | 5 | | 5 | 5 | | 5 | 5 |
| | 1 | 2 | 5 | 5 | 5 | 5 | 5 | 3 | 5 | 5 | | 5 | 5 | | 5 | 5 | 5 | | | 5 | | 4 | | 5 | 5 | | 5 | 5 |
| | 1 | 2 | 3 | 3 | 5 | 5 | 5 | 4 | 5 | 5 | | 5 | 5 | | 5 | 5 | 5 | | | 5 | | 5 | | 5 | 5 | | 5 | 5 |
| | 0.50 | 1 | 1 | 1 | 2 | 4 | 5 | 3 | 4 | 3 | | 4 | 5 | | 5 | 5 | 5 | | | 5 | | 3 | | 5 | 5 | | 5 | 5 |
| | 0.25 | 1 | 1 | 1 | 2 | 2 | 5 | 1 | 2 | 3 | | 3 | 5 | | 2 | 3 | 5 | | | 3 | | 1 | | 3 | 3 | | 2 | 4 |
| | 0.25 | 1 | 1 | 1 | 1 | 3 | 5 | 1 | 2 | 3 | | 5 | 5 | 3 | 5 | 5 | | 5 | | 2 | | | 4 | 3 | | 3 | 5 | |
| | 0.125 | 1 | 1 | 1 | 1 | 1 | 5 | 1 | 2 | 1 | | 1 | 2 | | 1 | 2 | 4 | | | 3 | | 1 | | 1 | 1 | | 1 | 1 |
| | 0.062 | 1 | 1 | 1 | 1 | 1 | 5 | 1 | 1 | 1 | | 1 | 1 | | 1 | 1 | 2 | | | 1 | | 1 | | 1 | 1 | | 1 | 1 |
| 46 | 8 | | | | | | | | | 5 | | 5 | | | 5 | 5 | 5 | | | 5 | | 4 | | 5 | | | 5 | 5 |
| | 4 | 2 | 3 | 2 | 2 | 5 | 5 | 5 | 5 | 5 | | 5 | 5 | | 5 | 5 | 5 | | | 5 | | 4 | | 5 | 5 | | 5 | 5 |
| | 2 | 2 | 3 | 1 | 3 | 5 | 5 | 4 | 5 | 5 | | 5 | 5 | | 5 | 5 | 5 | | | 5 | | 4 | | 5 | 5 | | 5 | 5 |
| | 1 | 2 | 1 | 1 | 2 | 4 | 5 | 3 | 3 | 5 | | 4 | 5 | | 5 | 5 | 5 | | | 5 | | 3 | | 5 | 5 | | 4 | 4 |
| | 1 | 1 | 2 | 3 | 3 | 5 | 5 | 4 | 4 | 5 | | 5 | 5 | | 5 | 5 | 5 | | | 5 | | 4 | | 5 | 5 | | 5 | 5 |
| | 0.50 | 1 | 1 | 1 | 1 | | 5 | 1 | | 2 | 1 | | 5 | | 4 | 4 | 5 | | | 5 | | 2 | | 5 | 2 | | 4 | |
| | 0.50 | 1 | 1 | 2 | 2 | 5 | 5 | 3 | 4 | 4 | | 4 | 5 | | 5 | 5 | 5 | | | 5 | | 2 | | 5 | 5 | | 4 | 5 |
| | 0.25 | 1 | 1 | 1 | 1 | | 5 | 1 | | 2 | 1 | | 4 | | 2 | 4 | 3 | | | 4 | | 1 | | 1 | 1 | | 4 | |
| | 0.125 | 1 | 1 | 1 | 1 | | 5 | 1 | | 1 | 1 | | 1 | | 1 | 2 | 1 | | | 3 | | 1 | | 1 | 1 | | 2 | |
| | 0.062 | 1 | 1 | 1 | 1 | | 4 | 1 | | 1 | 1 | | 1 | | 1 | 1 | 1 | | | 1 | | 1 | | 1 | 1 | | 1 | |
| 47 | 8 | | | | | | | | | 5 | | 4 | | | 5 | 5 | 5 | | | 5 | | 5 | | 5 | | | 5 | 5 |
| | 4 | 4 | 5 | 5 | 5 | 5 | 5 | 4 | 5 | 5 | | 5 | 5 | | 5 | 5 | 5 | | | 5 | | 5 | | 5 | 5 | | 5 | 5 |
| | 2 | 4 | 4 | 4 | 5 | 5 | 5 | 4 | 5 | 5 | | 5 | 5 | | 5 | 5 | 5 | | | 5 | | 5 | | 5 | 5 | | 5 | 5 |
| | 1 | 3 | 3 | 3 | 3 | 3 | 5 | 4 | 5 | 4 | | 5 | 5 | | 5 | 5 | 5 | | | 5 | | 5 | | 5 | 5 | | 5 | 5 |
| | 0.50 | 2 | 1 | 1 | 1 | | 5 | 1 | | 1 | 1 | | | 4 | | 3 | 2 | 3 | | | 2 | | 1 | | 1 | 2 | | 4 | |
| | 0.25 | 1 | 1 | 1 | 1 | | 5 | 1 | | 1 | 1 | | | 4 | | 2 | 2 | 3 | | | 2 | | 1 | | 1 | 2 | | 3 | |
| | 0.125 | 1 | 1 | 1 | 1 | | 4 | 1 | | 1 | 1 | | | 1 | | 1 | 2 | 3 | | | 1 | | 1 | | 1 | 1 | | 1 | |
| | 0.062 | 1 | 1 | 1 | 1 | | 2 | 1 | | 1 | 1 | | | 1 | | 1 | 1 | 1 | | | 1 | | 1 | | 1 | 1 | | 1 | |
| 48 | 8 | | | | | | | | | 5 | | 5 | | | 5 | 5 | 5 | | | 5 | | 5 | | 5 | | | 5 | 5 |
| | 4 | 5 | 5 | 4 | 5 | 5 | 4 | 5 | 5 | 5 | | 5 | 5 | | 5 | 5 | 5 | | | 5 | | 5 | | 5 | 5 | | 5 | 5 |
| | 2 | 2 | 1 | 3 | 2 | 3 | 5 | 4 | 4 | 4 | | 5 | 5 | | 5 | 3 | 5 | | | 5 | | 2 | | 5 | 4 | | 3 | 5 |
| | 1 | 1 | 1 | 2 | 3 | 5 | 5 | 3 | 5 | 3 | | 5 | 5 | | 5 | 5 | 5 | | | 5 | | 2 | | 5 | 3 | | 5 | 5 |
| 49 | 8 | | | 5 | | | | | | 5 | 3 | | | | 5 | 5 | 5 | | | 5 | | | | | | | 5 | |
| | 4 | 2 | 1 | 3 | 3 | | 5 | 3 | | 5 | 2 | | 5 | | 5 | 5 | 5 | | | 5 | | 5 | | 5 | 5 | | 5 | |
| | 1 | 1 | 1 | 1 | 1 | | 5 | 1 | | 2 | 1 | | 5 | | 4 | 3 | 3 | | | 3 | | 1 | | 1 | 1 | | 2 | |
| | 0.50 | 1 | 1 | 1 | 1 | | 5 | 1 | | 1 | 1 | | 3 | | 4 | 2 | 3 | | | 2 | | 2 | | 1 | 1 | | 2 | |
| 50 | 8 | | | 5 | | | | | | 5 | 5 | | | | 5 | 5 | 5 | | | 5 | | | | | | | 5 | |
| | 4 | 3 | 4 | 5 | 3 | | 5 | 3 | | 5 | 2 | | 5 | | 5 | 5 | 5 | | | 5 | | 5 | | 5 | 5 | | 5 | |
| | 2 | 3 | 4 | 5 | 3 | | 5 | 4 | | 5 | 2 | | 5 | | 5 | 5 | 5 | | | 5 | | 5 | | 5 | 5 | | 5 | |
| | 1 | 2 | 3 | 3 | 3 | | 5 | 3 | | 5 | 1 | | 5 | | 5 | 5 | 5 | | | 5 | | 5 | | 5 | 5 | | 5 | |
| | 0.50 | 2 | 2 | 2 | 2 | | 5 | 2 | | 5 | 1 | | 5 | | 5 | 5 | 5 | | | 5 | | 5 | | 5 | 5 | | 5 | |
| 51 | 8 | | | 5 | | | | | | 5 | 2 | | | | 5 | 5 | 5 | | | 5 | | | | | | | 5 | |
| | 4 | 4 | 5 | 5 | 3 | | 5 | 5 | | 5 | 2 | | 5 | | 5 | 5 | 5 | | | 5 | | 4 | | 5 | 5 | | 5 | |
| | 2 | 4 | 5 | 5 | 3 | | 5 | 5 | | 5 | 2 | | 5 | | 5 | 5 | 5 | | | 5 | | 3 | | 5 | 5 | | 5 | |
| | 1 | 4 | 3 | 3 | 2 | | 5 | 3 | | 4 | 1 | | 5 | | 5 | 5 | 5 | | | 5 | | 3 | | 5 | 5 | | 5 | |
| | 0.50 | 3 | 1 | 3 | 2 | | 5 | 1 | | 4 | 1 | | 5 | | 5 | 5 | 5 | | | 5 | | 3 | | 4 | 5 | | 4 | |
| 52 | 8 | | | 5 | | | | | | 5 | 2 | | | | 5 | 5 | 5 | | | 5 | | | | | | | 5 | |
| | 4 | 4 | 3 | 5 | 4 | | 5 | 4 | | 5 | 3 | | 5 | | 5 | 5 | 5 | | | 5 | | 5 | | 5 | 5 | | 5 | |
| | 2 | 4 | 4 | 5 | 4 | | 5 | 4 | | 5 | 2 | | 5 | | 5 | 5 | 5 | | | 5 | | 5 | | 5 | 5 | | 5 | |
| | 1 | 4 | 3 | 4 | 3 | | 5 | 4 | | 5 | 1 | | 5 | | 5 | 5 | 5 | | | 5 | | 3 | | 5 | 5 | | 4 | |
| | 0.50 | 3 | 1 | 3 | 2 | | 5 | 3 | | 5 | 1 | | 5 | | 5 | 5 | 5 | | | 5 | | 2 | | 5 | 5 | | 4 | |
| 53 | 8 | | | 4 | | | | | | 5 | 2 | | | | 5 | 5 | 5 | | | 5 | | | | | | | 5 | |
| | 4 | 4 | 4 | 5 | 4 | | 5 | 4 | | 5 | 3 | | 5 | | 5 | 5 | 5 | | | 5 | | 3 | | 5 | 5 | | 4 | |
| | 2 | 4 | 4 | 4 | 3 | | 5 | 4 | | 5 | 2 | | 5 | | 5 | 5 | 5 | | | 5 | | 3 | | 5 | 5 | | 4 | |
| | 1 | 3 | 3 | 3 | 2 | | 5 | 3 | | 4 | 1 | | 5 | | 5 | 5 | 5 | | | 5 | | 3 | | 4 | 5 | | 4 | |
| | 0.50 | 2 | 1 | 2 | 2 | | 5 | 1 | | 3 | 1 | | 5 | | 4 | 5 | 5 | | | 5 | | 2 | | 3 | 5 | | 4 | |
| 54 | 8 | | | | | | | | | 5 | | 5 | | | 5 | 5 | 5 | | | 5 | | 5 | | 5 | | | 5 | 5 |
| | 4 | 4 | 3 | 4 | 4 | 5 | 5 | 5 | 5 | 5 | | 5 | 5 | | 5 | 5 | 5 | | | 5 | | 3 | | 5 | 5 | | 5 | 5 |
| | 2 | 2 | 1 | 2 | 4 | 5 | 5 | 4 | 5 | 5 | | 5 | 5 | | 5 | 5 | 5 | | | 5 | | 3 | | 5 | 5 | | 5 | 5 |
| | 1 | 2 | 1 | 1 | 3 | 5 | 5 | 3 | 3 | 5 | | 5 | 5 | | 5 | 5 | 5 | | | 5 | | 2 | | 5 | 5 | | 4 | 5 |
| | 1 | 1 | 1 | 2 | 3 | 5 | 5 | 3 | 4 | 4 | | 5 | 5 | | 5 | 5 | 5 | | | 5 | | 2 | | 5 | 5 | | 5 | 5 |
| | 0.50 | 1 | 1 | 1 | 2 | 5 | 5 | 2 | 2 | 3 | | 3 | 5 | | 5 | 5 | 5 | | | 5 | | 2 | | 4 | 4 | | 3 | 5 |
| | 0.25 | 1 | 1 | 1 | 1 | 3 | 2 | 1 | 1 | 1 | | 2 | 4 | | 1 | 2 | 4 | | | 4 | | 1 | | 1 | 1 | | 1 | 1 |
| 55 | 8 | | | | | | | | | 5 | | 5 | | | 5 | 5 | 5 | | | 5 | | 5 | | 5 | | | 5 | 5 |
| | 4 | 2 | 2 | 4 | 4 | 5 | 5 | 5 | 5 | 5 | | 5 | 5 | | 5 | 5 | 5 | | | 5 | | 5 | | 5 | 5 | | 5 | 5 |
| | 2 | 2 | 1 | 2 | 3 | 5 | 5 | 4 | 5 | 5 | | 5 | 5 | | 5 | 5 | 5 | | | 5 | | 5 | | 5 | 5 | | 5 | 5 |

TABLE III-continued

PLANT SPECIES
Preemergence

| Ex. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| | 1 | 1 | 2 | 1 | 2 | 5 | 5 | 3 | 2 | 4 | | 4 | 5 | | 5 | 5 | 5 | | | 5 | | 2 | | 5 | 5 | | 3 | 5 |
| | 1 | 1 | 1 | 1 | 2 | 4 | 5 | 2 | 3 | 3 | | 3 | 5 | | 5 | 5 | 5 | | | 5 | | 5 | | 5 | 5 | | 5 | 5 |
| | 0.50 | 1 | 1 | 1 | 2 | 5 | 5 | 1 | 2 | 3 | | 4 | 5 | | 5 | 5 | 5 | | | 5 | | 2 | | 4 | 3 | | 2 | 3 |
| | 0.25 | 1 | 1 | 1 | 1 | 5 | 5 | 1 | 1 | 1 | | 2 | 5 | | 3 | 4 | 4 | | | 4 | | 2 | | 3 | 3 | | 2 | 3 |
| | 0.25 | 1 | 1 | 1 | 1 | 3 | 3 | 1 | 1 | 1 | | 4 | 5 | | 3 | 1 | 5 | | | 3 | | 1 | | 4 | 3 | | 2 | 4 |
| | 0.125 | 1 | 1 | 1 | 1 | 1 | 3 | 1 | 1 | 1 | | 1 | 5 | | 1 | 1 | 4 | | | 2 | | 1 | | 2 | 2 | | 1 | 1 |
| | 0.062 | 1 | 1 | 1 | 1 | 1 | 1 | 1 | 1 | 1 | | 1 | 5 | | 1 | 1 | 4 | | | 1 | | 1 | | 1 | | | 1 | 1 |
| 56 | 8 | | | | | | | | | 5 | | 4 | | 5 | 5 | 5 | | | 5 | | 4 | | 5 | | | 5 | 5 | |
| | 4 | 4 | 3 | 4 | 4 | 5 | 5 | 5 | 5 | 5 | | 5 | 5 | | 5 | 5 | 5 | | | 5 | | 4 | | 5 | 5 | | 5 | 5 |
| | 2 | 3 | 2 | 3 | 4 | 5 | 5 | 5 | 5 | 5 | | 5 | 5 | | 5 | 5 | 5 | | | 5 | | 3 | | 4 | 5 | | 4 | 5 |
| | 1 | 3 | 2 | 1 | 4 | 5 | 5 | 4 | 4 | 4 | | 5 | 5 | | 5 | 5 | 5 | | | 5 | | 2 | | 5 | 5 | | 5 | 5 |
| | 1 | 1 | 1 | 2 | 3 | 5 | 5 | 4 | 3 | 5 | | 5 | 5 | | 5 | 5 | 5 | | | 5 | | 2 | | 5 | 5 | | 5 | 5 |
| | 0.50 | 1 | 1 | 1 | 2 | 5 | 5 | 2 | 2 | 3 | | 4 | 5 | | 4 | 4 | 5 | | | 5 | | 2 | | 5 | 5 | | 3 | 5 |
| | 0.25 | 1 | 1 | 1 | 1 | 3 | 4 | 1 | 2 | 1 | | 2 | 5 | | 1 | 3 | 5 | | | 2 | | 2 | | 2 | 4 | | 1 | 2 |
| 57 | 8 | | | | | | | | | 5 | | 4 | | | 5 | 5 | 5 | | | 5 | | 4 | 5 | | | | 5 | 5 |
| | 4 | 3 | 5 | 4 | 5 | 5 | 5 | 5 | 5 | 5 | | 5 | 5 | | 5 | 5 | 5 | | | 5 | | 5 | | 5 | 5 | | 5 | 5 |
| | 2 | 3 | 5 | 4 | 5 | 5 | 5 | 5 | 5 | 5 | | 5 | 5 | | 5 | 5 | 5 | | | 5 | | 5 | | 5 | 5 | | 5 | 5 |
| | 1 | 1 | 4 | 2 | 5 | 5 | 5 | 5 | 5 | 5 | | 4 | 5 | | 5 | 5 | 5 | | | 5 | | 4 | | 5 | 5 | | 5 | 5 |
| | 1 | 1 | 2 | 2 | 3 | 5 | 5 | 4 | 5 | 4 | | 4 | 5 | | 5 | 5 | 5 | | | 5 | | 5 | | 5 | 5 | | 5 | 5 |
| | 0.50 | 1 | 1 | 1 | 2 | 4 | 5 | 3 | 5 | 3 | | 3 | 5 | | 5 | 5 | 4 | | | 4 | | 2 | | 4 | 4 | | 3 | 5 |
| | 0.25 | 1 | 1 | 1 | 2 | 2 | 4 | 2 | 3 | 1 | | 1 | 5 | | 3 | 4 | 3 | | | 2 | | 1 | | 4 | 2 | | 1 | 5 |
| 58 | 8 | | | 5 | | | | | | 5 | 4 | | | | 5 | 5 | 5 | | | 5 | | | | | | | 5 | |
| | 4 | 3 | 4 | 5 | 4 | | 5 | 4 | | 5 | 3 | | 5 | | 5 | 5 | 5 | | | 5 | | 4 | | 5 | 5 | | 5 | |
| | 2 | 3 | 1 | 2 | 3 | | 5 | 4 | | 4 | 2 | | 5 | | 5 | 5 | 5 | | | 5 | | 4 | | 5 | 5 | | 5 | |
| | 1 | 3 | 2 | 3 | 3 | | 5 | 2 | | 4 | 2 | | 5 | | 5 | 5 | 5 | | | 5 | | 3 | | 5 | 5 | | 5 | |
| | 0.50 | 2 | 1 | 2 | 1 | | 5 | 1 | | 2 | 1 | | 5 | | 5 | 5 | 5 | | | 5 | | 2 | | 5 | 4 | | 4 | |
| 59 | 8 | | | 5 | | | | | | 5 | 3 | | | | 5 | 5 | 5 | | | 5 | | | | | | | 5 | |
| | 4 | 4 | 4 | 4 | 3 | | 5 | 4 | | 5 | 2 | | 5 | | 5 | 5 | 5 | | | 5 | | 5 | | 5 | 5 | | 5 | |
| | 2 | 4 | 4 | 3 | 3 | | 5 | 4 | | 5 | 2 | | 5 | | 5 | 5 | 5 | | | 5 | | 5 | | 5 | 5 | | 5 | |
| | 1 | 3 | 1 | 2 | 2 | | 5 | 4 | | ·5 | 1 | | 5 | | 5 | 5 | 5 | | | 5 | | 5 | | 4 | 5 | | 4 | |
| | 0.50 | 1 | 1 | 1 | 1 | | 5 | 1 | | 4 | 1 | | 5 | | 5 | 5 | 5 | | | 5 | | 4 | | 4 | 5 | | 4 | |
| 60 | 8 | | | 5 | | | | | | 5 | 3 | | | | 5 | 5 | 5 | | | 5 | | | | | | | 5 | |
| | 4 | 3 | 5 | 5 | 3 | | | 4 | | 5 | 2 | | 5 | | 5 | 5 | 5 | | | 5 | | 4 | | 5 | 5 | | 5 | |
| | 2 | 2 | 4 | 4 | 3 | | 5 | 3 | | 5 | 2 | | 5 | | 5 | 5 | 5 | | | 5 | | 4 | | 5 | 4 | | 5 | |
| | 1 | 1 | 3 | 4 | 1 | | 5 | 1 | | 4 | 1 | | 5 | | 5 | 5 | 5 | | | 4 | | 3 | | 5 | 4 | | 5 | |
| | 0.50 | 1 | 2 | 1 | 1 | | 5 | 1 | | 3 | 1 | | 5 | | 5 | 5 | 5 | | | 4 | | 2 | | 5 | 2 | | 2 | |

TABLE IV

PLANT SPECIES
Postemergence

| Ex. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 34 | 2 | | | | | | | | | 5 | | 3 | | | 3 | 4 | 3 | | | 3 | | 1 | | 2 | | | 3 | 4 |
| | 1 | | | | | | | | | 5 | | 2 | | | 2 | 3 | 2 | | | 2 | | 1 | | 2 | | | 3 | 5 |
| | 0.50 | | | | | | | | | 4 | | 2 | | | 2 | 3 | 2 | | | 2 | | 2 | | 2 | | | 3 | 4 |
| 35 | 8 | | | | | | | | | 2 | | 1 | | | 1 | 2 | 3 | | | 1 | | 1 | | 3 | | | 2 | 2 |
| 36 | 8 | | | | | | | | | 5 | | 5 | | | 5 | 5 | 5 | | | 5 | | 5 | | 5 | | | 5 | 5 |
| | 4 | | | | | | | | | 5 | | 5 | | | 5 | 5 | 5 | | | 5 | | 5 | | 5 | | | 5 | 5 |
| | 2 | | | | | | | | | 5 | | 5 | | | 5 | 5 | 5 | | | 5 | | 4 | | 5 | | | 5 | 5 |
| | 1 | | | | | | | | | 5 | | 4 | | | 4 | 5 | 5 | | | 4 | | 4 | | 5 | | | 5 | 5 |
| | 1 | | | | | | | | | 5 | | 5 | | | 5 | 5 | 5 | | | 5 | | 4 | | 5 | | | 5 | |
| | 0.50 | 4 | 5 | 4 | 3 | | 5 | 3 | | 5 | 3 | | 5 | | 5 | 5 | 3 | | | 5 | | 4 | | 5 | 5 | | 5 | |
| | 0.50 | | | | | | | | | 5 | | 5 | | | 3 | 5 | 3 | | | 5 | | 4 | | 5 | | | 5 | 5 |
| | 0.25 | 3 | 5 | 4 | 3 | | 4 | 2 | | 5 | 2 | | 5 | | 3 | 5 | 2 | | | 5 | | 4 | | 4 | 5 | | 5 | |
| | 0.25 | | | | | | | | | 5 | | 4 | | | 3 | 5 | 3 | | | 5 | | 3 | | 5 | | | 4 | 5 |
| | 0.125 | 2 | 3 | 3 | 2 | | 4 | 2 | | 5 | 2 | | 5 | | 2 | 4 | 2 | | | 5 | | 3 | | 3 | 5 | | 5 | |
| | 0.062 | 2 | 2 | 2 | 2 | | 4 | 2 | | 5 | 2 | | 5 | | 2 | 3 | 2 | | | 5 | | 2 | | 2 | 5 | | 3 | |
| 37 | 8 | | | | | | | | | 4 | | 5 | | | 5 | 5 | 5 | | | 5 | | 4 | | 5 | | | 5 | 5 |
| | 4 | | | | | | | | | 5 | | 5 | | | 4 | 5 | 5 | | | 5 | | 3 | | 5 | | | 4 | 5 |
| | 2 | | | | | | | | | 5 | | 5 | | | 4 | 5 | 5 | | | 4 | | 2 | | 5 | | | 5 | 5 |
| | 1 | | | | | | | | | 5 | | 5 | | | 4 | 5 | 4 | | | 4 | | 4 | | 5 | | | 4 | 5 |
| | 1 | | | | | | | | | 5 | | 4 | | | 3 | 5 | 5 | | | 5 | | 3 | | 4 | | | 5 | 5 |
| | 0.50 | | | | | | | | | 5 | | 4 | | | 3 | 5 | 4 | | | 5 | | 2 | | 4 | | | 4 | 5 |
| | 0.25 | | | | | | | | | 5 | | 2 | | | 2 | 5 | 3 | | | 5 | | 2 | | 3 | | | 3 | 5 |
| 38 | 8 | | | | | | | | | 5 | | 5 | | | 5 | 5 | 5 | | | 5 | | 4 | | 5 | | | 5 | 5 |
| | 4 | | | | | | | | | 5 | | 3 | | | 5 | 5 | 5 | | | 4 | | 2 | | 5 | | | 5 | 5 |
| | 2 | | | | | | | | | 5 | | 3 | | | 4 | 5 | 5 | | | 4 | | 2 | | 4 | | | 5 | 5 |
| | 1 | | | | | | | | | 5 | | 5 | | | 4 | 5 | 4 | | | 5 | | 4 | | 5 | | | 5 | 5 |
| | 1 | | | | | | | | | 5 | | 4 | | | 3 | 5 | 3 | | | 5 | | 2 | | 5 | | | 5 | 5 |
| | 0.50 | 4 | 5 | 4 | 4 | | 5 | 3 | | 5 | 4 | | 5 | | 4 | 4 | 3 | | | 5 | | 4 | | 5 | 5 | | 5 | |
| | 0.50 | | | | | | | | | 5 | | 4 | | | 3 | 5 | 3 | | | 5 | | 4 | | 5 | | | 5 | 5 |
| | 0.25 | 3 | 5 | 4 | 4 | | 5 | 3 | | 5 | 3 | | 5 | | 3 | 4 | 2 | | | 5 | | 3 | | 5 | 5 | | 4 | |
| | 0.25 | | | | | | | | | 5 | | 4 | | | 3 | 5 | 3 | | | 4 | | 4 | | 4 | | | 4 | 5 |
| | 0.125 | 3 | 4 | 3 | 3 | | 4 | 3 | | 5 | 2 | | 4 | | 2 | 4 | 1 | | | 4 | | 2 | | 3 | 4 | | 4 | |
| | 0.062 | 2 | 2 | 2 | 2 | | 4 | 2 | | 5 | 2 | | 4 | | 1 | 3 | 0 | | | 3 | | 2 | | 2 | 3 | | 3 | |
| 39 | 8 | | | | | | | | | 1 | | 1 | | | 1 | 1 | 1 | | | 1 | | 1 | | 1 | | | 1 | 1 |

TABLE IV-continued

| Ex. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 40 | 8 | | | | | | | | | 5 | | 4 | | | 4 | 5 | 5 | | | 5 | | 2 | 4 | | | | 3 | 5 |
| | 4 | | | | | | | | | 5 | | 5 | | | 3 | 5 | 4 | | | 5 | | 3 | 4 | | | | 4 | 5 |
| | 2 | | | | | | | | | 5 | | 5 | | | 3 | 5 | 2 | | | 5 | | 2 | 3 | | | | 4 | 5 |
| | 1 | | | | | | | | | 5 | | 5 | | | 2 | 5 | 2 | | | 4 | | 2 | 3 | | | | 5 | 5 |
| | 1 | | | | | | | | | 5 | | 3 | | | 5 | 5 | 5 | | | 5 | | 4 | 4 | | | | 4 | 5 |
| | 0.50 | | | | | | | | | 5 | | 4 | | | 4 | 5 | 4 | | | 5 | | 3 | 3 | | | | 5 | 5 |
| | 0.25 | | | | | | | | | 5 | | 3 | | | 4 | 5 | 4 | | | 5 | | 3 | 3 | | | | 4 | 5 |
| 41 | 8 | | | | | | | | | 4 | | 3 | | | 2 | 5 | 5 | | | 3 | | 2 | 2 | | | | 4 | 3 |
| | 4 | | | | | | | | | 3 | | 2 | | | 2 | 4 | 4 | | | 5 | | 1 | 3 | | | | 2 | 4 |
| | 2 | | | | | | | | | 1 | | 1 | | | 2 | 4 | 3 | | | 3 | | 1 | 2 | | | | 2 | 3 |
| | 1 | | | | | | | | | 1 | | 1 | | | 2 | 4 | 3 | | | 3 | | 1 | 1 | | | | 1 | 2 |
| 42 | 8 | | | | | | | | | 5 | | 3 | | | 1 | 5 | 4 | | | 2 | | 1 | 2 | | | | 3 | 3 |
| | 4 | | | | | | | | | 1 | | 1 | | | 2 | 4 | 3 | | | 3 | | 1 | 1 | | | | 1 | 1 |
| | 2 | | | | | | | | | 1 | | 1 | | | 1 | 1 | 1 | | | 1 | | 1 | 1 | | | | 1 | 1 |
| | 1 | | | | | | | | | 1 | | 1 | | | 1 | 1 | 1 | | | 1 | | 1 | 1 | | | | 1 | 1 |
| 43 | 8 | | | | | | | | | 5 | | 5 | | | 5 | 5 | 5 | | | 5 | | 5 | 5 | | | | 5 | 5 |
| | 4 | | | | | | | | | 5 | | 5 | | | 5 | 5 | 5 | | | 5 | | 5 | 5 | | | | 5 | 5 |
| | 2 | | | | | | | | | 5 | | 5 | | | 5 | 5 | 5 | | | 5 | | 5 | 5 | | | | 5 | 5 |
| | 1 | | | | | | | | | 5 | | 5 | | | 4 | 4 | 3 | | | 5 | | 5 | 5 | | | | 5 | 5 |
| | 0.50 | 3 | 5 | 5 | 3 | | 4 | 3 | | 5 | 3 | | 5 | | 4 | 5 | 3 | | | 5 | | 3 | 4 | | 5 | | 5 | |
| | 0.25 | 3 | 5 | 4 | 3 | | 4 | 3 | | 5 | 3 | | 5 | | 3 | 5 | 3 | | | 5 | | 3 | 4 | | 5 | | 4 | |
| | 0.125 | 1 | 2 | 3 | 3 | | 4 | 2 | | 5 | 2 | | 5 | | 3 | 4 | 2 | | | 5 | | 2 | 3 | | 5 | | 4 | |
| | 0.062 | 1 | 1 | 2 | 2 | | 4 | 2 | | 4 | 2 | | 5 | | 2 | 4 | 1 | | | 4 | | 1 | 1 | | 5 | | 3 | |
| 44 | 8 | | | | | | | | | 5 | | 1 | | | 4 | 5 | 5 | | | 5 | | 1 | 3 | | | | 1 | 5 |
| | 4 | | | | | | | | | 3 | | 1 | | | 2 | 5 | 3 | | | 3 | | 2 | 2 | | | | 1 | 3 |
| | 2 | | | | | | | 2 | | 1 | | | 1 | 4 | 3 | | | 3 | | 2 | 1 | | | 1 | 3 | | | |
| | 1 | | | | | | | | | 1 | | 1 | | | 1 | 2 | 1 | | | 1 | | 1 | 1 | | | | 1 | 3 |
| 45 | 8 | | | | | | | | | 5 | | 4 | | | 5 | 5 | 5 | | | 5 | | 4 | 5 | | | | 5 | 5 |
| | 4 | | | | | | | | | 5 | | 4 | | | 5 | 5 | 5 | | | 5 | | 4 | 5 | | | | 5 | 5 |
| | 2 | | | | | | | | | 5 | | 3 | | | 5 | 5 | 5 | | | 5 | | 4 | 5 | | | | 5 | 5 |
| | 1 | | | | | | | | | 4 | | 2 | | | 5 | 5 | 5 | | | 4 | | 4 | 5 | | | | 5 | 5 |
| | 1 | | | | | | | | | 5 | | 4 | | | 4 | 5 | 5 | | | 4 | | 2 | 4 | | | | 5 | 5 |
| | 0.50 | | | | | | | | | 5 | | 4 | | | 4 | 5 | 5 | | | 4 | | 2 | 4 | | | | 5 | 5 |
| | 0.25 | | | | | | | | | 5 | | 4 | | | 4 | 5 | 4 | | | 4 | | 2 | 4 | | | | 4 | 5 |
| | 0.25 | | | | | | | | | 5 | | 3 | | | 3 | 4 | 4 | | | 4 | | 2 | 4 | | | | 5 | 5 |
| | 0.125 | | | | | | | | | 5 | | 2 | | | 2 | 3 | 4 | | | 5 | | 2 | 4 | | | | 4 | 5 |
| | 0.062 | | | | | | | | | 4 | | 2 | | | 2 | 3 | 4 | | | 4 | | 1 | 3 | | | | 3 | 4 |
| 46 | 8 | | | | | | | | | 5 | | 5 | | | 4 | 5 | 5 | | | 5 | | 2 | 3 | | | | 2 | 5 |
| | 4 | | | | | | | | | 4 | | 4 | | | 5 | 5 | 5 | | | 5 | | 2 | 3 | | | | 3 | 5 |
| | 2 | | | | | | | | | 4 | | 3 | | | 4 | 5 | 5 | | | 4 | | 2 | 2 | | | | 2 | 5 |
| | 1 | | | | | | | | | 3 | | 1 | | | 4 | 5 | 4 | | | 3 | | 2 | 2 | | | | 2 | 4 |
| 47 | 8 | | | | | | | | | 5 | | 2 | | | 4 | 5 | 3 | | | 4 | | 2 | 4 | | | | 4 | 4 |
| | 4 | | | | | | | | | 5 | | 4 | | | 2 | 5 | 5 | | | 5 | | 4 | 4 | | | | 5 | 5 |
| | 2 | | | | | | | | | 5 | | 4 | | | 2 | 5 | 3 | | | 5 | | 4 | 4 | | | | 5 | 5 |
| | 1 | | | | | | | | | 5 | | 4 | | | 3 | 5 | 3 | | | 4 | | 3 | 5 | | | | 5 | 5 |
| | 0.50 | 4 | 5 | 5 | 3 | | 5 | 3 | | 5 | 3 | | 5 | | 5 | 5 | 3 | | | 5 | | 3 | 4 | | 5 | | 5 | |
| | 0.25 | 4 | 4 | 4 | 3 | | 5 | 3 | | 5 | 3 | | 5 | | 5 | 4 | 1 | | | 5 | | 3 | 4 | | 5 | | 4 | |
| | 0.125 | 4 | 4 | 4 | 3 | | 4 | 2 | | 4 | 2 | | 5 | | 4 | 4 | 1 | | | 4 | | 2 | 3 | | 5 | | 3 | |
| | 0.062 | 1 | 2 | 2 | 2 | | 4 | 2 | | 4 | 1 | | 5 | | 3 | 4 | 1 | | | 4 | | 2 | 3 | | 5 | | 3 | |
| 48 | 8 | | | | | | | | | 4 | | 5 | | | 2 | 4 | 4 | | | 4 | | 2 | 2 | | | | 4 | 5 |
| | 4 | | | | | | | | | 5 | | 4 | | | 1 | 3 | 4 | | | 3 | | 4 | 3 | | | | 3 | 5 |
| | 2 | | | | | | | | | 5 | | 3 | | | 1 | 3 | 3 | | | 4 | | 2 | 2 | | | | 2 | 4 |
| | 1 | | | | | | | | | 4 | | 3 | | | 1 | 4 | 1 | | | 4 | | 3 | 1 | | | | 1 | 5 |
| 49 | 8 | | | 2 | | | | | | 3 | 3 | | | | 2 | 4 | 4 | | | 4 | | | | | | | 2 | |
| | 4 | 1 | 1 | 1 | 1 | | 1 | 1 | | 1 | 1 | | 1 | | 1 | 1 | 1 | | | 1 | | 1 | 1 | | 1 | | 1 | |
| | 2 | 1 | 1 | 1 | 1 | | 1 | 1 | | 1 | 1 | | 1 | | 1 | 1 | 1 | | | 1 | | 1 | 1 | | 1 | | 1 | |
| | 1 | 1 | 1 | 1 | 1 | | 1 | 1 | | 1 | 1 | | 1 | | 1 | 1 | 1 | | | 1 | | 1 | 1 | | 1 | | 1 | |
| | 0.50 | 1 | 1 | 1 | 1 | | 1 | 1 | | 1 | 1 | | 1 | | 1 | 1 | 1 | | | 1 | | 1 | 1 | | 1 | | 1 | |
| 50 | 8 | | | 3 | | | | | | 5 | 3 | | | | 3 | 5 | 5 | | | 5 | | | | | | | 4 | |
| | 4 | 3 | 4 | 3 | 2 | | 5 | 3 | | 5 | 2 | | 5 | | 4 | 4 | 4 | | | 5 | | 3 | 3 | | 5 | | 4 | |
| | 2 | 3 | 2 | 2 | 2 | | 5 | 2 | | 5 | 1 | | 4 | | 2 | 3 | 3 | | | 5 | | 2 | 2 | | 5 | | 4 | |
| | 1 | 3 | 2 | 2 | 2 | | 4 | 1 | | 4 | 1 | | 3 | | 2 | 3 | 3 | | | 5 | | 2 | 2 | | 4 | | 4 | |
| | 0.50 | 3 | 1 | 2 | 2 | | 3 | 2 | | 4 | 1 | | 2 | | 2 | 3 | 4 | | | 5 | | 2 | 1 | | 4 | | 3 | |
| 51 | 8 | | | 4 | | | | | | 5 | 2 | | | | 4 | 5 | 4 | | | 5 | | | | | | | 4 | |
| | 4 | 4 | 5 | 4 | 3 | | 5 | 4 | | 5 | 3 | | 5 | | 5 | 5 | 5 | | | 5 | | 5 | 4 | | 5 | | 5 | |
| | 2 | 4 | 5 | 5 | 3 | | 5 | 4 | | 5 | 3 | | 5 | | 5 | 5 | 5 | | | 5 | | 3 | 4 | | 5 | | 5 | |
| | 1 | 5 | 5 | 5 | 4 | | 5 | 4 | | 5 | 3 | | 5 | | 5 | 5 | 5 | | | 5 | | 3 | 4 | | 5 | | 5 | |
| | 0.50 | 4 | 5 | 4 | 3 | | 5 | 4 | | 5 | 3 | | 5 | | 5 | 5 | 5 | | | 5 | | 2 | 3 | | 5 | | 4 | |
| 52 | 8 | | | 4 | | | | | | 5 | 2 | | | | 5 | 5 | 5 | | | 5 | | | | | | | 4 | |
| | 4 | 4 | 4 | 3 | 4 | | 5 | 4 | | 5 | 3 | | 5 | | 5 | 4 | 4 | | | 5 | | 3 | 4 | | 5 | | 4 | |
| | 2 | 4 | 4 | 4 | 3 | | 5 | 3 | | 5 | 2 | | 5 | | 5 | 4 | 2 | | | 5 | | 3 | 3 | | 5 | | 4 | |
| | 1 | 3 | 4 | 4 | 3 | | 5 | 3 | | 4 | 2 | | 5 | | 5 | 4 | 4 | | | 5 | | 3 | 3 | | 5 | | 4 | |
| | 0.50 | 3 | 4 | 3 | 3 | | 5 | 3 | | 4 | 2 | | 4 | | 4 | 3 | 4 | | | 5 | | 2 | 2 | | 5 | | 4 | |
| 53 | 8 | | | 4 | | | | | | 5 | 2 | | | | 5 | 5 | 5 | | | 4 | | | | | | | 4 | |
| | 4 | 2 | 4 | 3 | 3 | | 5 | 4 | | 5 | 2 | | 5 | | 4 | 5 | 5 | | | 5 | | 2 | 3 | | 5 | | 4 | |
| | 2 | 2 | 4 | 4 | 2 | | 5 | 4 | | 5 | 2 | | 5 | | 3 | 5 | 4 | | | 5 | | 2 | 2 | | 5 | | 4 | |
| | 1 | 2 | 4 | 3 | 2 | | 5 | 3 | | 5 | 2 | | 5 | | 4 | 5 | 4 | | | 5 | | 2 | 1 | | 5 | | 4 | |
| | 0.50 | 2 | 4 | 2 | 2 | | 5 | 3 | | 4 | 2 | | 5 | | 4 | 5 | 4 | | | 5 | | 2 | 1 | | 5 | | 3 | |

TABLE IV-continued

PLANT SPECIES
Postemergence

| Ex. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 54 | 8 | | | | | | | | | 5 | | 5 | | | 4 | 5 | 5 | | | 5 | | 2 | | 5 | | | 5 | 5 |
|  | 4 | | | | | | | | | 5 | | 5 | | | 5 | 5 | 5 | | | 5 | | 3 | | 5 | | | 5 | 5 |
|  | 2 | | | | | | | | | 5 | | 5 | | | 5 | 5 | 5 | | | 5 | | 3 | | 5 | | | 4 | 5 |
|  | 1 | | | | | | | | | 5 | | 4 | | | 5 | 5 | 4 | | | 5 | | 2 | | 5 | | | 5 | 5 |
|  | 1 | | | | | | | | | 5 | | 3 | | | 4 | 5 | 5 | | | 5 | | 3 | | 5 | | | 5 | 5 |
|  | 0.50 | | | | | | | | | 5 | | 2 | | | 4 | 5 | 4 | | | 5 | | 2 | | 5 | | | 5 | 5 |
|  | 0.25 | | | | | | | | | 5 | | 2 | | | 3 | 4 | 4 | | | 4 | | 2 | | 4 | | | 4 | 5 |
|  | 0.25 | | | | | | | | | 5 | | 2 | | | 4 | 5 | 5 | | | 4 | | 3 | | 4 | | | 4 | 5 |
|  | 0.125 | | | | | | | | | 5 | | 2 | | | 3 | 4 | 5 | | | 4 | | 2 | | 3 | | | 3 | 5 |
|  | 0.062 | | | | | | | | | 3 | | 2 | | | 2 | 4 | 5 | | | 3 | | 1 | | 1 | | | 3 | 5 |
|  | 0.031 | | | | | | | | | 2 | | 1 | | | 1 | 2 | 2 | | | 2 | | 1 | | 1 | | | 2 | 1 |
|  | 0.031 | | | | | | | | | 2 | | 1 | | | 2 | 3 | 3 | | | 2 | | 2 | | 1 | | | 3 | 2 |
| 55 | 8 | | | | | | | | | 2 | | 1 | | | 1 | 3 | 4 | | | 2 | | 1 | | 1 | | | 3 | 1 |
| 56 | 8 | | | | | | | | | 4 | | 1 | | | 4 | 4 | 4 | | | 2 | | 1 | | 2 | | | 2 | 3 |
|  | 4 | | | | | | | | | 4 | | 1 | | | 4 | 4 | 4 | | | 2 | | 1 | | 2 | | | 2 | 3 |
|  | 2 | | | | | | | | | 2 | | 1 | | | 1 | 3 | 3 | | | 1 | | 1 | | 1 | | | 1 | 3 |
|  | 1 | | | | | | | | | 1 | | 1 | | | 1 | 2 | 2 | | | 1 | | 1 | | 1 | | | 1 | 1 |
|  | 1 | | | | | | | | | | | | | | | | | | | | | | | | | | | |
| 57 | 8 | | | | | | | | | 5 | | 2 | | | 4 | 4 | 5 | | | 5 | | 3 | | 4 | | | 5 | 5 |
|  | 4 | | | | | | | | | 5 | | 4 | | | 3 | 5 | 5 | | | 4 | | 5 | | 5 | | | 5 | 5 |
|  | 2 | | | | | | | | | 5 | | 2 | | | 3 | 5 | 4 | | | 4 | | 4 | | 5 | | | 5 | 5 |
|  | 1 | | | | | | | | | 5 | | 1 | | | 1 | 4 | 3 | | | 3 | | 3 | | 5 | | | 5 | 5 |
|  | 1 | | | | | | | | | 5 | | 2 | | | 4 | 5 | 4 | | | 5 | | 4 | | 5 | | | 5 | 5 |
|  | 0.50 | | | | | | | | | 5 | | 2 | | | 3 | 5 | 3 | | | 4 | | 3 | | 5 | | | 4 | 5 |
|  | 0.25 | | | | | | | | | 5 | | 1 | | | 2 | 5 | 3 | | | 3 | | 3 | | 4 | | | 4 | 5 |
|  | 0.25 | | | | | | | | | 5 | | 1 | | | 1 | 4 | 3 | | | 4 | | 3 | | 4 | | | 3 | 5 |
|  | 0.125 | | | | | | | | | 4 | | 1 | | | 1 | 3 | 3 | | | 3 | | 2 | | 4 | | | 3 | 4 |
|  | 0.062 | | | | | | | | | 2 | | 1 | | | 1 | 3 | 3 | | | 3 | | 2 | | 1 | | | 2 | 4 |
| 58 | 8 | | | 3 | | | | | | 5 | 2 | | | | 5 | 5 | 5 | | | 5 | | | | | | | 5 | |
|  | 4 | 4 | 5 | 5 | 4 | | 5 | 4 | | 5 | 3 | | 5 | | 5 | 5 | 5 | | | 5 | | 4 | | 4 | 5 | | 5 | |
|  | 2 | 3 | 5 | 4 | 3 | | 5 | 3 | | 5 | 3 | | 5 | | 5 | 5 | 5 | | | 5 | | 4 | | 4 | 5 | | 5 | |
|  | 1 | 3 | 5 | 4 | 3 | | 5 | 3 | | 5 | 3 | | 5 | | 4 | 4 | 5 | | | 5 | | 4 | | 4 | 5 | | 5 | |
|  | 0.50 | 3 | 5 | 4 | 3 | | 5 | 3 | | 5 | 3 | | 5 | | 4 | 4 | 4 | | | 5 | | 4 | | 4 | 5 | | 5 | |
| 59 | 8 | | | 4 | | | | | | 5 | 2 | | | | 5 | 5 | 5 | | | 5 | | | | | | | 5 | |
|  | 4 | 5 | 5 | 5 | 4 | | 5 | 4 | | 5 | 3 | | 5 | | 5 | 5 | 5 | | | 5 | | 5 | | 5 | 5 | | 5 | |
|  | 2 | 5 | 5 | 5 | 4 | | 5 | 4 | | 5 | 3 | | 5 | | 5 | 5 | 5 | | | 5 | | 4 | | 5 | 5 | | 5 | |
|  | 1 | 5 | 4 | 4 | 3 | | 5 | 3 | | 5 | 3 | | 5 | | 4 | 4 | 5 | | | 5 | | 4 | | 4 | 4 | | 4 | |
|  | 0.50 | 4 | 4 | 4 | 3 | | 5 | 3 | | 5 | 3 | | 5 | | 4 | 4 | 4 | | | 5 | | 4 | | 4 | 4 | | 4 | |
| 60 | 8 | | | 4 | | | | | | 5 | 3 | | | | 5 | 5 | 5 | | | 5 | | | | | | | 5 | |
|  | 4 | 3 | 4 | 4 | 3 | | 5 | 3 | | 5 | 3 | | 5 | | 4 | 5 | 5 | | | 5 | | 3 | | 4 | 5 | | 5 | |
|  | 2 | 3 | 3 | 4 | 3 | | 5 | 3 | | 5 | 2 | | 5 | | 4 | 5 | 4 | | | 5 | | 3 | | 3 | 5 | | 5 | |
|  | 1 | 2 | 2 | 4 | 2 | | 5 | 3 | | 5 | 2 | | 5 | | 4 | 5 | 4 | | | 5 | | 2 | | 2 | 5 | | 4 | |
|  | 0.50 | 2 | 1 | 2 | 2 | | 4 | 3 | | 4 | 1 | | 3 | | 3 | 4 | 2 | | | 5 | | 3 | | 1 | 5 | | 4 | |
| 61 | 8 | | | 4 | | | | | | 5 | 3 | | | | 5 | 5 | 5 | | | 5 | | | | | | | 5 | |
|  | 4 | 4 | 5 | 5 | 4 | | 5 | 4 | | 5 | 4 | | 5 | | 4 | 5 | 5 | | | 5 | | 4 | | 5 | 5 | | 5 | |
|  | 2 | 4 | 5 | 5 | 4 | | 5 | 4 | | 5 | 4 | | 5 | | 4 | 5 | 5 | | | 5 | | 4 | | 4 | 5 | | 5 | |
|  | 1 | 4 | 5 | 4 | 3 | | 5 | 4 | | 5 | 3 | | 5 | | 4 | 4 | 4 | | | 5 | | 4 | | 4 | 5 | | 5 | |
|  | 0.50 | 3 | 5 | 4 | 3 | | 5 | 4 | | 5 | 3 | | 5 | | 4 | 4 | 3 | | | 5 | | 3 | | 3 | 5 | | 4 | |
| 62 | 8 | | | 4 | | | | | | 5 | 2 | | | | 5 | 5 | 5 | | | 5 | | | | | | | 4 | |
|  | 4 | 0 | 0 | 0 | 0 | | 0 | 0 | | 0 | 0 | | 0 | | 0 | 0 | 0 | | | 0 | | 0 | | 0 | 0 | | 0 | |
|  | 2 | 4 | 5 | 5 | 3 | | 5 | 3 | | 5 | 3 | | 5 | | 5 | 5 | 5 | | | 5 | | 5 | | 5 | 5 | | 5 | |
|  | 1 | 4 | 5 | 5 | 3 | | 5 | 3 | | 5 | 3 | | 5 | | 5 | 5 | 5 | | | 5 | | 5 | | 5 | 5 | | 4 | |
|  | 0.50 | 4 | 4 | 5 | 3 | | 5 | 3 | | 5 | 3 | | 5 | | 4 | 5 | 4 | | | 5 | | 4 | | 5 | 5 | | 4 | |
| 63 | 8 | | | 2 | | | | | | 4 | 1 | | | | 2 | 4 | 4 | | | 3 | | | | | | | 3 | |

Some of the compounds of this invention were further tested as described above. In addition to some of the species listed above, the compounds were evaluated against:

U=Sorghum
V=Foxtail Millet
X=Nightshade
Y=Sicklepod
Z=Wild Buckwheat

The compounds were pre-plant incorporated (PPI) or surface applied (SA).

However, plant injury ratings were made visually on a scale of 0-10 with 0 being no injury and 10 being plant death. The injury rating was multiplied by 10 to obtain a percent inhibition.

The results are recorded in Tables V and VI.
The following code was used in Table V and VI:
A=Corn
B=Cotton
C=Soybean
D=Wheat
F=Sugar Beets
G=Rice
J=Barnyard Grass
L=Crabgrass
M=Mustard
N=Pigweed
P=Wild Oat
Q=Velvetleaf
R=Jimsonweed
S=Morningglory
T=Zinnia
U=Sorghum
V=Foxtail Millet
X=Nightshade
Y=Sicklepod
Z=Wild Buckwheat

TABLE V

PREEMERGENCE HERBICIDE TESTING
PERCENT CROP INJURY OR WEED CONTROL

| Compound of Example No. | Application Rate lbs/A | App. | A | U | D | G | V | J | P | C | B | N | S | Q | R | X |
|---|---|---|---|---|---|---|---|---|---|---|---|---|---|---|---|---|
| 1 | 0.031 | PPI | 0 | 0 | 0 | 0 | 0 | 0 | 0 | 0 | 0 | 0 | 0 | 40 | 50 | — |
|   | 0.062 | PPI | 0 | 0 | 20 | 0 | 0 | 0 | 0 | 0 | 10 | 50 | 80 | 50 | 60 |   |
|   | 0.062 | PPI | 0 | 0 | 0 | 0 | 0 | 0 | 0 | 0 | 0 | 0 | 50 | 0 | 50 | 30 |
|   | 0.125 | PPI | 0 | 0 | 100 | 0 | 100 | 90 | 100 | 30 | 30 | 100 | 100 | 100 | 100 | 100 |
|   | 0.125 | PPI | 0 | 30 | 50 | 0 | 50 | 40 | 20 | 15 | 50 | 100 | 95 | 90 | 100 | — |
|   | 0.125 | PPI | 0 | 0 | 90 | 10 | 90 | 30 | 98 | 0 | 0 | 100 | 100 | 70 | 100 | 100 |
|   | 0.125 | PPI | 0 | 0 | 100 | 70 | 50 | 40 | 70 | 10 | 10 | 90 | 100 | 80 | 100 | 100 |
|   | 0.25 | PPI | 30 | 95 | 100 | 100 | 100 | 100 | 100 | 60 | 60 | 100 | 100 | 100 | 100 | 100 |
|   | 0.25 | PPI | 35 | 80 | 100 | 95 | 100 | 100 | 100 | 20 | 60 | 100 | 100 | 100 | 100 | 100 |
|   | 0.50 | PPI | 100 | 100 | 100 | 100 | 100 | 100 | 100 | 100 | 100 | 100 | 100 | 100 | 100 | 100 |
|   | 0.50 | PPI | 100 | 100 | 100 | 100 | 100 | 100 | 100 | 100 | 90 | 100 | 100 | 100 | 100 | 100 |
|   | 1.00 | PPI | 100 | 100 | 100 | 100 | 100 | 100 | 100 | 100 | 100 | 100 | 100 | 100 | 100 | 100 |
|   | 2.00 | PPI | 100 | 100 | 100 | 100 | 100 | 100 | 100 | 100 | 100 | 100 | 100 | 100 | 100 | 100 |
| 1 | 0.125 | SA | 10 | 0 | 20 | 0 | 40 | 40 | 10 | 0 | 0 | 100 | 0 | 0 | 70 | 95 |
|   | 0.125 | SA | 0 | 0 | 0 | 0 | 20 | 30 | 0 | 0 | 0 | 40 | 0 | 0 | 40 | 98 |
|   | 0.25 | SA | 50 | 0 | 60 | 10 | 100 | 70 | 20 | 10 | 0 | 100 | 90 | 90 | 100 | 98 |
|   | 0.25 | SA | 20 | 20 | 0 | 20 | 100 | 90 | 0 | 0 | 0 | 100 | 50 | 98 | 95 | 100 |
|   | 0.50 | SA | 100 | 100 | 95 | 80 | 100 | 98 | 100 | 100 | 90 | 100 | 100 | 100 | 100 | 100 |
|   | 0.50 | SA | 40 | 30 | 30 | 90 | 100 | 100 | 70 | 70 | 40 | 100 | 100 | 100 | 100 | 100 |
|   | 0.50 | SA | 50 | 50 | 30 | 80 | 100 | 100 | 30 | 10 | 10 | 100 | 70 | 100 | 100 | 100 |
|   | 1.00 | SA | 100 | 100 | 98 | 100 | 100 | 100 | 100 | 100 | 98 | 100 | 100 | 100 | 100 | 100 |
|   | 2.00 | SA | 100 | 100 | 100 | 100 | 100 | 100 | 100 | 100 | 100 | 100 | 100 | 100 | 100 | 100 |
| 5 | 0.062 | PPI | 0 | 0 | 0 | 0 | 50 | 0 | 20 | 0 | 0 | 80 | 0 | 0 | 0 | 100 |
|   | 0.125 | PPI | 0 | 0 | 20 | 0 | 80 | 0 | 20 | 0 | 0 | 90 | 40 | 40 | 80 | 100 |
|   | 0.25 | PPI | 0 | 0 | 80 | 80 | 70 | 70 | 90 | 80 | 100 | 100 | 100 | 100 | 100 | 100 |
|   | 0.25 | PPI | 40 | 0 | 70 | 20 | 90 | 50 | 80 | 30 | 70 | 100 | 95 | 98 | 80 | 100 |
|   | 0.50 | PPI | 40 | 40 | 95 | 90 | 95 | 95 | 100 | 100 | 100 | 100 | 100 | 100 | 100 | 100 |
|   | 1.00 | PPI | 70 | 80 | 100 | 100 | 100 | 100 | 100 | 100 | 100 | 100 | 100 | 100 | 100 | 100 |
| 5 | 0.062 | SA | 0 | 0 | 0 | 0 | 0 | 0 | 0 | 0 | 0 | 20 | 0 | 0 | 0 | 0 |
|   | 0.125 | SA | 0 | 0 | 0 | 0 | 20 | 0 | 0 | 0 | 0 | 90 | 0 | 10 | 70 | 50 |
|   | 0.25 | SA | 10 | 10 | 50 | 0 | 40 | 30 | 50 | 80 | 10 | 98 | 90 | 98 | 100 | 100 |
|   | 0.25 | SA | 0 | 0 | 10 | 0 | 50 | 0 | 0 | 10 | 0 | 100 | 40 | 70 | 100 | 100 |
|   | 0.50 | SA | 40 | 30 | 80 | 40 | 80 | 80 | 90 | 100 | 100 | 100 | 98 | 100 | 100 | 100 |
|   | 1.00 | SA | 60 | 70 | 90 | 60 | 98 | 80 | 95 | 100 | 100 | 100 | 100 | 100 | 100 | 100 |
| 7 | 0.062 | PPI | 0 | 0 | 0 | 0 | 0 | 0 | 0 | 0 | 0 | 0 | 0 | 0 | 0 | 0 |
|   | 0.125 | PPI | 0 | 0 | 10 | 0 | 0 | 0 | 0 | 0 | 0 | 50 | 100 | 30 | 70 | 60 |
|   | 0.25 | PPI | 0 | 0 | 0 | 30 | 0 | 30 | 70 | 20 | 0 | 60 | 100 | 100 | 100 | 98 |
|   | 0.25 | PPI | 0 | 10 | 10 | 0 | 20 | 60 | 40 | 0 | 0 | 98 | 100 | 80 | 100 | 100 |
|   | 0.50 | PPI | 0 | 30 | 50 | 30 | 60 | 80 | 90 | 70 | 40 | 100 | 100 | 100 | 100 | 100 |
|   | 1.00 | PPI | 10 | 60 | 70 | 30 | 80 | 95 | 100 | 90 | 70 | 100 | 100 | 100 | 100 | 100 |
| 7 | 0.25 | SA | 0 | 0 | 0 | 0 | 0 | 0 | 0 | 0 | 0 | 40 | 0 | 0 | 0 | 70 |
|   | 0.50 | SA | 0 | 0 | 0 | 0 | 50 | 40 | 0 | 0 | 0 | 90 | 0 | 90 | 50 | 90 |
|   | 1.00 | SA | 0 | 0 | 0 | 20 | 80 | 95 | 10 | 10 | 0 | 98 | 20 | 90 | 100 | 98 |
| 8 | 0.062 | SA | 0 | 0 | 0 | 0 | 0 | 0 | 0 | 0 | 0 | 0 | 0 | 0 | 0 | 0 |
|   | 0.125 | SA | 0 | 0 | 0 | 0 | 10 | 0 | 0 | 0 | 0 | 50 | 10 | 40 | 80 | 50 |
|   | 0.25 | SA | 0 | 10 | 30 | 50 | 100 | 100 | 20 | 10 | 10 | 100 | 100 | 100 | 98 | 100 |
|   | 0.25 | SA | 0 | 0 | 10 | 0 | 80 | 40 | 0 | 0 | 0 | 80 | 20 | 90 | 100 | 90 |
|   | 0.50 | SA | 60 | 50 | 98 | 60 | 100 | 100 | 50 | 70 | 40 | 100 | 100 | 100 | 100 | 100 |
|   | 1.00 | SA | 100 | 100 | 95 | 95 | 100 | 100 | 100 | 95 | 80 | 100 | 100 | 100 | 100 | 100 |
| 8 | 0.062 | PPI | 0 | 0 | 20 | 60 | 20 | 0 | 0 | 0 | 0 | 70 | 50 | 80 | 30 | 90 |
|   | 0.125 | PPI | 0 | 0 | 70 | 70 | 60 | 30 | 0 | 10 | 20 | 90 | 100 | 100 | 70 | 98 |
|   | 0.25 | PPI | 30 | 40 | 95 | 90 | 100 | 95 | 100 | 40 | 30 | 100 | 100 | 100 | 100 | 100 |
|   | 0.25 | PPI | 0 | 10 | 90 | 60 | 100 | 90 | 80 | 30 | 30 | 100 | 100 | 100 | 90 | 98 |
|   | 0.50 | PPI | 70 | 100 | 100 | 95 | 100 | 100 | 100 | 100 | 98 | 100 | 100 | 100 | 100 | 100 |
|   | 1.00 | PPI | 98 | 100 | 100 | 100 | 100 | 100 | 100 | 100 | 100 | 100 | 100 | 100 | 100 | 100 |
| 9 | 0.25 | PPI | 0 | 0 | 80 | 30 | 95 | 60 | 80 | 10 | 0 | 70 | 98 | 100 | 80 | 90 |
|   | 0.50 | PPI | 20 | 50 | 90 | 60 | 100 | 90 | 80 | 70 | 50 | 95 | 100 | 100 | 90 | 98 |
|   | 1.00 | PPI | 50 | 60 | 90 | 50 | 100 | 95 | 95 | 80 | 70 | 98 | 100 | 100 | 90 | 100 |
| 9 | 0.25 | SA | 0 | 0 | 10 | 0 | 70 | 0 | — | 10 | 0 | 40 | 40 | 98 | 0 | 50 |
|   | 0.50 | SA | 0 | 0 | 30 | 0 | 95 | 60 | — | 30 | 0 | 90 | 50 | 100 | 90 | 100 |
|   | 1.00 | SA | 40 | 40 | 40 | 20 | 100 | 80 | — | 50 | 0 | 98 | 90 | 100 | 90 | 100 |
| 10 | 0.50 | PPI | 0 | 0 | 20 | 0 | 0 | 0 | 0 | 0 | 0 | 0 | 60 | 0 | 50 | 70 |
|   | 1.00 | PPI | 0 | 0 | 30 | 30 | 40 | 0 | 40 | 0 | 0 | — | 80 | 60 | 80 | 90 |
|   | 2.00 | PPI | 0 | 0 | 70 | 70 | 70 | 30 | 50 | 50 | 50 | 100 | 60 | 98 | 100 | 100 |
| 10 | 1.00 | SA | 0 | 0 | 0 | 0 | 0 | 0 | 0 | 0 | 0 | 0 | 30 | 50 | 0 | 0 |
|   | 2.00 | SA | 0 | 0 | 0 | 0 | 0 | 0 | 0 | 0 | 0 | 0 | — | 40 | 50 | 0 |
|   | 4.00 | SA | 0 | 0 | 0 | 10 | 30 | 50 | 0 | 10 | 0 | 80 | 30 | 20 | 90 | 80 |
| 12 | 0.50 | PPI | 0 | 0 | 0 | 10 | 40 | 0 | 40 | 0 | 0 | 0 | 10 | 0 | 50 | 30 |
|   | 1.00 | PPI | 0 | 20 | 30 | 50 | 60 | 60 | 80 | 0 | 0 | 30 | 70 | 0 | 90 | 95 |
|   | 2.00 | PPI | 50 | 60 | 90 | 70 | 100 | 98 | 100 | 40 | 20 | 70 | 100 | 50 | 100 | 100 |
| 12 | 1.00 | SA | 0 | 0 | 0 | 20 | 50 | 50 | 0 | 0 | 0 | 0 | 0 | 0 | 20 | 80 |
|   | 2.00 | SA | 20 | 0 | 0 | 70 | 98 | 80 | 20 | 0 | 0 | 50 | 10 | 30 | 50 | 100 |
|   | 4.00 | SA | 40 | 30 | 10 | 70 | 100 | 100 | 40 | 10 | 0 | 95 | 40 | 50 | 100 | 100 |
| 14 | 0.50 | PPI | 0 | 0 | 0 | 80 | 100 | 70 | 98 | 0 | 0 | 60 | 40 | 0 | 100 | — |
|   | 1.00 | PPI | 0 | 60 | 40 | 95 | 100 | 100 | 100 | 20 | 20 | 100 | 98 | 80 | 100 | — |
|   | 2.00 | PPI | 40 | 90 | 100 | 100 | 100 | 100 | 100 | 40 | 70 | 100 | 100 | 90 | 100 | — |

TABLE V-continued

PREEMERGENCE HERBICIDE TESTING
PERCENT CROP INJURY OR WEED CONTROL

| Compound of Example No. | Application Rate lbs/A | App. | A | U | D | G | V | J | P | C | B | N | S | Q | R | X |
|---|---|---|---|---|---|---|---|---|---|---|---|---|---|---|---|---|
| 14 | 0.50 | SA | 0 | 0 | 0 | 0 | 10 | 10 | 0 | 0 | 0 | 50 | 0 | 0 | 98 | 70 |
|  | 1.00 | SA | 0 | 0 | 0 | 30 | 90 | 30 | 30 | 0 | 0 | 80 | 0 | 50 | 98 | 90 |
|  | 2.00 | SA | 0 | 0 | 0 | 10 | 98 | 90 | 40 | 20 | 0 | 100 | 0 | 30 | 100 | 98 |
| 19 | 0.125 | PPI | 0 | 0 | 20 | 0 | 0 | 0 | 0 | 10 | 0 | 0 | 40 | 40 | 20 | 20 |
|  | 0.25 | PPI | 10 | 0 | 10 | 30 | 0 | 0 | 0 | 10 | 0 | 0 | 70 | 60 | 60 | 30 |
|  | 0.50 | PPI | 0 | 0 | 10 | 80 | 50 | 50 | 0 | 50 | 0 | 0 | 100 | 80 | 100 | 90 |
|  | 0.50 | PPI | 10 | 0 | 60 | 70 | 60 | 0 | 0 | 30 | 50 | 50 | 100 | 95 | 100 | 95 |
|  | 1.00 | PPI | 0 | 0 | 95 | 90 | 100 | 98 | 70 | 100 | 60 | 98 | 100 | 100 | 100 | 100 |
|  | 2.00 | PPI | 30 | 10 | 100 | 100 | 100 | 100 | 95 | 100 | 95 | 100 | 100 | 100 | 100 | 100 |
| 19 | 0.50 | SA | 0 | 0 | 0 | 0 | 0 | 0 | 0 | 0 | 0 | 50 | 0 | 0 | 0 | 0 |
|  | 1.00 | SA | 0 | 0 | 0 | 30 | 0 | 0 | 0 | 0 | 0 | 95 | 50 | 40 | — | 0 |
|  | 2.00 | SA | 0 | 0 | 0 | 40 | 20 | 0 | 0 | 10 | 0 | 80 | 80 | 0 | 80 | 20 |
| 20 | 0.062 | PPI | 0 | 0 | 0 | 0 | 0 | 0 | 0 | 0 | 0 | 0 | 0 | 0 | 0 | 0 |
|  | 0.125 | PPI | 0 | 0 | 20 | 0 | 0 | 0 | 20 | 0 | 0 | 40 | 100 | 20 | 70 | 40 |
|  | 0.25 | PPI | 0 | 20 | 100 | 80 | 100 | 80 | 98 | 10 | 10 | 100 | 100 | 98 | 100 | 98 |
|  | 0.25 | PPI | 50 | 98 | 100 | 90 | 100 | 98 | 100 | 70 | 50 | 100 | 100 | 100 | 100 | 100 |
|  | 0.50 | PPI | 80 | 100 | 100 | 100 | 100 | 100 | 100 | 100 | 90 | 100 | 100 | 100 | 100 | 100 |
|  | 1.00 | PPI | 100 | 100 | 100 | 100 | 100 | 100 | 100 | 100 | 100 | 100 | 100 | 100 | 100 | 100 |
| 20 | 0.125 | SA | 0 | 0 | 0 | 0 | 0 | 0 | 0 | 0 | 0 | 95 | 0 | 0 | 0 | 100 |
|  | 0.25 | SA | 0 | 0 | 0 | 0 | 98 | 20 | 0 | 0 | 0 | 100 | 0 | 40 | 70 | 100 |
|  | 0.25 | SA | 0 | 0 | 10 | 0 | 20 | 0 | 20 | 0 | 0 | 100 | 70 | 60 | 50 | 98 |
|  | 0.50 | SA | 0 | 10 | 10 | 50 | 100 | 100 | 30 | 20 | 0 | 100 | 40 | 100 | 100 | 100 |
|  | 0.50 | SA | 100 | 100 | 40 | 50 | 100 | 70 | 50 | 50 | 20 | 100 | 90 | 90 | 100 | 100 |
|  | 1.00 | SA | 100 | 100 | 98 | 95 | 100 | 100 | 98 | 100 | 70 | 100 | 100 | 100 | 100 | 100 |
| 21 | 0.062 | PPI | 0 | 0 | 0 | 0 | 0 | 0 | 0 | 0 | 0 | 50 | 40 | 30 | 0 | 40 |
|  | 0.125 | PPI | 0 | 0 | 40 | 10 | 20 | 40 | 50 | 0 | 0 | 80 | 100 | 60 | 90 | 70 |
|  | 0.25 | PPI | 20 | 80 | 98 | 30 | 100 | 80 | 100 | 40 | 40 | 100 | 100 | 95 | 100 | 100 |
|  | 0.25 | PPI | 10 | 10 | 90 | 40 | 100 | 70 | 95 | 50 | 40 | 100 | 100 | 100 | 100 | 98 |
|  | 0.50 | PPI | 60 | 100 | 100 | 90 | 100 | 100 | 100 | 98 | 90 | 100 | 100 | 100 | 100 | 100 |
|  | 1.00 | PPI | 90 | 100 | 100 | 100 | 100 | 100 | 100 | 100 | 100 | 100 | 100 | 100 | 100 | 100 |
| 21 | 0.125 | SA | 0 | 0 | 0 | 0 | 0 | 0 | 0 | 0 | 0 | 40 | 0 | 0 | 0 | 0 |
|  | 0.25 | SA | 0 | 0 | 0 | 10 | 90 | 0 | 0 | 0 | 0 | 98 | 70 | 60 | 30 | 95 |
|  | 0.50 | SA | 40 | 90 | 40 | 70 | 100 | 98 | 90 | 60 | 20 | 100 | 95 | 100 | 100 | 100 |
|  | 0.50 | SA | 0 | 0 | 20 | 20 | 100 | 20 | 0 | 20 | 0 | 95 | 100 | 90 | 90 | 100 |
|  | 1.00 | SA | 80 | 100 | 95 | 95 | 100 | 100 | 100 | 98 | 50 | 100 | 100 | 100 | 100 | 100 |
|  | 2.00 | SA | 98 | 100 | 100 | 100 | 100 | 100 | 100 | 98 | 100 | 100 | 100 | 100 | 100 | 100 |
| 22 | 0.062 | PPI | 0 | 0 | 0 | 0 | 0 | 0 | 0 | 0 | 0 | 0 | 40 | 0 | 0 | 60 |
|  | 0.125 | PPI | 0 | 0 | 40 | 0 | 50 | 30 | 0 | 0 | 0 | 80 | 100 | 60 | 80 | 80 |
|  | 0.25 | PPI | 0 | 0 | 90 | 70 | 90 | 80 | 100 | 40 | 30 | 100 | 98 | 80 | 100 | 100 |
|  | 0.25 | PPI | 0 | 0 | 80 | 20 | 98 | 70 | 60 | 10 | 20 | 100 | 100 | 98 | 98 | 98 |
|  | 0.50 | PPI | 40 | 98 | 100 | 80 | 100 | 100 | 100 | 100 | 70 | 100 | 100 | 100 | 100 | 100 |
|  | 1.00 | PPI | 80 | 100 | 100 | 100 | 100 | 100 | 100 | 100 | 100 | 100 | 100 | 100 | 100 | 100 |
| 22 | 0.125 | SA | 0 | 0 | 0 | 0 | 0 | 0 | 0 | 0 | 0 | 50 | 0 | 0 | 0 | 0 |
|  | 0.25 | SA | 0 | 0 | 0 | 10 | 90 | 20 | 0 | 0 | 0 | 100 | 50 | 20 | 20 | 98 |
|  | 0.50 | SA | 30 | 70 | 30 | 10 | 100 | 100 | 70 | 50 | 10 | 100 | 90 | 100 | 100 | 100 |
|  | 0.50 | SA | 20 | 0 | 0 | 10 | 100 | 30 | — | 20 | 0 | 100 | 70 | 90 | 20 | 100 |
|  | 1.00 | SA | 98 | 100 | 100 | 98 | 100 | 100 | 100 | 80 | 80 | 100 | 100 | 100 | 100 | 100 |
|  | 2.00 | SA | 100 | 100 | 100 | 100 | 100 | 100 | 100 | 98 | 100 | 100 | 100 | 100 | 100 | 100 |
| 23 | 0.062 | PPI | 0 | 0 | 10 | 0 | 0 | 0 | 0 | 0 | 0 | 0 | 80 | 0 | 0 | 0 |
|  | 0.125 | PPI | 0 | 0 | 50 | 20 | 20 | 0 | 40 | 0 | 0 | 80 | 100 | 70 | 50 | 95 |
|  | 0.25 | PPI | 0 | 0 | 90 | 20 | 98 | 80 | 98 | 40 | 20 | 100 | 100 | 90 | 100 | 98 |
|  | 0.25 | PPI | 0 | 0 | 100 | 60 | 100 | 60 | 90 | — | 20 | 100 | 100 | 100 | 100 | 100 |
|  | 0.50 | PPI | 40 | 98 | 100 | 50 | 100 | 100 | 100 | 90 | 40 | 100 | 100 | 100 | 100 | 100 |
|  | 1.00 | PPI | 70 | 98 | 100 | 90 | 100 | 100 | 100 | 98 | 90 | 100 | 100 | 100 | 100 | 100 |
| 23 | 0.25 | SA | 0 | 0 | 0 | 0 | 50 | 0 | 0 | 0 | 0 | 90 | 10 | 20 | 0 | 50 |
|  | 0.50 | SA | 0 | 0 | 10 | 10 | 100 | 98 | 0 | 20 | 0 | 100 | 50 | 95 | 0 | 98 |
|  | 1.00 | SA | 50 | 30 | 20 | 30 | 100 | 100 | 30 | 50 | 10 | 100 | 50 | 100 | 98 | 100 |
| 24 | 0.062 | PPI | 0 | 0 | 0 | 0 | 0 | 0 | 0 | 0 | 0 | 50 | 50 | 40 | 0 | 0 |
|  | 0.125 | PPI | 0 | 0 | 50 | 20 | 30 | 50 | 30 | 10 | 0 | 80 | 98 | 70 | 95 | 80 |
|  | 0.25 | PPI | 10 | 30 | 98 | 50 | 100 | 90 | 100 | 30 | 20 | 100 | 100 | 100 | 100 | 100 |
|  | 0.25 | PPI | 0 | 0 | 80 | 70 | 100 | 90 | 80 | 40 | 20 | 100 | 100 | 98 | 98 | 98 |
|  | 0.50 | PPI | 60 | 98 | 100 | 90 | 100 | 100 | 100 | 95 | 90 | 100 | 100 | 100 | 100 | 100 |
|  | 1.00 | PPI | 98 | 100 | 100 | 95 | 100 | 100 | 100 | 100 | 98 | 100 | 100 | 100 | 100 | 100 |
| 24 | 0.125 | SA | 0 | 0 | 0 | 0 | 0 | 0 | 0 | 0 | 0 | 50 | 0 | 0 | 0 | 0 |
|  | 0.25 | SA | 0 | 0 | 0 | 0 | 20 | 0 | 0 | 0 | 0 | 98 | 30 | 0 | 0 | 98 |
|  | 0.50 | SA | 40 | 90 | 80 | 90 | 100 | 100 | 80 | 90 | 20 | 100 | 100 | 100 | 100 | 100 |
|  | 0.50 | SA | 20 | 20 | 10 | 50 | 100 | 70 | 30 | 20 | 0 | 100 | 70 | 98 | 80 | 98 |
|  | 1.00 | SA | 80 | 100 | 95 | 98 | 100 | 100 | 100 | 98 | 98 | 100 | 100 | 100 | 100 | 100 |
|  | 2.00 | SA | 100 | 100 | 100 | 100 | 100 | 100 | 100 | 100 | 100 | 100 | 100 | 100 | 100 | 100 |
| 25 | 0.062 | PPI | 0 | 0 | 30 | 0 | 0 | 0 | 0 | 0 | 0 | 0 | 60 | 0 | 70 | 20 |
|  | 0.125 | PPI | 0 | 0 | 100 | 20 | 40 | 0 | 60 | 0 | 0 | 100 | 100 | 80 | 100 | 98 |
|  | 0.25 | PPI | 0 | 10 | 90 | 80 | 100 | 90 | 95 | 95 | 40 | 100 | 100 | 100 | 100 | 100 |
|  | 0.25 | PPI | 30 | 50 | 100 | 90 | 100 | 90 | 100 | 40 | 30 | 100 | 100 | 100 | 100 | 100 |
|  | 0.50 | PPI | 40 | 98 | 100 | 90 | 100 | 100 | 98 | 80 | 90 | 100 | 100 | 100 | 100 | 100 |
|  | 1.00 | PPI | 90 | 100 | 100 | 100 | 100 | 100 | 100 | 95 | 100 | 100 | 100 | 100 | 100 | 100 |
| 25 | 0.125 | SA | 10 | 0 | 0 | 0 | 0 | 0 | 0 | 0 | 0 | 0 | 0 | 0 | 0 | 0 |

TABLE V-continued
PREEMERGENCE HERBICIDE TESTING
PERCENT CROP INJURY OR WEED CONTROL

| Compound of Example No. | Application Rate lbs/A | App. | A | U | D | G | V | J | P | C | B | N | S | Q | R | X |
|---|---|---|---|---|---|---|---|---|---|---|---|---|---|---|---|---|
| | 0.25 | SA | 20 | 10 | 10 | 0 | 98 | 30 | 0 | 10 | 10 | 90 | 0 | 30 | 90 | 98 |
| | 0.50 | SA | 0 | 0 | 10 | 0 | 98 | 80 | 0 | 40 | 0 | 98 | 95 | 80 | 98 | 98 |
| | 0.50 | SA | 80 | 100 | 20 | 10 | 100 | 70 | 70 | 70 | 10 | 100 | 100 | 100 | 100 | 100 |
| | 1.00 | SA | 20 | 30 | 70 | 50 | 100 | 95 | 80 | 98 | 30 | 100 | 100 | 98 | 100 | 100 |
| | 2.00 | SA | 70 | 80 | 95 | 70 | 100 | 98 | 80 | 100 | 50 | 100 | 100 | 100 | 100 | 100 |
| 26 | .50 | PPI | 10 | 40 | 95 | 40 | 100 | 98 | 100 | 80 | 20 | 100 | 100 | 98 | 100 | 100 |
| | .50 | PPI | 0 | 20 | 100 | 50 | 100 | 95 | 98 | 80 | 10 | 100 | 100 | 100 | 100 | 100 |
| | 1.00 | PPI | 40 | 90 | 100 | 60 | 100 | 100 | 100 | 90 | 90 | 100 | 100 | 100 | 100 | 100 |
| | 2.00 | PPI | 90 | 100 | 100 | 80 | 100 | 100 | 100 | 90 | 98 | 100 | 100 | 100 | 100 | 100 |
| 26 | 0.50 | SA | 0 | 0 | 0 | 0 | 100 | 40 | 10 | 0 | 0 | 80 | 0 | 20 | 50 | 90 |
| | 1.00 | SA | 10 | 10 | 10 | 50 | 100 | 98 | 30 | 10 | 0 | 100 | 20 | 80 | 80 | 95 |
| | 2.00 | SA | 30 | 40 | 30 | 80 | 100 | 100 | 40 | 20 | 0 | 100 | 40 | 80 | 95 | 100 |
| 26 | 0.125 | PPI | 0 | 0 | 10 | 0 | 0 | 0 | 0 | 0 | 0 | 50 | 80 | 40 | 70 | 50 |
| | 0.25 | PPI | 0 | 0 | 60 | 20 | 30 | 50 | 70 | 10 | 0 | 98 | 100 | 70 | 100 | 98 |
| 27 | 0.062 | PPI | 0 | 0 | 10 | 10 | 0 | 0 | 10 | 0 | 0 | 50 | 60 | 0 | 90 | 80 |
| | 0.125 | PPI | 0 | 0 | 90 | 10 | 0 | 0 | 20 | 20 | 0 | 98 | 100 | 80 | 100 | 98 |
| | 0.25 | PPI | 40 | 80 | 95 | 90 | 100 | 98 | 100 | 40 | 40 | 100 | 100 | 100 | 100 | 100 |
| | 0.25 | PPI | 20 | 10 | 100 | 100 | 100 | 90 | 100 | 80 | 70 | 100 | 100 | 100 | 100 | 95 |
| | 0.50 | PPI | 80 | 100 | 100 | 100 | 100 | 100 | 100 | 100 | 90 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 27 | 0.125 | SA | 0 | 0 | 0 | 0 | 0 | 0 | 0 | 0 | 0 | 60 | 0 | 0 | 90 | 80 |
| | 0.25 | SA | 0 | 0 | 0 | 30 | 60 | 80 | 10 | 10 | 10 | 90 | 40 | 20 | 100 | 100 |
| | 0.50 | SA | 40 | 20 | 20 | 40 | 100 | 100 | 40 | 30 | 20 | 100 | 90 | 100 | 100 | 100 |
| | 0.50 | SA | 40 | 30 | 20 | 60 | 100 | 100 | 10 | 10 | 10 | 100 | 90 | 50 | 100 | 100 |
| | 1.00 | SA | 60 | 80 | 70 | 98 | 100 | 100 | 100 | 95 | 60 | 100 | 100 | 100 | 100 | 100 |
| | 2.00 | SA | 100 | 100 | 100 | 100 | 100 | 100 | 100 | 100 | 100 | 100 | 100 | 100 | 100 | 100 |
| 28 | 0.062 | PPI | 0 | 0 | 10 | 0 | 0 | 0 | 0 | 0 | 0 | 50 | 0 | 0 | 95 | 70 |
| | 0.125 | PPI | 0 | 0 | 100 | 10 | 0 | 0 | 40 | 0 | 0 | 100 | 100 | 70 | 100 | 90 |
| | 0.25 | PPI | 0 | 0 | 100 | 100 | 100 | 100 | 100 | 90 | 80 | 100 | 100 | 100 | 100 | 100 |
| | 0.25 | PPI | 0 | 10 | 100 | 90 | 100 | 90 | 100 | 70 | 60 | 100 | 100 | 90 | 100 | 100 |
| | 0.50 | PPI | 60 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 28 | 0.062 | SA | 0 | 0 | 0 | 0 | 0 | 0 | 0 | 0 | 0 | 80 | 0 | 0 | 0 | 50 |
| | 0.125 | SA | 0 | 0 | 0 | 20 | 0 | 10 | 0 | 0 | 0 | 100 | 0 | 10 | 60 | 98 |
| | 0.25 | SA | 0 | 0 | 0 | 10 | 90 | 100 | 0 | 0 | 10 | 100 | 40 | 10 | 100 | 100 |
| | 0.25 | SA | 0 | 0 | 0 | 20 | 60 | 80 | 0 | 0 | 0 | 100 | 50 | 40 | 90 | 100 |
| | 0.50 | SA | 50 | 100 | 20 | 90 | 100 | 100 | 20 | 70 | 60 | 100 | 80 | 100 | 100 | 100 |
| | 1.00 | SA | 50 | 100 | 80 | 100 | 100 | 100 | 70 | 70 | 90 | 100 | 100 | 100 | 100 | 100 |
| 29 | 0.062 | PPI | 0 | 0 | 0 | 0 | 0 | 0 | 0 | 0 | 0 | 0 | 60 | 0 | 0 | 50 |
| | 0.125 | PPI | 0 | 0 | 50 | 30 | 0 | 20 | 20 | 10 | 0 | 50 | 100 | 60 | 100 | 98 |
| | 0.25 | PPI | 0 | 10 | 100 | 100 | 100 | 100 | 100 | 90 | 80 | 100 | 100 | 100 | 100 | 100 |
| | 0.25 | PPI | 10 | 0 | 100 | 80 | 100 | 70 | 100 | 100 | 40 | 50 | 100 | 100 | 100 | 100 |
| | 0.50 | PPI | 60 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 29 | 0.062 | SA | 0 | 0 | 0 | 0 | 0 | 0 | 0 | 0 | 0 | 60 | 0 | 0 | 0 | 0 |
| | 0.125 | SA | 0 | 0 | 0 | 0 | 0 | 0 | 0 | 0 | 0 | 95 | 40 | 0 | 80 | 60 |
| | 0.25 | SA | 0 | 0 | 10 | 20 | 80 | 10 | 0 | 0 | 0 | 100 | 40 | 80 | 100 | 80 |
| | 0.25 | SA | 0 | 0 | 0 | 0 | 40 | 20 | 0 | 0 | 0 | 100 | 70 | 40 | 100 | 98 |
| | 0.50 | SA | 20 | 50 | 10 | 20 | 100 | 100 | 10 | 20 | 10 | 100 | 60 | 100 | 100 | 100 |
| | 1.00 | SA | 40 | 100 | 50 | 95 | 100 | 100 | 90 | 50 | 95 | 100 | 100 | 100 | 100 | 100 |
| 30 | 0.25 | PPI | 10 | 0 | 98 | 100 | 98 | 100 | 100 | 60 | 98 | 100 | 100 | 98 | 100 | 100 |
| | 0.50 | PPI | 80 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 30 | 0.25 | SA | 0 | 0 | 0 | 20 | 30 | 0 | 0 | 0 | 0 | 95 | 0 | 70 | 98 | 98 |
| | 0.50 | SA | 0 | 0 | 10 | 40 | 98 | 60 | 10 | 10 | 0 | 95 | 70 | 80 | 90 | 98 |
| | 1.00 | SA | 98 | 98 | 60 | 98 | 100 | 98 | 80 | 98 | 20 | 100 | 98 | 100 | 98 | 100 |
| 31 | 0.50 | PPI | 0 | 0 | 10 | 0 | 0 | 0 | 0 | 0 | 0 | 0 | 98 | 0 | 70 | 70 |
| | 1.00 | PPI | 0 | 10 | 50 | 20 | 40 | 0 | 50 | 30 | 0 | 50 | 100 | 98 | 100 | 100 |
| | 2.00 | PPI | 0 | 20 | 80 | 60 | 80 | 50 | 90 | 95 | 50 | 80 | 100 | 100 | 100 | 100 |
| 31 | 0.50 | SA | 0 | 0 | 0 | 0 | 0 | 0 | 0 | 0 | 0 | 20 | 0 | 0 | 0 | 20 |
| | 1.00 | SA | 0 | 0 | 0 | 0 | 0 | 0 | 0 | 0 | 0 | 50 | 0 | 0 | 50 | 95 |
| | 2.00 | SA | 0 | 0 | 0 | 0 | 40 | 20 | 0 | 10 | 0 | 90 | 40 | 90 | 98 | 100 |
| 32 | 0.062 | PPI | 0 | 0 | 20 | 0 | 0 | 0 | 0 | 0 | 0 | 0 | 70 | 0 | 40 | 50 |
| | 0.125 | PPI | 0 | 0 | 70 | 40 | 30 | 0 | 40 | 0 | 0 | 90 | 90 | 90 | 95 | 100 |
| | 0.25 | PPI | 0 | 0 | 90 | 40 | 100 | 80 | 90 | 0 | 0 | 100 | 100 | 100 | 100 | 100 |
| | 0.25 | PPI | 0 | 20 | 100 | 60 | 98 | 20 | 80 | 10 | 0 | 100 | 100 | 100 | 98 | 100 |
| | 0.50 | PPI | 40 | 60 | 95 | 95 | 100 | 100 | 100 | 98 | 80 | 100 | 100 | 100 | 100 | 100 |
| | 1.00 | PPI | 70 | 90 | 100 | 100 | 100 | 100 | 100 | 100 | 100 | 100 | 100 | 100 | 100 | 100 |
| 32 | 0.50 | SA | 0 | 0 | 0 | 20 | 30 | 40 | 0 | 0 | 0 | 100 | 30 | 50 | 90 | 100 |
| | 1.00 | SA | 0 | 0 | 30 | 50 | 100 | 98 | 0 | 0 | 0 | 100 | 60 | 100 | 100 | 100 |
| | 2.00 | SA | 20 | 10 | 50 | 70 | 100 | 98 | 10 | 10 | 0 | 100 | 100 | 100 | 100 | 100 |
| 34 | 0.062 | PPI | 0 | 0 | 20 | 10 | 20 | 20 | 0 | 0 | 0 | 30 | 30 | 20 | 80 | 50 |
| | 0.125 | PPI | 0 | 0 | 40 | 10 | 30 | 20 | 30 | 10 | 30 | 10 | 100 | 60 | 100 | 90 |
| | 0.25 | PPI | 0 | 0 | 98 | 90 | 80 | 50 | 70 | 0 | 0 | 40 | 100 | 100 | 100 | 100 |
| | 0.25 | PPI | 20 | 10 | 90 | 50 | 100 | 50 | 90 | 40 | 60 | 90 | 100 | 100 | 100 | 98 |
| | 0.50 | PPI | 20 | 40 | 100 | 100 | 100 | 100 | 100 | 100 | 100 | 80 | 100 | 100 | 100 | 100 |

TABLE V-continued
PREEMERGENCE HERBICIDE TESTING
PERCENT CROP INJURY OR WEED CONTROL

| Compound of Example No. | Application Rate lbs/A | App. | A | U | D | G | V | J | P | C | B | N | S | Q | R | X |
|---|---|---|---|---|---|---|---|---|---|---|---|---|---|---|---|---|
| | 1.00 | PPI | 70 | 70 | 100 | 100 | 100 | 100 | 100 | 100 | 100 | 100 | 100 | 100 | 100 | 100 |
| 34 | 0.25 | SA | 0 | 0 | 0 | 0 | 40 | 0 | 0 | 0 | 0 | 0 | 30 | 100 | 95 | 95 |
| | 0.50 | SA | 0 | 0 | 0 | 10 | 60 | 30 | 0 | 0 | 0 | 0 | 90 | 100 | 95 | 100 |
| | 1.00 | SA | 30 | 10 | 10 | 10 | 98 | 40 | 0 | 10 | 10 | 50 | 90 | 100 | 98 | 98 |
| 36 | 0.062 | PPI | 0 | 0 | 40 | 0 | 0 | 0 | 20 | 20 | 0 | 0 | 80 | 0 | 0 | 98 |
| | 0.125 | PPI | 0 | 0 | 100 | 95 | 40 | 0 | 100 | 40 | 40 | 50 | 100 | 80 | 100 | 98 |
| | 0.25 | PPI | 50 | 70 | 100 | 100 | 100 | 100 | 100 | 98 | 98 | 100 | 100 | 100 | 100 | 100 |
| | 0.25 | PPI | 30 | 98 | 100 | 100 | 100 | 98 | 100 | 98 | 100 | 100 | 100 | 100 | 100 | 100 |
| | 0.50 | PPI | 95 | 100 | 100 | 100 | 100 | 100 | 100 | 100 | 100 | 100 | 100 | 100 | 100 | 100 |
| | 1.00 | PPI | 95 | 100 | 100 | 100 | 100 | 100 | 100 | 100 | 100 | 100 | 100 | 100 | 100 | 100 |
| 36 | 0.25 | SA | 0 | 0 | 0 | 0 | 98 | 70 | 0 | 10 | 10 | 100 | 80 | 70 | 100 | 100 |
| | 0.50 | SA | 40 | 20 | 20 | 70 | 100 | 95 | 20 | 10 | 30 | 100 | 100 | 100 | 100 | 100 |
| | 1.00 | SA | 70 | 70 | 40 | 90 | 100 | 98 | 90 | 90 | 90 | 100 | 100 | 100 | 100 | 100 |
| 37 | 0.062 | PPI | 0 | 0 | 20 | 0 | 0 | 0 | 30 | 20 | 0 | 0 | 90 | 0 | 0 | 90 |
| | 0.125 | PPI | 0 | 0 | 100 | 95 | 0 | 0 | 100 | 60 | 20 | 20 | 98 | 40 | 100 | 98 |
| | 0.25 | PPI | 20 | 50 | 100 | 98 | 100 | 80 | 100 | 50 | 50 | 100 | 100 | 98 | 100 | 95 |
| | 0.25 | PPI | 60 | 98 | 100 | 100 | 98 | 90 | 100 | 60 | 95 | 90 | 100 | 100 | 100 | 100 |
| | 0.50 | PPI | 90 | 100 | 100 | 98 | 100 | 95 | 100 | 100 | 100 | 100 | 100 | 100 | 100 | 100 |
| | 1.00 | PPI | 95 | 100 | 100 | 98 | 100 | 100 | 100 | 100 | 100 | 100 | 100 | 100 | 100 | 100 |
| 37 | 0.25 | SA | 0 | 0 | 0 | 0 | 80 | 60 | 0 | 0 | 10 | 90 | 70 | 50 | 50 | 70 |
| | 0.50 | SA | 30 | 20 | 20 | 50 | 100 | 98 | 0 | 20 | 20 | 100 | 98 | 100 | 100 | 100 |
| | 1.00 | SA | 70 | 50 | 20 | 95 | 100 | 98 | 50 | 95 | 90 | 100 | 100 | 100 | 100 | 100 |
| 38 | 0.062 | PPI | 0 | 0 | 10 | 0 | 0 | 30 | 20 | 0 | 0 | 50 | 40 | 30 | 30 | 70 |
| | 0.125 | PPI | 0 | 0 | 100 | 80 | 30 | 60 | 98 | 30 | 10 | — | 100 | 20 | 40 | 90 |
| | 0.25 | PPI | 20 | 40 | 100 | 98 | 98 | 90 | 100 | 50 | 50 | 100 | 100 | 100 | 100 | 100 |
| | 0.25 | PPI | 0 | 20 | 100 | 100 | 60 | 70 | 100 | 95 | 80 | 70 | 100 | 90 | 90 | 98 |
| | 0.50 | PPI | 90 | 100 | 100 | 100 | 100 | 95 | 100 | 100 | 100 | 100 | 100 | 100 | 100 | 100 |
| | 1.00 | PPI | 90 | 100 | 100 | 100 | 100 | 98 | 100 | 100 | 100 | 100 | 100 | 100 | 100 | 100 |
| 38 | 0.25 | SA | 0 | 0 | 0 | 0 | 50 | 90 | 0 | 0 | 0 | 80 | 70 | 50 | 100 | 90 |
| | 0.50 | SA | 0 | 0 | 10 | 20 | 100 | 95 | 10 | 10 | 10 | 100 | 95 | 100 | 100 | 90 |
| | 1.00 | SA | 70 | 70 | 70 | 80 | 100 | 100 | 70 | 80 | 70 | 100 | 100 | 100 | 100 | 100 |
| 40 | 0.062 | PPI | 0 | 0 | 30 | | 0 | 40 | 30 | 0 | 0 | 20 | 60 | 30 | 30 | 98 |
| | 0.125 | PPI | 0 | 20 | 70 | 40 | 50 | 80 | 98 | 30 | 20 | 95 | 100 | 90 | 100 | 100 |
| | 0.25 | PPI | 30 | 50 | 100 | 100 | 100 | 100 | 100 | 70 | 40 | 100 | 100 | 100 | 100 | 100 |
| | 0.25 | PPI | 0 | 20 | 98 | 60 | 95 | 95 | 100 | 80 | 20 | 100 | 100 | 100 | 100 | 100 |
| | 0.50 | PPI | 70 | 90 | 100 | 98 | 100 | 100 | 100 | 100 | 80 | 100 | 100 | 100 | 100 | 100 |
| | 1.00 | PPI | 70 | 100 | 100 | 100 | 100 | 100 | 100 | 100 | 100 | 100 | 100 | 100 | 100 | 100 |
| 40 | 0.25 | SA | 30 | 0 | 10 | 0 | 98 | 70 | 10 | 0 | 0 | 100 | 40 | 80 | 98 | 100 |
| | 0.50 | SA | 70 | 80 | 60 | 0 | 98 | 90 | 90 | 60 | 20 | 100 | 98 | 100 | 100 | 100 |
| | 1.00 | SA | 90 | 98 | 98 | 95 | 100 | 98 | 100 | 90 | 30 | 100 | 100 | 100 | 100 | 100 |
| 41 | 0.062 | PPI | 0 | 0 | 0 | 50 | 20 | 70 | 0 | 10 | 0 | 60 | 30 | 30 | 70 | 100 |
| | 0.125 | PPI | 0 | 0 | 80 | 60 | 60 | 50 | 95 | 10 | 10 | 90 | 100 | 80 | 90 | 100 |
| | 0.25 | PPI | 20 | 0 | 95 | 70 | 90 | 80 | 100 | 30 | 0 | 100 | 100 | 80 | 100 | 100 |
| | 0.25 | PPI | 0 | 20 | 98 | 90 | 100 | 40 | 30 | 100 | 100 | 100 | 100 | 100 | | |
| | 0.50 | PPI | 50 | 80 | 100 | 100 | 100 | 100 | 100 | 100 | 50 | 10 | 100 | 100 | 100 | 100 |
| | 1.00 | PPI | 98 | 100 | 100 | 100 | 100 | 98 | 100 | 100 | 100 | 100 | 100 | 100 | 100 | 100 |
| 41 | 0.25 | SA | 0 | 0 | 0 | 0 | 30 | 0 | 0 | 0 | 0 | 100 | 30 | 0 | 0 | 100 |
| | 0.50 | SA | 20 | 0 | 0 | 0 | 90 | 40 | 10 | 10 | 0 | 100 | 40 | 90 | 50 | 100 |
| | 1.00 | SA | 60 | 10 | 20 | 30 | 98 | 95 | 30 | 30 | 0 | 100 | 98 | 98 | 100 | 100 |
| 42 | 0.25 | PPI | 0 | 0 | 95 | 0 | 70 | 95 | 70 | 0 | 0 | 100 | 100 | 60 | 100 | 100 |
| | 0.50 | PPI | 0 | 0 | 90 | 30 | 40 | 90 | 100 | 50 | 10 | 100 | 100 | 40 | 100 | 100 |
| | 1.00 | PPI | 20 | 50 | 100 | 80 | 100 | 98 | 100 | 90 | 40 | 100 | 100 | 100 | 100 | 100 |
| 42 | 0.25 | SA | 10 | 0 | 0 | 0 | 20 | 30 | 0 | 0 | 0 | 80 | 0 | 0 | 0 | 100 |
| | 0.50 | SA | 70 | 20 | 10 | 0 | 98 | 98 | 0 | 0 | 0 | 100 | 0 | 70 | 30 | 100 |
| | 1.00 | SA | 70 | 50 | 20 | 0 | 100 | 40 | 20 | 20 | 20 | 100 | 100 | 100 | 0 | 100 |
| 43 | 0.062 | PPI | 0 | 0 | 0 | 0 | 0 | 0 | 20 | 0 | 0 | 0 | 30 | 0 | 80 | 80 |
| | 0.125 | PPI | 0 | 0 | 60 | 30 | 0 | 20 | 20 | 0 | 0 | 98 | 100 | 20 | 100 | 100 |
| | 0.25 | PPI | 0 | 0 | 98 | 40 | 80 | 80 | 98 | 70 | 10 | 100 | 100 | 80 | 100 | — |
| | 0.25 | PPI | 0 | 0 | 98 | 70 | 20 | 50 | 95 | 0 | 0 | 90 | 100 | 60 | 100 | 100 |
| | 0.50 | PPI | 30 | 80 | 100 | 80 | 100 | 100 | 100 | 100 | 40 | 100 | 100 | 100 | 100 | — |
| | 1.00 | PPI | 80 | 100 | 100 | 100 | 100 | 98 | 100 | 100 | 80 | 100 | 100 | 100 | 100 | — |
| 43 | 0.25 | SA | 0 | 0 | 0 | 0 | 0 | 50 | 0 | 50 | 0 | 98 | 40 | 20 | 30 | — |
| | 0.50 | SA | 0 | 0 | 0 | 0 | 60 | 50 | 0 | 70 | 0 | 100 | 50 | 80 | 90 | — |
| | 1.00 | SA | 10 | 30 | 0 | 20 | 98 | 80 | 20 | 80 | 0 | 100 | 80 | 98 | 98 | — |
| 44 | 0.062 | PPI | 0 | 0 | 10 | 0 | 0 | 0 | 0 | 20 | 0 | 60 | 30 | 30 | 0 | 98 |
| | 0.125 | PPI | 0 | 0 | 90 | 0 | 0 | 40 | 60 | 40 | 0 | 60 | 98 | 30 | 30 | 98 |
| | 0.25 | PPI | 10 | 0 | 98 | 40 | 30 | 20 | 80 | 40 | 20 | 95 | 100 | 40 | 100 | 100 |
| | 0.25 | PPI | 10 | 0 | 100 | 90 | 70 | 60 | 100 | 70 | 40 | 90 | 100 | 60 | 98 | 100 |
| | 0.50 | PPI | 30 | 20 | 100 | 98 | 100 | 100 | 100 | 98 | 98 | 100 | 100 | 100 | 100 | 100 |
| | 1.00 | PPI | 80 | 100 | 100 | 100 | 100 | 98 | 100 | 100 | 100 | 100 | 100 | 100 | 100 | 100 |
| 44 | 0.50 | SA | 0 | 0 | 0 | 0 | 70 | 80 | 0 | 0 | 0 | 98 | 40 | 40 | 98 | 98 |
| | 1.00 | SA | 20 | 0 | 0 | 0 | 95 | 95 | 10 | 0 | 0 | 100 | 95 | 70 | 100 | 100 |
| | 2.00 | SA | 50 | 30 | 20 | 0 | 100 | 95 | 10 | 20 | 0 | 100 | 95 | 100 | 100 | 100 |
| 45 | 0.062 | PPI | 0 | 0 | 40 | 0 | 0 | 0 | 0 | 0 | 0 | 50 | 50 | 20 | 90 | 60 |
| | 0.125 | PPI | 20 | 0 | 98 | 60 | 80 | 30 | 90 | 20 | 30 | 98 | 100 | 70 | 100 | 100 |
| | 0.25 | PPI | 30 | 0 | 100 | 98 | 100 | 100 | 100 | 95 | 98 | 100 | 100 | 98 | 100 | 100 |

TABLE V-continued

PREEMERGENCE HERBICIDE TESTING
PERCENT CROP INJURY OR WEED CONTROL

| Compound of Example No. | Application Rate lbs/A | App. | A | U | D | G | V | J | P | C | B | N | S | Q | R | X |
|---|---|---|---|---|---|---|---|---|---|---|---|---|---|---|---|---|
| | 0.25 | PPI | 40 | 50 | 100 | 98 | 100 | 100 | 100 | 90 | 80 | 100 | 100 | 100 | 100 | 100 |
| | 0.50 | PPI | 80 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 45 | 0.062 | SA | 0 | 0 | 0 | 0 | 0 | 0 | 0 | 0 | 0 | 50 | 0 | 0 | 0 | 0 |
| | 0.125 | SA | 0 | 0 | 0 | 0 | 0 | 0 | 0 | 0 | 0 | 80 | 30 | 20 | 50 | 80 |
| | 0.25 | SA | 0 | 0 | 10 | 0 | 100 | 80 | 0 | 0 | 0 | 98 | 40 | 98 | 70 | 100 |
| | 0.25 | SA | 0 | 0 | 30 | 40 | 80 | 50 | 20 | 20 | 20 | 98 | 95 | 80 | 60 | 100 |
| | 0.50 | SA | 10 | 20 | 10 | 40 | 100 | 100 | 0 | 0 | 0 | 100 | 80 | 100 | 100 | 100 |
| | 1.00 | SA | 98 | 98 | 80 | 100 | 100 | 100 | 80 | 80 | 80 | 100 | 100 | 100 | 100 | 100 |
| 46 | 0.062 | PPI | 0 | 0 | 40 | 0 | 20 | 20 | 40 | 20 | 0 | 40 | 50 | 20 | 90 | 50 |
| | 0.125 | PPI | 0 | 0 | 100 | 30 | 70 | 30 | 80 | 20 | 20 | 90 | 100 | 80 | 100 | 80 |
| | 0.25 | PPI | 50 | 40 | 100 | 100 | 100 | 100 | 90 | 100 | 100 | 98 | 100 | 98 | 100 | 100 |
| | 0.25 | PPI | 40 | 50 | 100 | 90 | 100 | 95 | 100 | 80 | 80 | 100 | 100 | 100 | 100 | 100 |
| | 0.50 | PPI | 80 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 46 | 0.062 | SA | 0 | 0 | 0 | 0 | 0 | 0 | 0 | 0 | 0 | 60 | 60 | 20 | 0 | 60 |
| | 0.125 | SA | 0 | 0 | 0 | 0 | 0 | 0 | 0 | 0 | 0 | 95 | 60 | 40 | 20 | 98 |
| | 0.25 | SA | 0 | 0 | 10 | 0 | 100 | 98 | 10 | 0 | 10 | 100 | 95 | 100 | 98 | 100 |
| | 0.25 | SA | 50 | 30 | 30 | 50 | 100 | 70 | 70 | 60 | 40 | 100 | 60 | 100 | 50 | 100 |
| | 0.50 | SA | 50 | 40 | 20 | 50 | 100 | 98 | 10 | 0 | 20 | 100 | 100 | 100 | 98 | 100 |
| | 1.00 | SA | 80 | 70 | 30 | 80 | 100 | 100 | 30 | 20 | 30 | 100 | 100 | 100 | 100 | 100 |
| 47 | 0.062 | PPI | 30 | 50 | 20 | 40 | 0 | 0 | 50 | 0 | 0 | 30 | 40 | 0 | 100 | 50 |
| | 0.125 | PPI | 10 | 20 | 90 | 40 | 20 | 20 | 95 | 0 | 0 | 100 | 98 | 30 | 100 | 98 |
| | 0.25 | PPI | 0 | 0 | 100 | 70 | 98 | 98 | 100 | 80 | 20 | 100 | 100 | 100 | 100 | — |
| | 0.25 | PPI | 10 | 10 | 100 | 90 | 80 | 90 | 100 | 30 | 40 | 100 | 100 | 80 | 100 | 100 |
| | 0.50 | PPI | 30 | 98 | 100 | 100 | 100 | 100 | 100 | 100 | 98 | 100 | 100 | 100 | 100 | — |
| | 1.00 | PPI | 95 | 100 | 100 | 100 | 100 | 100 | 100 | 100 | 100 | 100 | 100 | 100 | 100 | — |
| 47 | 0.25 | SA | 0 | 0 | 0 | 60 | 30 | 70 | 0 | 0 | 0 | 98 | 40 | 30 | 80 | — |
| | 0.50 | SA | 20 | 10 | 0 | 20 | 100 | 90 | 0 | 10 | 0 | 100 | 80 | 100 | 100 | — |
| | 1.00 | SA | 50 | 70 | 10 | 30 | 100 | 98 | 0 | 10 | 0 | 100 | 98 | 100 | 100 | — |
| 48 | 0.062 | PPI | 0 | 0 | 20 | 0 | 0 | 0 | 0 | 0 | 0 | 30 | 60 | 20 | 80 | 80 |
| | 0.125 | PPI | 10 | 10 | 90 | 50 | 0 | 20 | 98 | 20 | 10 | 80 | 100 | 30 | 100 | 100 |
| | 0.25 | PPI | 10 | 10 | 100 | 95 | 100 | 95 | 100 | 30 | 40 | 100 | 100 | 100 | 100 | 100 |
| | 0.25 | PPI | 0 | 30 | 100 | 90 | 100 | 98 | 100 | 90 | 20 | 100 | 100 | 100 | 100 | — |
| | 0.50 | PPI | 30 | 100 | 100 | 100 | 100 | 100 | 100 | 100 | 95 | 100 | 100 | 100 | 100 | — |
| | 1.00 | PPI | 90 | 100 | 100 | 100 | 100 | 100 | 100 | 100 | 100 | 100 | 100 | 100 | 100 | — |
| 48 | 0.25 | SA | 0 | 0 | 0 | 0 | 60 | 50 | 0 | 0 | 0 | 100 | 50 | 70 | 95 | — |
| | 0.50 | SA | 20 | 0 | 0 | 30 | 100 | 80 | 0 | 10 | 20 | 100 | 60 | 98 | 80 | — |
| | 1.00 | SA | 80 | 80 | 20 | 40 | 100 | 100 | 70 | 100 | 40 | 100 | 100 | 100 | 100 | — |
| 50 | 0.25 | PPI | 0 | 0 | 100 | 70 | 100 | 98 | 100 | 80 | 10 | 100 | 100 | 100 | 100 | — |
| | 0.50 | PPI | 40 | 98 | 100 | 95 | 100 | 100 | 100 | 100 | 90 | 100 | 100 | 100 | 100 | — |
| | 1.00 | PPI | 90 | 100 | 100 | 100 | 100 | 100 | 100 | 100 | 100 | 100 | 100 | 100 | 100 | — |
| 50 | 0.25 | SA | 0 | 0 | 0 | 30 | 30 | 0 | 0 | 0 | 0 | 100 | 50 | 70 | 98 | — |
| | 0.50 | SA | 10 | 0 | 0 | 30 | 100 | 90 | 30 | 10 | 0 | 100 | 98 | 100 | 100 | — |
| | 1.00 | SA | 40 | 80 | 20 | 50 | 100 | 90 | 70 | 10 | 0 | 100 | 100 | 100 | 100 | — |
| 51 | 0.125 | PPI | 0 | 0 | 0 | 0 | 0 | 30 | 0 | 0 | 0 | 20 | 30 | 70 | 0 | 80 |
| | 0.25 | PPI | 0 | 0 | 90 | 0 | 50 | 60 | 100 | 20 | 10 | 95 | 98 | 40 | 100 | 100 |
| | 0.50 | PPI | 0 | 60 | 100 | 70 | 100 | 98 | 100 | 60 | 30 | 100 | 100 | 100 | 100 | 100 |
| 51 | 0.125 | SA | 0 | 0 | 0 | 0 | 20 | 0 | 0 | 0 | 0 | 80 | 0 | 70 | 0 | 90 |
| | 0.25 | SA | 10 | 0 | 0 | 0 | 10 | 20 | 20 | 0 | 0 | 100 | 50 | 80 | 20 | 98 |
| | 0.50 | SA | 20 | 10 | 0 | 80 | 40 | 98 | 20 | 10 | 0 | 100 | 60 | 50 | 100 | 100 |
| 52 | 0.125 | PPI | 0 | 0 | 0 | 0 | 0 | 30 | 0 | 0 | 0 | 20 | 20 | 30 | 40 | 90 |
| | 0.25 | PPI | 0 | 0 | 90 | 40 | 30 | 70 | 95 | 10 | 0 | 50 | 90 | 50 | 100 | 100 |
| | 0.50 | PPI | 0 | 80 | 100 | 80 | 100 | 98 | 100 | 70 | 40 | 100 | 100 | 100 | 100 | 100 |
| 52 | 0.125 | SA | 0 | 0 | 0 | 0 | 0 | 20 | 0 | 0 | 0 | 60 | 0 | 50 | 50 | 50 |
| | 0.25 | SA | 0 | 0 | 0 | 10 | 20 | 90 | 0 | 0 | 0 | 80 | 90 | 50 | 70 | 90 |
| | 0.50 | SA | 0 | 0 | 0 | 30 | 90 | 95 | 20 | 10 | 40 | 100 | 100 | 100 | 100 | 100 |
| 53 | 0.125 | PPI | 0 | 0 | 20 | 0 | 10 | 0 | 0 | 0 | 0 | 0 | 60 | 60 | 20 | 80 |
| | 0.25 | PPI | 0 | 20 | 100 | 0 | 30 | 30 | 100 | 10 | 0 | 98 | 100 | 80 | 100 | 100 |
| | 0.50 | PPI | 10 | 40 | 100 | 80 | 100 | 90 | 100 | 80 | 30 | 100 | 100 | 100 | 100 | 100 |
| 53 | 0.125 | SA | 0 | 0 | 0 | 0 | 0 | 20 | 0 | 0 | 0 | 98 | 0 | 10 | 60 | 50 |
| | 0.25 | SA | 0 | 0 | 0 | 0 | 0 | 30 | 10 | 0 | 0 | 100 | 0 | 50 | 30 | 90 |
| | 0.50 | SA | 0 | 0 | 0 | 0 | 70 | 70 | 10 | 0 | 0 | 100 | 0 | 70 | 80 | 100 |
| 54 | 0.062 | PPI | 0 | 0 | 20 | 0 | 10 | 0 | 0 | 0 | 0 | 0 | 100 | 0 | 30 | 0 |
| | 0.125 | PPI | 0 | 0 | 50 | 10 | 20 | 0 | 0 | 30 | 10 | 98 | 100 | 60 | 100 | 90 |
| | 0.25 | PPI | 30 | 98 | 100 | 100 | 100 | 98 | 100 | 80 | 80 | 100 | 100 | 100 | 100 | 100 |
| 54 | 0.25 | PPI | 0 | 0 | 100 | 60 | 100 | 60 | 98 | 40 | 40 | 100 | 100 | 100 | 100 | 100 |
| | 0.50 | PPI | 98 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 54 | 0.25 | SA | 0 | 0 | 0 | 50 | 98 | 40 | 10 | 50 | 0 | 100 | 40 | 95 | 90 | 100 |
| | 0.50 | SA | 90 | 80 | 40 | 95 | 100 | 98 | 98 | 95 | 30 | 100 | 80 | 100 | 100 | 100 |
| | 1.00 | SA | 100 | 100 | 70 | 100 | 100 | 100 | 98 | 100 | 70 | 100 | 90 | 100 | 100 | 100 |
| 55 | 0.062 | PPI | 0 | 0 | 0 | 0 | 0 | 0 | 0 | 0 | 0 | 0 | 0 | 0 | 0 | 0 |
| | 0.125 | PPI | 0 | 0 | 20 | 0 | 0 | 0 | 0 | 20 | 10 | 90 | 100 | 70 | 100 | 100 |
| | 0.25 | PPI | 30 | 50 | 100 | 98 | 98 | 90 | 100 | 30 | 40 | 100 | 100 | 100 | 100 | 100 |
| | 0.25 | PPI | 0 | 0 | 90 | 50 | 100 | 0 | 90 | 40 | 40 | 100 | 100 | 100 | 100 | 100 |

TABLE V-continued

PREEMERGENCE HERBICIDE TESTING
PERCENT CROP INJURY OR WEED CONTROL

| Compound of Example No. | Application Rate lbs/A | App. | A | U | D | G | V | J | P | C | B | N | S | Q | R | X |
|---|---|---|---|---|---|---|---|---|---|---|---|---|---|---|---|---|
| | 0.50 | PPI | 90 | 100 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 55 | 0.25 | SA | 0 | 0 | 10 | 60 | 98 | 0 | 0 | 10 | 10 | 100 | 30 | 70 | 90 | 98 |
| | 0.50 | SA | 50 | 40 | 20 | 90 | 100 | 80 | 30 | 40 | 40 | 100 | 50 | 90 | 100 | 100 |
| | 1.00 | SA | 98 | 98 | 90 | 100 | 100 | 100 | 98 | 100 | 70 | 100 | 95 | 100 | 100 | 100 |
| 56 | 0.062 | PPI | 0 | 0 | 10 | 10 | 0 | 0 | 0 | 0 | 0 | 0 | 60 | 0 | 70 | 40 |
| | 0.125 | PPI | 0 | 0 | 50 | 20 | 0 | 30 | 10 | 0 | 0 | 40 | 98 | 40 | 100 | 80 |
| | 0.25 | PPI | 0 | 0 | 100 | 100 | 100 | 50 | 100 | 60 | 60 | 100 | 100 | 98 | 100 | 100 |
| | 0.25 | PPI | 10 | 40 | 100 | 98 | 100 | 50 | 95 | 30 | 40 | 100 | 100 | 100 | 100 | 100 |
| | 0.50 | PPI | 40 | 98 | 100 | 100 | 100 | 100 | 100 | 100 | 100 | 100 | 100 | 100 | 100 | 100 |
| | 1.00 | PPI | 100 | 100 | 100 | 100 | 100 | 100 | 100 | 100 | 100 | 100 | 100 | 100 | 100 | 100 |
| 56 | 0.062 | SA | 0 | 0 | 0 | 0 | 0 | 0 | 0 | 0 | 0 | 0 | 0 | 0 | 0 | 0 |
| | 0.125 | SA | 0 | 0 | 0 | 0 | 0 | 0 | 0 | 0 | 0 | 70 | 0 | 0 | 90 | 98 |
| | 0.25 | SA | 0 | 0 | 0 | 0 | 100 | 50 | 0 | 0 | 0 | 100 | 0 | 95 | 100 | 100 |
| | 0.25 | SA | 0 | 0 | 0 | 10 | 40 | 40 | 0 | 20 | 0 | 100 | 80 | 80 | 100 | 100 |
| | 0.50 | SA | 0 | 0 | 0 | 60 | 100 | 100 | 0 | 20 | 10 | 100 | 80 | 100 | 100 | 100 |
| | 1.00 | SA | 0 | 0 | 0 | 100 | 100 | 100 | 80 | 30 | 10 | 100 | 40 | 100 | 100 | 100 |
| 57 | 0.062 | PPI | 0 | 0 | 10 | 10 | 0 | 20 | 10 | 0 | 0 | 60 | 70 | 0 | 90 | 70 |
| | 0.125 | PPI | 0 | 0 | 70 | 50 | 50 | 50 | 60 | 0 | 20 | 98 | 100 | 60 | 100 | 98 |
| | 0.25 | PPI | 0 | 0 | 100 | 70 | 98 | 40 | 40 | 0 | 20 | 100 | 100 | 100 | 100 | 100 |
| | 0.25 | PPI | 0 | 0 | 95 | 90 | 100 | 90 | 100 | 20 | 70 | 100 | 100 | 90 | 100 | 100 |
| | 0.50 | PPI | 10 | 30 | 100 | 98 | 95 | 100 | 30 | 90 | 100 | 100 | 100 | 100 | 100 | |
| | 1.00 | PPI | 40 | 100 | 100 | 100 | 100 | 100 | 100 | 100 | 100 | 100 | 100 | 100 | 100 | 100 |
| 57 | 0.25 | SA | 0 | 0 | 10 | 10 | 20 | 0 | 0 | 0 | 0 | 98 | 20 | 50 | 0 | 40 |
| | 0.50 | SA | 0 | 0 | 20 | 30 | 80 | 0 | 0 | 0 | 0 | 100 | 70 | 98 | 90 | 100 |
| | 1.00 | SA | 40 | 20 | 70 | 70 | 95 | 50 | 10 | 0 | 40 | 100 | 90 | 100 | 100 | 100 |
| 58 | 0.125 | PPI | 0 | 0 | 10 | 20 | 10 | 60 | 0 | 10 | 0 | 100 | 70 | 70 | 0 | 80 |
| | 0.25 | PPI | 0 | 20 | 90 | 20 | 60 | 80 | 100 | 10 | 0 | 100 | 100 | 70 | 100 | 100 |
| | 0.50 | PPI | 10 | 40 | 100 | 80 | 98 | 90 | 100 | 80 | 30 | 100 | 100 | 98 | 100 | 100 |
| 58 | 0.125 | SA | 0 | 0 | 0 | 0 | 10 | 20 | 0 | 0 | 0 | 100 | 20 | 50 | 70 | 100 |
| | 0.25 | SA | 0 | 0 | 10 | 0 | 30 | 80 | 0 | 0 | 0 | 100 | 50 | 70 | 80 | 100 |
| | 0.50 | SA | 20 | 0 | 10 | 20 | 95 | 95 | 50 | 20 | 0 | 100 | 100 | 100 | 100 | 100 |
| 59 | 0.125 | PPI | 0 | 0 | 0 | 0 | 0 | 0 | 0 | 0 | 0 | 30 | 20 | 40 | 0 | 100 |
| | 0.25 | PPI | 0 | 0 | 80 | 30 | 10 | 80 | 50 | 10 | 0 | 70 | 90 | 80 | 100 | 100 |
| | 0.50 | PPI | 0 | 20 | 100 | 40 | 90 | 80 | 100 | 50 | 20 | 100 | 100 | 98 | 100 | 100 |
| 59 | 0.125 | SA | 0 | 0 | 0 | 20 | 0 | 20 | 0 | 0 | 0 | 90 | 0 | 70 | 40 | 100 |
| | 0.25 | SA | 0 | 0 | 0 | 30 | 0 | 80 | 0 | 0 | 0 | 95 | 40 | 70 | 98 | 100 |
| | 0.50 | SA | 40 | 10 | 10 | 40 | 60 | 90 | 50 | 40 | 10 | 100 | 100 | 100 | 100 | 100 |
| 60 | 0.125 | PPI | 0 | 10 | 70 | 0 | 0 | 0 | 20 | 0 | 0 | 90 | 100 | 10 | 98 | 100 |
| | 0.25 | PPI | 20 | 80 | 100 | 95 | 100 | 100 | 100 | 80 | 50 | 100 | 100 | 100 | 100 | 100 |
| | 0.50 | PPI | 70 | 100 | 100 | 80 | 98 | 90 | 100 | 100 | 98 | 100 | 100 | 98 | 100 | 100 |
| 60 | 0.25 | SA | 0 | 0 | 0 | 30 | 50 | 50 | 0 | 10 | 0 | 80 | 20 | 60 | 10 | 100 |
| | 0.50 | SA | 0 | 0 | 10 | 30 | 95 | 80 | 0 | 10 | 0 | 98 | 100 | 98 | 80 | 100 |
| | 1.00 | SA | 40 | 10 | 10 | 50 | 100 | 80 | 20 | 20 | 0 | 98 | 100 | 100 | 80 | 100 |
| 61 | 0.125 | PPI | 0 | 10 | 50 | 60 | 60 | 40 | 20 | 0 | 0 | 100 | 100 | 60 | 100 | 100 |
| | 0.25 | PPI | 10 | 30 | 100 | 80 | 98 | 70 | 100 | 40 | 20 | 100 | 100 | 98 | 100 | 100 |
| | 0.50 | PPI | 50 | 100 | 100 | 95 | 100 | 100 | 100 | 100 | 80 | 100 | 100 | 100 | 100 | 100 |
| 61 | 0.125 | SA | 0 | 0 | 0 | 0 | 0 | 0 | 0 | 0 | 0 | 50 | 0 | 20 | 0 | 90 |
| | 0.25 | SA | 0 | 0 | 0 | 40 | 10 | 20 | 0 | 0 | 0 | 60 | 30 | 20 | 80 | 100 |
| | 0.50 | SA | 20 | 10 | 0 | 30 | 50 | 30 | 10 | 0 | 0 | 100 | 60 | 90 | 90 | 100 |
| 63 | 0.125 | PPI | 0 | 0 | 60 | 0 | 0 | 0 | 30 | 0 | 0 | 100 | 100 | 30 | 100 | 100 |
| | 0.25 | PPI | 10 | 0 | 100 | 100 | 70 | 60 | 100 | 30 | 50 | 100 | 100 | 80 | 100 | 100 |
| | 0.50 | PPI | 40 | 90 | 100 | 98 | 100 | 100 | 100 | 70 | 98 | 100 | 100 | 100 | 100 | 100 |
| 63 | 0.25 | SA | 0 | 0 | 0 | 0 | 0 | 0 | 20 | 0 | 0 | 0 | 0 | 0 | 0 | 98 |
| | 0.50 | SA | 30 | 0 | 10 | 10 | 98 | 90 | 10 | 0 | 0 | 100 | 80 | 80 | 100 | 100 |
| | 1.00 | SA | 40 | 10 | 40 | 50 | 100 | 100 | 80 | 40 | 10 | 100 | 100 | 100 | 100 | 100 |

TABLE VI
POSTEMERGENCE HERBICIDE TESTING
PERCENT CROP INJURY OR WEED CONTROL

| Compound of Example No. | Application Rate lbs/A | A | U | G | J | D | P | V | L | B | C | F | Z | R | S | M | X | N | Y | Q | T |
|---|---|---|---|---|---|---|---|---|---|---|---|---|---|---|---|---|---|---|---|---|---|
| 1 | 0.062 | 15 | 30 | 30 | 0 | 15 | 15 | 60 | 50 | 50 | 50 | 80 | 0 | 50 | 80 | 50 | 0 | 40 | 50 | 40 | 90 |
|   | 0.125 | 10 | 10 | 10 | 10 | 20 | 10 | 60 | 10 | 100 | 20 | 100 | 50 | 90 | 80 | 80 | 98 | 95 | 95 | 90 | 100 |
|   | 0.13 | 25 | 40 | 30 | 10 | 25 | 15 | 70 | 60 | 50 | 80 | 60 | 0 | 80 | 70 | 70 | 30 | 60 | 100 | 50 | 80 |
|   | 0.25 | 50 | 20 | 30 | 10 | 20 | 40 | 80 | 10 | 100 | 90 | 100 | 70 | 100 | 90 | 98 | 90 | 95 | 100 | — | 100 |
|   | 0.25 | 30 | 40 | 30 | 10 | 25 | 30 | 90 | 80 | 100 | 90 | 100 | 50 | 90 | 95 | 90 | 30 | 50 | 100 | 100 | 90 |
|   | 0.50 | 30 | 50 | 30 | 40 | 30 | 50 | 100 | 90 | 100 | 90 | 100 | 80 | 100 | 95 | 100 | 95 | 95 | 100 | 98 | 100 |
| 2 | 0.13 | 10 | 0 | 10 | 10 | 0 | 20 | 30 | 30 | 20 | 30 | 20 | — | 80 | 40 | 50 | 0 | 0 | 10 | 30 | 90 |
|   | 0.25 | 20 | 10 | 20 | 10 | 0 | 20 | 50 | 70 | 30 | 95 | — | 10 | 100 | 90 | 70 | 50 | 20 | 10 | 30 | 100 |
|   | 0.50 | 20 | 0 | 20 | 5 | 20 | 60 | 50 | 90 | 100 | 100 | 50 | 100 | 100 | 90 | 0 | 0 | 10 | 40 | 60 | 90 |
|   | 1.00 | 100 | 0 | 0 | 30 | 5 | 30 | 60 | 50 | 100 | 20 | — | — | 100 | 100 | 95 | 0 | 40 | 80 | 80 | 80 |
| 5 | 0.062 | 0 | 0 | 0 | 0 | 0 | 0 | 0 | 10 | 0 | 20 | 20 | 20 | 0 | 0 | 0 | 10 | 60 | 10 | 60 | 20 |
|   | 0.13 | 0 | 0 | 5 | 10 | 0 | 10 | 5 | 0 | 10 | 40 | 50 | 20 | 5 | 0 | 20 | 20 | 95 | 40 | 70 | 20 |
|   | 0.25 | 5 | 0 | 0 | 0 | 5 | 0 | 10 | 20 | 30 | 60 | 70 | 80 | 10 | 40 | 50 | 50 | 95 | 60 | 60 | 40 |
|   | 0.50 | 0 | 20 | 10 | 10 | 5 | 10 | 20 | 40 | 40 | 80 | 90 | 90 | 40 | 60 | 70 | 80 | 95 | 90 | 90 | 70 |
| 7 | 0.13 | 0 | 30 | 30 | 0 | 20 | 20 | 60 | 50 | 100 | 90 | 80 | 30 | 80 | 90 | 0 | 20 | 0 | 50 | 20 | 40 |
|   | 0.25 | 0 | 30 | 30 | 10 | 30 | 10 | 80 | 95 | 90 | 100 | 100 | 50 | 100 | 100 | 60 | 50 | 0 | 100 | 30 | 100 |
|   | 0.50 | 30 | 40 | 40 | 15 | 40 | 20 | 90 | 50 | 100 | 90 | 80 | 50 | 100 | 70 | 80 | 80 | 40 | 100 | 95 | 100 |
|   | 1.00 | 20 | 70 | 30 | 30 | 30 | 40 | 95 | 50 | 100 | 100 | 80 | 60 | 100 | 90 | 95 | 90 | 20 | 80 | 100 | 80 |
| 8 | 0.13 | 30 | 25 | 20 | 50 | 30 | 40 | 98 | 95 | 100 | 100 | 100 | 80 | 100 | 100 | 100 | 100 | 90 | 100 | 100 | 100 |
|   | 0.25 | 20 | 50 | 30 | 90 | 50 | 80 | 95 | 50 | 100 | 90 | 100 | 90 | 100 | 70 | 20 | 20 | 0 | 0 | 0 | 30 |
|   | 0.50 | 30 | 80 | 80 | 80 | 60 | 20 | 100 | 100 | 100 | 100 | 100 | 80 | 100 | 100 | 90 | 50 | 20 | 20 | 60 | 50 |
|   | 1.00 | 100 | 90 | 20 | 0 | 20 | 20 | 30 | 30 | 50 | 60 | 40 | 60 | 20 | 30 | 20 | 50 | 50 | 30 | 80 | 20 |
| 9 | 0.25 | 30 | 0 | 20 | 0 | 0 | 40 | 40 | 40 | 100 | 80 | 60 | 80 | 30 | 40 | 40 | 50 | 0 | 0 | 95 | 20 |
|   | 0.50 | 30 | 20 | 30 | 0 | 0 | 50 | 80 | 50 | 100 | 100 | 80 | 20 | 60 | 50 | 85 | 80 | 0 | 20 | 0 | 85 |
|   | 1.00 | 100 | 35 | 0 | 40 | 0 | 0 | 0 | 0 | 0 | 10 | 10 | 10 | 0 | 0 | 0 | 0 | 0 | 30 | 0 | 100 |
| 14 | 0.13 | 0 | 0 | 5 | 0 | 0 | 10 | 5 | 0 | 0 | 20 | 10 | 20 | 0 | 30 | 50 | 10 | 0 | 20 | 0 | 40 |
|   | 0.25 | 0 | 0 | 0 | 0 | 5 | 10 | 10 | 80 | 10 | 0 | 0 | 50 | 0 | 50 | 100 | 0 | 0 | 70 | 0 | 30 |
|   | 0.50 | 10 | 10 | 20 | 5 | 10 | 10 | 20 | 30 | 10 | 80 | 80 | 100 | 10 | 100 | 100 | 60 | 0 | 100 | 20 | 50 |
| 19 | 0.13 | 15 | 0 | 10 | 10 | 10 | 0 | 40 | 60 | 80 | 80 | 70 | 90 | 20 | 60 | 60 | 40 | 30 | 100 | 10 | 20 |
|   | 0.25 | 30 | 15 | 30 | 20 | 10 | 10 | 50 | 70 | 100 | 100 | 80 | 80 | 50 | 85 | 70 | 60 | 40 | 70 | 70 | 85 |
|   | 0.50 | 40 | 30 | 35 | 10 | 10 | 5 | 60 | 20 | 100 | 100 | 80 | 80 | 100 | 100 | 90 | 70 | 30 | 100 | 95 | 100 |
|   | 1.00 | 30 | 40 | 20 | 50 | 15 | 10 | 15 | 40 | 60 | 100 | 80 | 70 | 20 | 60 | 95 | 40 | 40 | 80 | 95 | 40 |
| 20 | 0.13 | 30 | 40 | 20 | 10 | 10 | 0 | 40 | 90 | 100 | 100 | 100 | 80 | 50 | 85 | 98 | 80 | 30 | 100 | 100 | 100 |
|   | 0.25 | 40 | 40 | 35 | 50 | 15 | 40 | 80 | 40 | 60 | 100 | 100 | 80 | 100 | 100 | 30 | 80 | 30 | 70 | 50 | 30 |
|   | 0.50 | 40 | 0 | 40 | 100 | 10 | 40 | 100 | 98 | 100 | 100 | 100 | 70 | 95 | 50 | 50 | 30 | 90 | 100 | 60 | 50 |
| 21 | 0.13 | 0 | 0 | 15 | 0 | 10 | 0 | 50 | 15 | 60 | 50 | 70 | 80 | 0 | 60 | 60 | 0 | 20 | 80 | 80 | 20 |
|   | 0.25 | 10 | 15 | 15 | 20 | 15 | 15 | 85 | 50 | 100 | 100 | 80 | 90 | 50 | 90 | 50 | — | 30 | 100 | 100 | 90 |
|   | 0.50 | 20 | 15 | 20 | 15 | 15 | 15 | 85 | 50 | 100 | 100 | 80 | 90 | 100 | 98 | 60 | — | 50 | 100 | 80 | 80 |
|   | 1.00 | 50 | 30 | 30 | 60 | 20 | 30 | 100 | 80 | 100 | 100 | 90 | 90 | 100 | 85 | 70 | 0 | 70 | 100 | 100 | 100 |
| 22 | 0.25 | 0 | 40 | 20 | 40 | 30 | 15 | 30 | 50 | 50 | 100 | 100 | 90 | 60 | 90 | 100 | 0 | 60 | 100 | 100 | 80 |
|   | 0.50 | 15 | 30 | 20 | 10 | 15 | 5 | 30 | 20 | 100 | 100 | 100 | 90 | 80 | 100 | 70 | 0 | 50 | 100 | 80 | 40 |
|   | 1.00 | 40 | 30 | 30 | 30 | 15 | 10 | 30 | 90 | 100 | 100 | 100 | 90 | 90 | 80 | 90 | 0 | 60 | 100 | 50 | 70 |
|   | 2.00 | 40 | 30 | 20 | 40 | 30 | 15 | 40 | 50 | 100 | 100 | 100 | 80 | 90 | 80 | 100 | 0 | 30 | 100 | 90 | 80 |
| 23 | 1.00 | 0 | 0 | 0 | 0 | 0 | 0 | 0 | 20 | 0 | 10 | 0 | 0 | 0 | 0 | 0 | 30 | 0 | 0 | 0 | 40 |
|   | 2.00 | 0 | 0 | 10 | 0 | 0 | 0 | 20 | 40 | 20 | 15 | 20 | 20 | 50 | 30 | 50 | 50 | 0 | 10 | 20 | 30 |
|   | 4.00 | 0 | 0 | 10 | 10 | 0 | 0 | 60 | 40 | 20 | 20 | 90 | 30 | 30 | 80 | 70 | 50 | 0 | 30 | 20 | 40 |

TABLE VI-continued
POSTEMERGENCE HERBICIDE TESTING
PERCENT CROP INJURY OR WEED CONTROL

| Compound of Example No. | Application Rate lbs/A | A | U | G | J | D | P | V | L | B | C | F | Z | R | S | M | X | N | Y | Q | T |
|---|---|---|---|---|---|---|---|---|---|---|---|---|---|---|---|---|---|---|---|---|---|
| 24 | 0.13 | 10 | 40 | 30 | 30 | 20 | 10 | 40 | 40 | 100 | 80 | 100 | 90 | 100 | 90 | 50 | 0 | 40 | 100 | 20 | 20 |
|  | 0.25 | 30 | 30 | 40 | 30 | 35 | 30 | 70 | 40 | 100 | 90 | 100 | 20 | 100 | 100 | 90 | 0 | 30 | 100 | 50 | 100 |
|  | 0.50 | 60 | 50 | 50 | 50 | 40 | 50 | 60 | 70 | 100 | 100 | 100 | 50 | 100 | 95 | 100 | 0 | 30 | 100 | 85 | 100 |
|  | 1.00 | 60 | 80 | 60 | 60 | 60 | 50 | 100 | 80 | 100 | 100 | 100 | 100 | 50 | 100 | 100 | 20 | 60 | 100 | 100 | 100 |
| 25 | 0.062 | 0 | 30 | 20 | 0 | 10 | 0 | 40 | 0 | 30 | 100 | 30 | 10 | 80 | 35 | 50 | 30 | 30 | 80 | 50 | 50 |
|  | 0.13 | 0 | 50 | 20 | 0 | 10 | 0 | 90 | 20 | 100 | 100 | 100 | 40 | 100 | 60 | 50 | 50 | 40 | 100 | 70 | 50 |
|  | 0.25 | 30 | 50 | 50 | 10 | 20 | 15 | 95 | 30 | 100 | 80 | 100 | 50 | 100 | 70 | 60 | 50 | 90 | 100 | 95 | 80 |
|  | 0.50 | 30 | 90 | 50 | 40 | 30 | 30 | 100 | 60 | 100 | 100 | 100 | 30 | 100 | 80 | 60 | 90 | 95 | 100 | 100 | 80 |
| 26 | 1.00 | 0 | 10 | 0 | 0 | 0 | 0 | 0 | 0 | 20 | 15 | 30 | 20 | 70 | 15 | 85 | 90 | 60 | 0 | 0 | 30 |
|  | 2.00 | 0 | 10 | 30 | 0 | 0 | 0 | 40 | 30 | 20 | 20 | 50 | 30 | 100 | 20 | 95 | 30 | 60 | 30 | 30 | 40 |
|  | 4.00 | 15 | 0 | 20 | 40 | 0 | 20 | 80 | 40 | 40 | 20 | 50 | 20 | 50 | 50 | 30 | 50 | 10 | 50 | 30 | 80 |
| 27 | 0.062 | 0 | 20 | 60 | 0 | 10 | 0 | 10 | 30 | 20 | 30 | 50 | 50 | 90 | 60 | 50 | 50 | 30 | 80 | 60 | 60 |
|  | 0.13 | 10 | 10 | 10 | 0 | 15 | 10 | 50 | 40 | 40 | 25 | 50 | 70 | 100 | 85 | 80 | 60 | 30 | 100 | 70 | 50 |
|  | 0.25 | 35 | 35 | 40 | 10 | 30 | 30 | 80 | 70 | 100 | 90 | 60 | 50 | 100 | 50 | 50 | 60 | 70 | 100 | 50 | 50 |
|  | 0.50 | 0 | 50 | 40 | 20 | 30 | 30 | 100 | 80 | 100 | 100 | 90 | 60 | 100 | 90 | 95 | 30 | 90 | 100 | 60 | 85 |
| 28 | 0.062 | 0 | 0 | 0 | 0 | 0 | 0 | 0 | 0 | 60 | 20 | 80 | 100 | 80 | 50 | 50 | 30 | 80 | 80 | 60 | 50 |
|  | 0.125 | 10 | 10 | 10 | 0 | 10 | 10 | 10 | 40 | 95 | 20 | 80 | 80 | 60 | 90 | 80 | 80 | 60 | 90 | 60 | 95 |
|  | 0.25 | 0 | 10 | 10 | 10 | 10 | 10 | 40 | 50 | 100 | 40 | 80 | 95 | 100 | 90 | 95 | 60 | 80 | 100 | 100 | 100 |
|  | 0.50 | 50 | 30 | 40 | 10 | 20 | 20 | 60 | 95 | 100 | 98 | 80 | 70 | 100 | 95 | 95 | 20 | 80 | 100 | 100 | 90 |
| 29 | 0.062 | 0 | 0 | 0 | 0 | 0 | 0 | 0 | 0 | 60 | 10 | 90 | 95 | 100 | 80 | 80 | 50 | 80 | 30 | 40 | 80 |
|  | 0.125 | 0 | 0 | 10 | 0 | 10 | 10 | 30 | 30 | 90 | 30 | 100 | 95 | 100 | 95 | 80 | 30 | 80 | 90 | 60 | 100 |
|  | 0.25 | 10 | 10 | 15 | 10 | 10 | 10 | 30 | 60 | 100 | 40 | 100 | 80 | 100 | 98 | 90 | 20 | 80 | 100 | 70 | 50 |
|  | 0.50 | 20 | 60 | 20 | 10 | 30 | 40 | 20 | 80 | 20 | 70 | 80 | 100 | 100 | 50 | 95 | 50 | 80 | 50 | 80 | 80 |
| 30 | 0.50 | 40 | 50 | 20 | 30 | 40 | 10 | 30 | 30 | 80 | 100 | 90 | 50 | 100 | 80 | 100 | 30 | 70 | 30 | 30 | 100 |
|  | 1.00 | 60 | 70 | 30 | 70 | 20 | 40 | 60 | 60 | 100 | 100 | 90 | 80 | 100 | 80 | 40 | 20 | 70 | 100 | 100 | 30 |
|  | 2.00 | 0 | 100 | 40 | 0 | 30 | 50 | 100 | 98 | 100 | 100 | 90 | 100 | 100 | 60 | 80 | 98 | 70 | 100 | 100 | 30 |
| 31 | 1.00 | 10 | 0 | 10 | 0 | 0 | 0 | 0 | 0 | 20 | 35 | 100 | 95 | — | 60 | 50 | 0 | 0 | 50 | 0 | 30 |
|  | 2.00 | 0 | 0 | 15 | 0 | 0 | 0 | 0 | 0 | 80 | 100 | 70 | — | 40 | 60 | 80 | — | 30 | 30 | 30 | 30 |
|  | 4.00 | 10 | 0 | 20 | 20 | 15 | 10 | 30 | 10 | 100 | 100 | 80 | — | 60 | 60 | 60 | 30 | 20 | 100 | 60 | 40 |
| 32 | 0.13 | 10 | 30 | 20 | 60 | 20 | 20 | 20 | 20 | 100 | 20 | 80 | 40 | 20 | 95 | 40 | 50 | 0 | 100 | 30 | 100 |
|  | 0.25 | 10 | 20 | 30 | 80 | 30 | 30 | 30 | 30 | 80 | 50 | 90 | 60 | 80 | 100 | 80 | 70 | 20 | 100 | 80 | 100 |
|  | 0.50 | 20 | 30 | 30 | 98 | 0 | 40 | 40 | 50 | 100 | 50 | 90 | 20 | 80 | 80 | 70 | 80 | 0 | 100 | 20 | 100 |
| 34 | 0.25 | 10 | 0 | 80 | 80 | 0 | 10 | 100 | 40 | 100 | 70 | 80 | 80 | 80 | 80 | 100 | 100 | 0 | 40 | 20 | 100 |
|  | 0.50 | 20 | 0 | 80 | 80 | 0 | 40 | 100 | 80 | 100 | 70 | 90 | 100 | 100 | 80 | 100 | 100 | 0 | 40 | 20 | 100 |
|  | 1.00 | 40 | 0 | 95 | 80 | 0 | 60 | 100 | 98 | 100 | 70 | 80 | 100 | 100 | 90 | 100 | 100 | 50 | 20 | 80 | 100 |
|  | 2.00 | 0 | 0 | 20 | 98 | 0 | 0 | 100 | 60 | 100 | 80 | 80 | 70 | 20 | 98 | 100 | 100 | 60 | 40 | 80 | 100 |
| 36 | 0.062 | 50 | 0 | 20 | 80 | 20 | 20 | 40 | 50 | 50 | 95 | 80 | 90 | 95 | 20 | 30 | 100 | 70 | 30 | 90 | 100 |
|  | 0.125 | 80 | 10 | 80 | 70 | 50 | 30 | 100 | 60 | 60 | 98 | 80 | 95 | 98 | 100 | 50 | 100 | 100 | 20 | 100 | 100 |
|  | 0.25 | 0 | 20 | 60 | 98 | 50 | 20 | 100 | 10 | 90 | 70 | 80 | 60 | 70 | 60 | 100 | 100 | 80 | 40 | 80 | 100 |
|  | 0.50 | 80 | 40 | 50 | 70 | 60 | 70 | 100 | 98 | 100 | 95 | 100 | 98 | 80 | 100 | 100 | 98 | 100 | 98 | 90 | 100 |
|  | 1.00 | 30 | 80 | 60 | 100 | 80 | 80 | 100 | 60 | 80 | 98 | 100 | 70 | 80 | 60 | 100 | 98 | 100 | 100 | 100 | 100 |
| 37 | 0.125 | 0 | 40 | 50 | 20 | 40 | 30 | 50 | 60 | 70 | 60 | 100 | 70 | 80 | 50 | 80 | 100 | 10 | 50 | 40 | 100 |
|  | 0.25 | 0 | 60 | 50 | 60 | 50 | 50 | 70 | 50 | 70 | 50 | 100 | 80 | 90 | 70 | 80 | 100 | 80 | 80 | 50 | 100 |

TABLE VI-continued
POSTEMERGENCE HERBICIDE TESTING
PERCENT CROP INJURY OR WEED CONTROL

| Compound of Example No. | Application Rate lbs/A. | A | U | G | J | D | P | V | L | B | C | F | Z | R | S | M | X | N | Y | Q | T |
|---|---|---|---|---|---|---|---|---|---|---|---|---|---|---|---|---|---|---|---|---|---|
| | 0.50 | 40 | 98 | 30 | 98 | 70 | 70 | 100 | 90 | 95 | 70 | 100 | 20 | 100 | 100 | 100 | 98 | 100 | 100 | 80 | 100 |
| | 0.50 | 95 | 70 | 50 | 80 | 50 | 40 | 70 | 80 | 100 | 80 | 100 | 90 | 100 | 50 | 90 | 100 | 80 | 80 | 40 | 100 |
| | 1.00 | 98 | 98 | 50 | 100 | 70 | 80 | 100 | 90 | 98 | 70 | 100 | 50 | 100 | 100 | 100 | 100 | 100 | 100 | 80 | 100 |
| | 2.00 | 40 | 98 | 60 | 100 | 50 | 95 | 100 | 98 | 98 | 80 | 98 | 80 | 100 | 100 | 100 | 100 | 100 | 100 | 98 | 100 |
| 38 | 0.062 | 10 | 50 | 60 | 40 | 40 | 10 | 30 | 30 | 50 | 20 | 100 | 90 | 80 | 70 | 40 | 100 | 60 | 80 | 20 | 100 |
| | 0.125 | 10 | 40 | 60 | 60 | 40 | 60 | 70 | 40 | 90 | 40 | 98 | 100 | 90 | 80 | 60 | 100 | 80 | 80 | 60 | 100 |
| | 0.25 | 90 | 95 | 50 | 100 | 60 | 70 | 100 | 80 | 98 | 90 | 100 | 20 | 100 | 80 | 98 | 100 | 95 | 100 | 100 | 100 |
| | 0.50 | 40 | 50 | 80 | 60 | 80 | 70 | 80 | 80 | 95 | 80 | 100 | 100 | 100 | 80 | 90 | 100 | 100 | 100 | 100 | 100 |
| | 1.00 | 90 | 95 | 40 | 100 | 60 | 98 | 100 | 100 | 98 | 90 | 100 | 80 | 100 | 100 | 100 | 100 | 100 | 100 | 70 | 100 |
| | 0.25 | 95 | 95 | 80 | 100 | 70 | 98 | 100 | 80 | 100 | 98 | 100 | 100 | 60 | 100 | 100 | 100 | 100 | 70 | 100 | 100 |
| 40 | 0.25 | 0 | 30 | 0 | 30 | 60 | 20 | 100 | 100 | 50 | 30 | 100 | 30 | 50 | 95 | 100 | 50 | 0 | 70 | 10 | 100 |
| | 0.50 | 0 | 40 | 0 | 50 | 60 | 20 | 100 | 50 | 80 | 60 | 100 | 30 | 80 | 98 | 100 | 50 | 20 | 98 | 50 | 95 |
| | 1.00 | 10 | 20 | 70 | 70 | 60 | 50 | 100 | 98 | 90 | 80 | 100 | 50 | 80 | 60 | 100 | 50 | 20 | 50 | 70 | 95 |
| 43 | 0.062 | 0 | 0 | 40 | 40 | 20 | 30 | 98 | 20 | 40 | 60 | 100 | 30 | 98 | 95 | 70 | 98 | 70 | 0 | 40 | 98 |
| | 0.125 | 50 | 70 | 60 | 80 | 70 | 60 | 100 | 70 | 80 | 80 | 100 | 50 | — | 60 | 95 | 100 | 100 | 98 | 60 | 95 |
| | 0.25 | 50 | 50 | 70 | 80 | 50 | 50 | 100 | 98 | 95 | 80 | 100 | 50 | 100 | 100 | 80 | 70 | 30 | 100 | 98 | 98 |
| | 0.50 | 80 | 80 | 80 | 80 | 70 | 80 | 100 | 95 | 100 | 90 | 100 | 60 | — | 95 | 100 | 100 | 30 | 100 | 100 | 100 |
| | 1.00 | 80 | 90 | 80 | 100 | 70 | 90 | 100 | 80 | 95 | 100 | 100 | 40 | — | 100 | 100 | 70 | 100 | 100 | 100 | 100 |
| 45 | 0.062 | 80 | 30 | 80 | 80 | 30 | 30 | 70 | 100 | 40 | 40 | 100 | 60 | 95 | 100 | 80 | 80 | 30 | 30 | 30 | 100 |
| | 0.125 | 60 | 50 | 30 | 70 | 50 | 30 | 98 | 70 | 80 | 70 | 100 | 70 | 100 | 95 | 100 | 100 | 80 | 100 | 50 | 100 |
| | 0.25 | 0 | 90 | 50 | 70 | 40 | 40 | 90 | 80 | 95 | 60 | 100 | 90 | 95 | 90 | 100 | 50 | 90 | 100 | 80 | 100 |
| | 0.50 | 80 | 60 | 60 | 60 | 60 | 50 | 100 | 98 | 100 | 90 | 100 | 90 | 100 | 95 | 98 | 100 | 100 | 100 | 80 | 100 |
| | 1.00 | 60 | 95 | 80 | 90 | 60 | 95 | 100 | 98 | 100 | 90 | 100 | 100 | 95 | 90 | 100 | 60 | 100 | 100 | 100 | 100 |
| 46 | 0.50 | 0 | 95 | 98 | 70 | 60 | 100 | 70 | 98 | 100 | 100 | 100 | 100 | 50 | 20 | 98 | 98 | 80 | 30 | 0 | 80 |
| | 1.00 | 10 | 0 | 0 | 20 | 0 | 0 | 20 | 30 | 0 | 10 | 60 | 50 | 70 | 70 | 98 | 30 | 70 | 30 | 10 | 80 |
| | 2.00 | 30 | 0 | 10 | 20 | 10 | 0 | 90 | 50 | 0 | 20 | 100 | 30 | 90 | 70 | 98 | 100 | 95 | 50 | 50 | 100 |
| 47 | 0.062 | 50 | 10 | 10 | 40 | 40 | 10 | 100 | 50 | 20 | 30 | 100 | 30 | 80 | 70 | 80 | 30 | — | 90 | 40 | 80 |
| | 0.125 | 50 | 60 | 50 | 60 | 30 | 50 | 95 | 80 | 50 | 40 | 90 | 30 | 90 | 80 | 90 | 100 | — | 95 | 40 | 98 |
| | 0.25 | 40 | 70 | 50 | 80 | 20 | 60 | 98 | 70 | 20 | 40 | 100 | 30 | 90 | 95 | 80 | — | — | 90 | 90 | 100 |
| | 0.50 | 90 | 30 | 60 | 98 | 60 | 40 | 100 | 90 | 98 | 80 | 100 | 30 | 100 | 98 | 90 | — | — | 100 | 70 | 100 |
| | 1.00 | 60 | 80 | 70 | 98 | 70 | 80 | 100 | 80 | 98 | 95 | 100 | 80 | 90 | 50 | 100 | 98 | 100 | 100 | 80 | 100 |
| 48 | 0.50 | 40 | 90 | 70 | 98 | 80 | 60 | 100 | 80 | 100 | 98 | 100 | 100 | 90 | 20 | 98 | 30 | 80 | 30 | 80 | 100 |
| | 1.00 | 60 | 40 | 10 | 20 | 10 | 80 | 100 | 30 | 100 | 100 | 100 | 50 | 90 | 70 | 100 | 100 | 80 | 40 | 0 | 50 |
| | 2.00 | 40 | 0 | 50 | 40 | 10 | 10 | 80 | 50 | 0 | 10 | 60 | 30 | 90 | 70 | 70 | 80 | 50 | 40 | 20 | 50 |
| 50 | 0.50 | 30 | 50 | 50 | 60 | 30 | 20 | 95 | 50 | 20 | 20 | 100 | 50 | 80 | 80 | 90 | 80 | 40 | 70 | 0 | 80 |
| | 1.00 | 10 | 20 | 40 | 30 | 10 | 10 | 98 | 95 | 30 | 30 | 100 | 30 | 90 | 30 | 50 | 70 | 80 | 50 | 50 | 100 |
| | 2.00 | 20 | 20 | 60 | 60 | 30 | 60 | 100 | 70 | 98 | 10 | 100 | 30 | 95 | 70 | 80 | 100 | 70 | 80 | 30 | 80 |
| 51 | 0.125 | 20 | 50 | 80 | 90 | 20 | 40 | 100 | 80 | 100 | 20 | 100 | 80 | 98 | 90 | 80 | 100 | 90 | 50 | 40 | 100 |
| | 0.25 | 10 | 80 | 60 | 85 | 50 | 40 | 70 | 80 | 98 | 95 | 100 | 100 | 100 | 98 | 80 | 100 | 10 | 80 | 60 | 80 |
| | 0.50 | 10 | 90 | 60 | 0 | 40 | 60 | 60 | 40 | 98 | 98 | 100 | 100 | 100 | 98 | 95 | 100 | 80 | 98 | 90 | 100 |
| 54 | 0.25 | 20 | 60 | 80 | 10 | 70 | 10 | 60 | 50 | 0 | 80 | 100 | 40 | 100 | 100 | 90 | 90 | 95 | 98 | 40 | 100 |
| | 0.50 | 10 | 10 | 40 | 20 | 20 | 60 | 40 | 80 | 80 | 10 | 100 | 30 | 100 | 100 | 98 | 95 | 98 | 100 | 80 | 70 |
| | 1.00 | 30 | 30 | 50 | 40 | 30 | 10 | 30 | 90 | 100 | 80 | 100 | 80 | 100 | 100 | 90 | 95 | 95 | 100 | 90 | 90 |
| 56 | 1.00 | 0 | 0 | 0 | 0 | 0 | 40 | 0 | 0 | 100 | 10 | 95 | 0 | 0 | 100 | 50 | 98 | 0 | 0 | 0 | 0 |

TABLE VI-continued
POSTEMERGENCE HERBICIDE TESTING
PERCENT CROP INJURY OR WEED CONTROL

| Compound of Example No. | Application Rate lbs/A | A | U | G | J | D | P | V | L | B | C | F | Z | R | S | M | X | N | Y | Q | T |
|---|---|---|---|---|---|---|---|---|---|---|---|---|---|---|---|---|---|---|---|---|---|
| 57 | 2.00 | 0 | 0 | 0 | 0 | 0 | 0 | 0 | 0 | 0 | 10 | 90 | 0 | 10 | 10 | 80 | 98 | 90 | 0 | 0 | 30 |
|  | 4.00 | 0 | 0 | 0 | 0 | 10 | 10 | 10 | 20 | 20 | 20 | 90 | 70 | — | 40 | 80 | 98 | 90 | 20 | 0 | 80 |
|  | 0.50 | 50 | 40 | 80 | 30 | 10 | 50 | 90 | 70 | 100 | 100 | 100 | 80 | 50 | 90 | 100 | 90 | 90 | 90 | 90 | 80 |
|  | 1.00 | 60 | 80 | 80 | 30 | 40 | 70 | 98 | 80 | 100 | 100 | 100 | 80 | 70 | 100 | 100 | 90 | 90 | 100 | 100 | 100 |
|  | 2.00 | 80 | 80 | 80 | 50 | 40 | 98 | 100 | 90 | 100 | 100 | 100 | 90 | 100 | 100 | 100 | 98 | 90 | 100 | 100 | 100 |
| 58 | 0.125 | 10 | 30 | 50 | 50 | 50 | 40 | 50 | 80 | 95 | 80 | 100 | 50 | 100 | 70 | 80 | 98 | 30 | 98 | 70 | 98 |
|  | 0.25 | 20 | 60 | 50 | 70 | 40 | 50 | 50 | 95 | 98 | 100 | 100 | 70 | 95 | 100 | 90 | 100 | 50 | 100 | 95 | 100 |
|  | 0.50 | 30 | 98 | 80 | 98 | 50 | 60 | 70 | 100 | 100 | 80 | 98 | 70 | 100 | 100 | 95 | 100 | 80 | 100 | 98 | 100 |
| 59 | 0.125 | 30 | 10 | 70 | 70 | 40 | 30 | 20 | 60 | 80 | 50 | 100 | 60 | 100 | 70 | 60 | 100 | 40 | 80 | 30 | 100 |
|  | 0.25 | 40 | 50 | 80 | 80 | 60 | 60 | 40 | 50 | 98 | 98 | 100 | 50 | 100 | 100 | 80 | 100 | 60 | 100 | 70 | 98 |
|  | 0.50 | 40 | 50 | 90 | 95 | 70 | 70 | 80 | 80 | 100 | 98 | 100 | 100 | 100 | 100 | 95 | 100 | 80 | 100 | 98 | 100 |
| 60 | 0.125 | 10 | 40 | 80 | 70 | 30 | 10 | 20 | 40 | 60 | 40 | 100 | 70 | 100 | 60 | 80 | 98 | 40 | 90 | 10 | 60 |
|  | 0.25 | 20 | 50 | 80 | 80 | 50 | 60 | 50 | 60 | 95 | 90 | 100 | 70 | 100 | 80 | 95 | 100 | 60 | 98 | 90 | 100 |
|  | 0.50 | 20 | 50 | 90 | 80 | 70 | 70 | 60 | 90 | 80 | 100 | 100 | 98 | 100 | 100 | 80 | 98 | 60 | 100 | 50 | 100 |
| 61 | 0.125 | 20 | 40 | 70 | 95 | 40 | 40 | 50 | 30 | 98 | 50 | 100 | 90 | 100 | 95 | 95 | 100 | 70 | 95 | 50 | 100 |
|  | 0.25 | 30 | 60 | 80 | 90 | 60 | 50 | 20 | 90 | 100 | 100 | 100 | 90 | 100 | 95 | 95 | 98 | 80 | 98 | 70 | 100 |
|  | 0.50 | 40 | 80 | 95 | 98 | 60 | 70 | 70 | 90 | 80 | 50 | 100 | 100 | 100 | 95 | 95 | 100 | 80 | 98 | 70 | 100 |
| 62 | 0.125 | 60 | 80 | 90 | 80 | 60 | 70 | 50 | 60 | 98 | 100 | 100 | 90 | 98 | 60 | 60 | 100 | 30 | 100 | 70 | 100 |
|  | 0.25 | 95 | 80 | 90 | 60 | 70 | 80 | 60 | 98 | 95 | 80 | 100 | 100 | 95 | 98 | 90 | 100 | 80 | 100 | 70 | 100 |
|  | 0.50 | 70 | 90 | 80 | 90 | 70 | 70 | 0 | 20 | 100 | 98 | 100 | 100 | 100 | 99 | 95 | 100 | 80 | 100 | 90 | 100 |
| 63 | 0.25 | 0 | 0 | 60 | 0 | 0 | 10 | 0 | 20 | 0 | 10 | 100 | 50 | 95 | 0 | 70 | 100 | 30 | 0 | 0 | 80 |
|  | 0.50 | 0 | 10 | 70 | 0 | 10 | 20 | 0 | 30 | 20 | 10 | 100 | 50 | 100 | 10 | 40 | 100 | 70 | 0 | 20 | 95 |
|  | 1.00 | 0 | 20 | 80 | 0 | 20 | 20 | 0 | 80 | 20 | 20 | 100 | 70 | 100 | 10 | 60 | 100 | 70 | 20 | 30 | 95 |

The compound of Example 1 was further tested in field trials. First, the compound was formulated as an emlsifiable concentrate (EC) as described in the formulation section. Then the formulation was applied to various crops and weeds either sprayed over the surface (OTS), pre-plant incorporated (PPI), or surface applied (SA). After a certain number of days, the percent control was recorded and the results are found in Tables VII–XIII. (The type of formulation used is described in the formulation section.)

TABLE VII

PRE-PLANT INCORPORATION
PERCENT CONTROL-DAYS AFTER TREATMENT

| Compound of Example No. | Application Rate lb/A | Sorghum 23 | Sorghum 43 | Field Corn 23 | Field Corn 43 | Velvetleaf 23 | Velvetleaf 43 | Redroot Pigweed 43 | Jimsonweed 23 | Morningglory 23 | Morningglory 43 | Foxtail Millet 23 | Foxtail Millet 43 |
|---|---|---|---|---|---|---|---|---|---|---|---|---|---|
| 1 (1EC) | 0.125 | 0.0 | 0.0 | 0.0 | 0.0 | 0.0 | 0.0 | 30.0 | 0.0 | 0.0 | 16.7 | 26.7 | 16.7 |
| | 0.25 | 0.0 | 0.0 | 0.0 | 0.0 | 10.0 | 41.7 | 96.0 | 10.0 | 10.0 | 33.3 | 43.3 | 35.0 |
| | 0.5 | 35.0 | 6.7 | 0.0 | 0.0 | 85.0 | 85.0 | 100.0 | 96.7 | 86.7 | 76.7 | 81.7 | 83.3 |
| | 1.0 | 56.7 | 46.7 | 26.7 | 6.7 | 100.0 | 99.7 | 100.0 | 98.3 | 93.3 | 95.0 | 97.0 | 98.7 |

TABLE VIII

PRE-PLANT INCORPORATION
PERCENT CONTROL-DAYS AFTER TREATMENT

| Compound of Example No. | Application Rate lb/A | Sorghum 23 | Sorghum 43 | Field Corn 23 | Field Corn 43 | Velvetleaf 23 | Velvetleaf 43 | Redroot Pigweed 43 | Jimsonweed 23 | Morningglory 23 | Morningglory 43 | Foxtail Millet 23 | Foxtail Millet 43 |
|---|---|---|---|---|---|---|---|---|---|---|---|---|---|
| 1 (1EC) | 0.25 | 0.0 | 0.0 | 0.0 | 0.0 | 0.0 | 0.0 | 80.0 | 0.0 | 0.0 | 0.0 | 0.0 | 0.0 |
| | 0.5 | 3.3 | 0.0 | 6.7 | 0.0 | 0.0 | 16.7 | 91.7 | 0.0 | 0.0 | 13.3 | 60.0 | 71.7 |
| | 1.0 | 6.7 | 0.0 | 10.0 | 0.0 | 86.7 | 76.7 | 100.0 | 100.0 | 40.0 | 55.0 | 92.3 | 95.0 |
| | 2.0 | 70.0 | 53.3 | 26.7 | 11.7 | 91.7 | 94.3 | 99.3 | 100.0 | 93.3 | 96.7 | 99.7 | 100.0 |

TABLE IX

PRE-PLANT INCORPORATION
PERCENT CONTROL-DAYS AFTER TREATMENT

| Compound of Example No. | Application Rate lb/A | Soybean 23 | Soybean 41 | Upland Cotton 23 | Upland Cotton 41 | Velvetleaf 41 | Morninglory 23 | Morninglory 41 | Foxtail Millet 23 | Foxtail Millet 41 |
|---|---|---|---|---|---|---|---|---|---|---|
| 1 (1EC) | 0.125 | 6.7 | — | 6.7 | — | — | 20.0 | 0.0 | 23.3 | 0.0 |
| | 0.25 | 6.7 | 10.0 | 10.0 | 20.0 | 31.7 | 26.7 | 30.0 | 40.0 | 16.7 |
| | 0.5 | 36.7 | 45.0 | 33.3 | 57.5 | 100.0 | 96.7 | 100.0 | 78.3 | 61.7 |
| | 1.0 | 92.7 | 97.7 | 81.7 | 96.7 | 66.7 | 100.0 | 99.3 | 80.0 | 71.7 |

TABLE X

PREEMERGENT SURFACE APPLICATION
PERCENT CONTROL-DAYS AFTER TREATMENT

| Compound of Example No. | Application Rate lb/A | Soybean 23 | Soybean 40 | Upland Cotton 23 | Upland Cotton 40 | Velvetleaf 40 | Morninglory 23 | Morninglory 40 | Foxtail Millet 23 | Foxtail Millet 40 |
|---|---|---|---|---|---|---|---|---|---|---|
| 1 (1EC) | 0.25 | 3.3 | 5.0 | 6.7 | 20.0 | 30.0 | 0.0 | 30.0 | 26.7 | 23.3 |
| | 0.5 | 45.0 | 40.0 | 30.0 | 20.0 | 33.3 | 46.7 | 33.3 | 70.0 | 46.7 |
| | 1.0 | 76.7 | 93.3 | 70.0 | 74.7 | 92.7 | 66.0 | 63.3 | 93.7 | 96.0 |
| | 2.0 | 86.7 | 83.3 | 86.7 | 86.7 | 96.7 | 93.3 | 100.0 | 96.7 | 98.7 |

TABLE XI

POSTEMERGENT OVER THE SURFACE APPLICATION
PERCENT CONTROL-DAYS AFTER TREATMENT

| Compound of Example No. | Application Rate lb/A | Common Wheat 14 | Common Wheat 28 | Indian Mustard 14 | Indian Mustard 28 | Cheat 14 | Cheat 28 | Wild Buckwheat 14 | Wild Buckwheat 28 | Giant Foxtail 14 | Giant Foxtail 28 | Leaf Mustard 143 | Common Wheat 143 |
|---|---|---|---|---|---|---|---|---|---|---|---|---|---|
| 1 (1EC) | 0.062 | 0 | 0 | 36.7 | 60.0 | 0 | 0 | 16.7 | 6.7 | 0 | 0 | — | — |
| | 0.125 | 1.7 | 6.7 | 60.0 | 76.7 | 0 | 6.7 | 43.3 | 23.3 | 0 | 0 | 0 | 0 |
| | 0.25 | 10.0 | 11.7 | 96.0 | 98.3 | 13.3 | 1.7 | 76.7 | 76.7 | 53.3 | 26.7 | 0 | 0 |
| | 0.5 | 6.7 | 15.0 | 99.3 | 100.0 | 10.0 | 23.3 | 100.0 | 93.3 | 30.0 | 46.7 | 40.0 | 0 |

TABLE XII

POSTEMERGENT OVER THE SURFACE APPLICATION
PERCENT CONTROL-DAYS AFTER TREATMENT

| Compound of Example No. | Application Rate lb/A | Rice | | Velvetleaf | | Redroot Pigweed | | Barnyard Grass | | Morning-glory | |
|---|---|---|---|---|---|---|---|---|---|---|---|
| | | 7 | 14 | 7 | 14 | 7 | 14 | 7 | 14 | 7 | 14 |
| 1 (1EC) | 0.125 | 15.0 | 6.7 | 80.0 | 63.3 | 93.3 | 86.7 | 30.0 | 13.3 | 80.0 | 40.0 |
| | 0.25 | 20.0 | 10.0 | 96.7 | 86.7 | 100.0 | 98.3 | 43.3 | 20.0 | 86.7 | 53.3 |
| | 0.5 | 26.7 | 15.0 | 96.7 | 93.3 | 100.0 | 100.0 | 40.0 | 36.7 | 92.7 | 71.7 |
| | 1.0 | 30.0 | 25.0 | 100.0 | 100.0 | 100.0 | 100.0 | 63.3 | 66.7 | 95.0 | 90.0 |

TABLE XIII

POSTEMERGENT OVER THE SURFACE APPLICATION
PERCENT CONTROL-DAYS AFTER TREATMENT

| Compound of Example No. | Application Rate lb/A | Sorghum | | Field Corn | | Velvetleaf | | Redroot Pigweed | | Jimson-weed | Morning-glory | | Giant Foxtail | |
|---|---|---|---|---|---|---|---|---|---|---|---|---|---|---|
| | | 8 | 15 | 8 | 15 | 8 | 15 | 8 | 15 | 8 | 8 | 15 | 8 | 15 |
| 1 (1EC) | 0.062 | 3.3 | 0 | 6.7 | 0 | 63.3 | 56.7 | 83.3 | 73.3 | 100.0 | 76.7 | 46.7 | 16.7 | 10.0 |
| | 0.125 | 11.7 | 6.7 | 3.3 | 0 | 63.3 | 43.3 | 76.7 | 76.7 | 100.0 | 73.3 | 56.7 | 13.3 | 10.0 |
| | 0.25 | 8.3 | 0 | 6.7 | 0 | 90.0 | 85.0 | 90.0 | 92.7 | 100.0 | 80.0 | 70.0 | 16.7 | 3.3 |
| | 0.5 | 13.3 | 0 | 6.7 | 0 | 62.7 | 61.7 | 66.7 | 66.7 | 66.7 | 63.3 | 73.3 | 18.3 | 3.3 |

The amount of herbicidal pyridazinylimidazolidinones to be employed in the method of this invention is an amount, which is effective in controlling or inhibiting the growth of unwanted vegetation. Such herbicidal amount will depend upon a number of factors, including the method of application, formulation, soil texture, soil moisture content, the expected population of unwanted vegetation, degree of incorporation, the extent of growth control desired, and related factors. The rate of application normally will be from about 0.01 to about 10.0 pounds per acre, and preferably from about 0.25 to about 5.0 pounds per acre. These ranges are equivalent, respectively, to from about 0.011 to about 11.2 kilograms per hectare, and from about 0.28 to about 5.6 kilograms per hectare.

One of the preferred compounds of this invention, 3-[6-chloro-5-(1,1-dimethylethyl)-3-pyridazinyl]-4-hydroxy-1-methyl-2-imidazolidinone can be used in combination with atrazine or cyanazine to achieve improved or synergistic herbicidal activity. The combination is especially useful for control of weeds on corn including barnyardgrass, browntop panicum, seedling johnsongrass, and wild proso millet. Typically the ratio of imidazolidinone to atrazine or cyanazine is from 1:1 to 1:10.

The same imidazolidinone can also be used in combination with alachlor to diminish the risk of corn injury. The use of alachlor antidotes the injury on corn, which is caused by the imidazolidinone.

Terrestrial Herbicidal Formulations

The compounds of the present invention may also be formulated with a suitable agriculturally-acceptable carrier. These formulations will contain from about 12 to about 95.0 percent (%) by weight of the active ingredient, depending on the composition desired. Sprayable formulations are preferred, because of the rapidity and economy of application, and because the sprayed applications do not drift to untreated areas as would a dust, for example.

The most convenient formulations are in the form of concentrated compositions to be applied by spraying as water dispersions or emulsions containing in the range from about 0.1 to about 10% of the compounds. Water-dispersible or emulsifiable compositions may be either solids usually known as wettable powders, or liquids usually known as emulsifiable concentrates.

A typical wettable powder comprises mixture of a compound of the invention, an inert carrier, and surfactants. The concentration of the active compound is usually from about 25 to about 90% by weight. The inert carrier is usually chosen from among the attapulgite clays, the montmorillonite clays, the diatomaceous earths, or the purified silicates. Effective surfactants, comprising from about 0.5 to about 10% by weight of the wettable powder, are chosen from among the condensed napthalenesulfonates and the alkyl sulfates.

A typical emulsifiable concentrate comprises from about 1 to about 6 pounds of a compound of the invention per gallon of liquid, dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents, such as cyclohexanone and isophorone, may be included. Other organic solvents may also be used, including the terpenic solvents and kerosene. Suitable emulsifiers for emulsifiable concentrates are chosen from the alkylbenzenesulfonates, napthalenesulfonates, and nonionic surfactants, such as alkylphenol adducts of polyoxyethylene, and are used at similar percentages as for wettable powders.

The compounds of this invention may be preferably formulated as aqueous suspensions. A typical aqueous suspension formulation contains from about 12 to 75% by weight of the active ingredient, surfactants which are wetting and dispersing agents of the types used in wettable powder formulations and used at from 1 to 10%, about 5 to 10% of an antifreeze solution, such as ethylene or propylene glycol, and a bulking or thickening agent. These thickeners may be natural water soluble gums, clays with gelling properties, cellulose derivatives and the like, and are used from about 0.5 to 5% of the product. The remainder of the formulation is water. The product is prepared by grinding the slurry in a ball mill or sand mill to the desired particle size. Antifoam compounds, usually of the silicone type, may be added at 0.05 to 1% to control product foaming.

Solid, granular compositions are convenient for the application of compounds of this invention to the soil and will contain the active agent in an amount from about 0.1 to about 20% by weight. Granules comprise a compound of the invention dispersed on a granular inert carrier such as coarsely ground clay of from about 0.1 to about 3 millimeter (mm) particle size. The compound is most conveniently applied to the clay by dissolving it in an inexpensive solvent and applying the solution to the sized clay in an appropriate solids mixer.

The formulated compounds are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the compound, and to apply the amount uniformly to the plants to be treated.

The following detailed examples of formulations illustrate preferred aspects of the invention.

| Emulsifiable Concentrate (1EC) | |
|---|---|
| Ingredient | Percent by weight |
| Compound of Example 1 | 12.9 |
| Toximul H, a blend of emulsifiers, from Stepan Chemical Co. | 10.0 |
| Dowanol PM, propylene glycol monomethyl ether, from Dow Chemical Co. | 15.0 |
| Heavy Aromatic Naphtha | 62.1 |
| | 100.0 |

The above ingredients were blended together to form the concentrate.

| Aqueous Suspension (1 lb/gal) | |
|---|---|
| Ingredient | Percent by weight |
| Compound of Example 1 | 12.1 |
| Tergitol TMN-6, wetting agent, from Union Carbide | 10.0 |
| Polyfon H, a dispersant, from Westvaco Corp. | 0.5 |
| Propylene glycol | 10.0 |
| Xanthan gum, a thickening agent, from Kelco Co. | 1.0 |
| Antifoam C, a foam suppressant, from Dow Corning | 0.5 |
| Water | 65.9 |
| | 100.0 |

The soluble components and water are added to a tank equipped with a high shear mixer. The compound is added and mixed in. The mixture is circulated through a liquid grinding mill until the desired particle size is attained. Prehydrated xanthan gum is then added.

| Granule | |
|---|---|
| Ingredient | Percent by weight |
| Compound of Example 1 | 5.0 |
| Clay granule | 95.0 |
| | 100.0 |

The compound is substantially dissolved in acetone or similar solvent, and the organic solution is sprayed on to the clay, which is in the form of chips. The mixture is then thoroughly blended and dried.

| Wettable Powder | |
|---|---|
| Ingredient | Percent by weight |
| Compound of Example 1 | 75.0 |
| Fuller's earth | 19.0 |
| Sulfonated lignin | 3.5 |
| Sodium lauryl sulfate | 2.5 |
| | 100.0 |

The above ingredients are blended to uniformity and are ground in a hammer mill or air mill. The product is then reblended to a homogeneous free-flowing powder. The powder is dispersed in water and sprayed onto the weed-infested area.

Aquatic Herbicidal Method

A method of inhibiting the growth of unwanted aquatic vegetation is also provided by this invention which comprises contacting the vegetation or the water in which the vegetation is growing with a herbicidally-effective amount of a compound of the formula (I).

The aquatic herbicidal method is practiced by adding the active compound to the water containing the submerged, emergent, ditchbank, or floating aquatic plants or otherwise contacting the plants with the active compounds, for example, by applying the compounds to the sub-aqueous soil in which the aquatic plants are rooted. The compounds may also be mixed with surface-active dispersing agents to form concentrates to facilitate dispersion in water and to improve the wetting properties when used as sprays. If desired, the compounds may be mixed with a powdered solid carrier, such as bentonite, Fuller's earth, diatomaceous earth, or various mineral silicates, and clays together with surface-active wetting and dispersing agents, so that a wettable powder may be obtained which may be applied directly, or which may be mixed with water to make an aqueous dispersion for application in that form. These wettable powder formulations suitably contain from about 25 to about 85% by weight of the active ingredient. The compounds may be dissolved in an oil, such as a hydrocarbon or chlorinated hydrocarbon oil, and the oil solution of the compound dispersed in water with the aid of a surface-active emulsifying agent to give a sprayable aqueous emulsion. These surface-active emulsifying agents may be anionic, nonionic, or cationic surface-active agents. Such surface-active agents are well-known, and reference is made to Hoffman et al., U.S. Pat. No. 2,614,916, columns 2–4, for detailed examples of the same.

Further, the compounds can also be applied in an invert emulsion formulation. An invert emulsion formulation is prepared by first making a solution of the compound in heavy oils, such as diesel fuel, inverting oil, and the like, and combining the thus-obtained solution with water under high shear stirring. Densifying agents, such as powdered limestone or iron oxide may be needed to increase the density of the invert. The thick emulsion is placed in the water and sinks to the bottom of the lake, river, pond, or the like, and the aquatic herbicide is gradually released. The following is an example of an invert emulsion formulation, which can be prepared using the compound of Example 1.

| Invert Emulsion | |
|---|---|
| Ingredient | Amount |
| Compound of Example 1 | 12.5 g |
| Diesel fuel | 333 ml |
| Inverting oil* | 333 ml |

*Visko-Rhap Inverting Oil (Rhodia, Inc.)

Two-hundred fifty milliliters of this solution is combined with 3750 ml of water under high shear stirring to give a thick invert emulsion.

The compounds can also be applied as pellets, which are prepared from a mixture of about 5% of the active ingredient, about 87% balling clay, and about 10% water, all percentages being by weight. The mixture is then extruded through a pellet mill using a suitably sized die, e.g., about ⅛ inch (in.) diameter. The extruded pellets are about ⅛ in. by 1½ in., and are then dried to about 8% moisture content.

The method of controlling aquatic weeds provided by this invention is practiced by adding to the water containing the submerged, emergent, ditchbank, or floating plants, a herbicidal amount of one of the herein-disclosed compounds, such that a concentration of from about 0.01 to about 10 parts per million (ppm) of the active compound is attained.

The optimum concentration of active compound for any specific aquatic control problem varies with the temperature, the species to be controlled or inhibited, and the shape of the body of water to be treated. At higher water temperatures, less compound is generally required for a given degree of control or inhibition than is needed at lower temperatures. When used to control aquatic weeds, the compounds will usually be employed at concentrations of about 0.1 to about 10 ppm. In terms of pounds of compound per acre of water one foot deep, 0.1 to 10 ppm is equal to about 0.3 to about 30 pounds per acre of water one foot deep.

In considering the treatment of moving streams for the purpose of controlling vegetation fixed therein, special account must be taken of the fact that the compounds will pass over the area to be treated and that the concentration during the contact period is dependent upon the water flow rate, the rate of chemical addition, and the time period of addition.

We claim:

1. A compound of the formula (I):

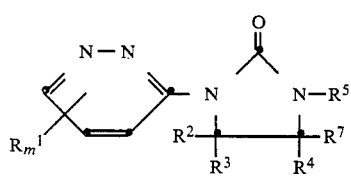

wherein
  each $R^1$ independently is halo, $C_1$–$C_8$ alkyl, $C_1$–$C_6$ alkoxy, $C_2$–$C_6$ alkenyl, $C_2$–$C_6$ alkynyl, $C_3$–$C_6$ cycloalkyl, ($C_1$–$C_3$ alkyl)$C_3$–$C_6$ cycloalkyl, ($C_1$–$C_3$ alkoxy)$C_1$–$C_8$ alkyl, adamantyl, phenyl, halo-substituted phenyl, (phenyl)$C_1$–$C_8$ alkyl, phenoxy, or (phenoxy)$C_1$–$C_8$ alkyl;
  $R^2$ is hydrogen, hydroxy, $C_1$–$C_6$ alkyl, $C_1$–$C_6$ alkoxy, or

$OCR^6$;

wherein $R^6$ is $C_1$–$C_{15}$ alkyl, $C_2$–$C_{15}$ alkenyl, $C_2$–$C_{15}$ alkynyl, $C_3$–$C_6$ cycloalkyl, di($C_1$–$C_6$ alkyl)amino, di(phenyl)amino, naphthyl, ($C_1$–$C_6$ alkyl)(phenyl)amino, or

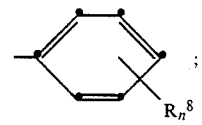

wherein each $R^8$ independently is halo, $C_1$–$C_6$ alkyl, $C_1$–$C_6$ alkoxy, halo($C_1$–$C_6$ alkyl), cyano, nitro, acetyl, phenyl, benzoyl, phenoxy, phenylthio, ($C_1$–$C_6$ alkyl)thio, $CF_3O$, $CF_3S$, or carboxy, optionally esterified with $C_1$–$C_6$ alkanol;
  $R^3$ is hydrogen or $C_1$–$C_6$ alkyl;
  $R^4$ is hydrogen, hydroxy, $C_1$–$C_6$ alkyl, or

$OCR^6$;

or $R^3$ and $R^4$ together form a double bond;
  $R^5$ is hydrogen, $C_1$–$C_6$ alkyl, $C_1$–$C_6$ alkoxy, or benzyl;
  $R^7$ is hydrogen or $C_1$–$C_6$ alkyl; and m and n are independently integers from 0 to 3.

2. The compound of claim 1 wherein
  each $R^1$ independently is halo or $C_1$–$C_6$ alkyl;
  $R^2$ is hydrogen, hydroxy, $C_1$–$C_4$ alkyl, $C_1$–$C_4$ alkoxy, or

$OCR^6$;

wherein $R^6$ is $C_1$–$C_6$ alkyl or

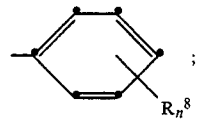

each $R^8$ independently is halo, methyl, or methoxy;
  $R^3$ is hydrogen or $C_1$–$C_3$ alkyl;
  $R^4$ is hydrogen, hydroxy, or $C_1$–$C_3$ alkyl;
  or $R^3$ and $R^4$ together form a double bond;
  $R^5$ is hydrogen or $C_1$–$C_3$ alkyl;
  $R^7$ is hydrogen; and
  m and n are independently 1 or 2.

3. The compound of claim 2 which is 3-[6-chloro-5-(1,1-dimethylbutyl)-3-pyridazinyl]-4-hydroxy-1-methyl-2-imidazolidinone.

4. The compound of claim 2 which is 3-[6-chloro-5-(1,1-dimethylethyl)-3-pyridazinyl]-1-methyl-4-(1-oxopropoxy)-2-imidazolidinone.

5. The compound of claim 2 which is 2-methylpropanoic acid, 3-[6-chloro-5-(1,1-dimethylethyl)-3-pyridazinyl]-1-methyl-2-oxo-4-imidazolidinyl ester.

6. The compound of claim 2 which is 2,2-dimethylpropanoic acid, 3-[6-chloro-5-(1,1-dimethylethyl)-3-pyridazinyl]-1-methyl-2-oxo-4-imidazolidinyl ester.

7. The compound of claim 2 wherein
each $R^1$ independently is chloro or 1,1-dimethylethyl;
$R^2$ is hydroxy or

wherein $R^6$ is

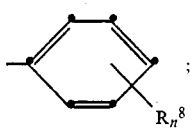

each $R^8$ independently is halo or methoxy;
$R^3$ and $R^4$ are hydrogen; and
$R^5$ is methyl.

8. The compound of claim 7 which is 3-[6-chloro-5-(1,1-dimethylethyl)-3-pyridazinyl]-4-hydroxy-1-methyl-2-imidazolidinone.

9. The compound of claim 7 which is 3-[6-(1,1-dimethylethyl)-3-pyridazinyl]-4-hydroxy-1-methyl-2-imidazolidinone.

10. The compound of claim 7 which is 3-[5-(1,1-dimethylethyl)-3-pyridazinyl]-4-hydroxy-1-methyl-2-imidazolidinone.

11. The compound of claim 7 which is 4-chlorobenzoic acid, 3-[6-chloro-5-(1,1-dimethylethyl)-3-pyridazinyl]-1-methyl-2-oxo-4-imidazolidinyl ester.

12. The compound of claim 7 which is 4-methoxybenzoic acid, 3-[6-chloro-5-(1,1-dimethylethyl)-3-pyridazinyl]-1-methyl-2-oxo-4-imidazolidinyl ester.

13. A method of inhibiting the growth of unwanted vegetation which comprises contacting the vegetation or the soil in which the vegetation is growing with a herbicidally-effective amount of a compound of claim 1.

14. The method of claim 13 wherein the unwanted vegetation is growing in soil planted with a corn crop.

15. The method of claim 14 wherein
each $R^1$ independently is halo or $C_1$–$C_6$ alkyl;
$R^2$ is hydrogen, hydroxy, $C_1$–$C_4$ alkyl, $C_1$–$C_4$ alkoxy or

wherein $R^6$ is $C_1$–$C_6$ alkyl or

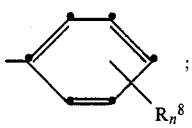

each $R^8$ independently is halo, methyl, or methoxy;
$R^3$ is hydrogen or $C_1$–$C_3$ alkyl;
$R^4$ is hydrogen, hydroxy, or $C_1$–$C_3$ alkyl;
or $R^3$ and $R^4$ together form a double bond;
$R^5$ is hydrogen or $C_1$–$C_3$ alkyl;

$R^7$ is hydrogen;
m and n are independently 1 or 2.

16. The method of claim 15 wherein the compound is 3-[6-chloro-5-(1,1-dimethylbutyl)-3-pyridazinyl]-4-hydroxy-1-methyl-2-imidazolidinone.

17. The method of claim 15 wherein the compound is 3-[6-chloro-5-(1,1-dimethylethyl)-3-pyridazinyl]-1-methyl-4-(1-oxopropoxy)-2-imidazolidinone.

18. The method of claim 15 wherein the compound is 2-methylpropanoic acid, 3-[6-chloro-5-(1,1-dimethylethyl)-3-pyridazinyl]-1-methyl-2-oxo-4-imidazolidinyl ester.

19. The method of claim 15 wherein the compound is 2,2-dimethylpropanoic acid, 3-[6-chloro-5-(1,1-dimethylethyl)-3-pyridazinyl]-1-methyl-2-oxo-4-imidazolidinyl ester.

20. The method of claim 15 wherein
each $R^1$ independently is chloro or 1,1-dimethylethyl;
$R^2$ is hydroxy or

wherein $R^6$ is

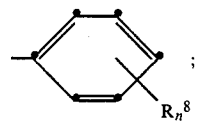

each $R^8$ independently is halo or methoxy;
$R^3$ and $R^4$ are hydrogen; and
$R^5$ is methyl.

21. The method of claim 20 wherein the compound is 3-[6-chloro-5-(1,1-dimethylethyl)-3-pyridazinyl]-4-hydroxy-1-methyl-2-imidazolidinone.

22. The method of claim 20 wherein the compound is 3-[6-(1,1-dimethylethyl)-3-pyridazinyl]-4-hydroxy-1-methyl-2-imidazolidinone.

23. The method of claim 20 wherein the compound is 3-[5-(1,1-dimethylethyl)-3-pyridazinyl]-4-hydroxy-1-methyl-2-imidazolidinone.

24. The method of claim 20 wherein the compound is 4-chlorobenzoic acid, 3-[6-chloro-5-(1,1-dimethylethyl)-3-pyridazinyl]-1-methyl-2-oxo-4-imidazolidinyl ester.

25. The method of claim 20 wherein the compound is 4-methoxybenzoic acid, 3-[6-chloro-5-(1,1-dimethylethyl)-3-pyridazinyl]-1-methyl-2-oxo-4-imidazolidinyl ester.

26. A formulation which comprises a compound of claim 1 and an agriculturally-acceptable carrier therefor.

27. The formulation of claim 26 wherein
each $R^1$ independently is halo or $C_1$–$C_6$ alkyl;
$R^2$ is hydrogen, hydroxy, $C_1$–$C_4$ alkyl, $C_1$–$C_4$ alkoxy or

wherein $R^6$ is $C_1$–$C_6$ alkyl or

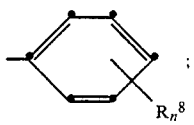

each R⁸ independently is halo, methyl or methoxy
R³ is hydrogen or $C_1$-$C_3$ alkyl;
R⁴ is hydrogen, hydroxy, or $C_1$-$C_3$ alkyl;
or R³ and R⁴ together form a double bond;
R⁵ is hydrogen or $C_1$-$C_3$ alkyl;
R⁷ is hydrogen; and
m and n are independently 1 or 2.

28. The formulation of claim 27 wherein the compound is 3-[6-chloro-5-(1,1-dimethylbutyl)-3-pyridazinyl]-4-hydroxy-1-methyl-2-imidazolidinone.

29. The formulation of claim 27 wherein the compound is 3-[6-chloro-5-(1,1-dimethylethyl)-3-pyridazinyl]-1-methyl-4-(1-oxopropoxy)-2-imidazolidinone.

30. The formulation of claim 27 wherein the compound is 2-methylpropanoic acid, 3-[6-chloro-5-(1,1-dimethylethyl)-3-pyridazinyl]-1-methyl-2-oxo-4-imidazolidinyl ester.

31. The formulation of claim 27 wherein the compound is 2,2-dimethylpropanoic acid, 3-[6-chloro-5-(1,1-dimethylethyl)-3-pyridazinyl]-1-methyl-2-oxo-4-imidazolidinyl ester.

32. The formulation of claim 27 wherein
each R¹ independently is chloro or 1,1-dimethylethyl;
R² is hydroxy or

OCR⁶;

wherein R⁶ is

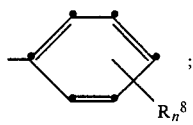

each R⁸ independently is halo or methoxy;
R³ and R⁴ are hydrogen; and
R⁵ is methyl.

33. The formation of claim 32 wherein the compound is 3-[6-chloro-5-(1,1-dimethylethyl)-3-pyridazinyl]-4-hydroxy-1-methyl-2-imidazolidinone.

34. The formulation of claim 32 wherein the compound is 3-[6-(1,1-dimethylethyl)-3-pyridazinyl]-4-hydroxy-1-methyl-2-imidazolidinone.

35. The formulation of claim 32 wherein the compound is 3-[5-(1,1-dimethylethyl)-3-pyridazinyl]-4-hydroxy-1-methyl-2-imidazolidinone.

36. The formulation of claim 32 wherein the compound is 4-chlorobenzoic acid, 3-[6-chloro-5-(1,1-dimethylethyl)-3-pyridazinyl]-1-methyl-2-oxo-4-imidazolidinyl ester.

37. The formulation of claim 32 wherein the compound is 4-methoxybenzoic acid, 3-[6-chloro-5-(1,1-dimethylethyl)-3-pyridazinyl]-1-methyl-2-oxo-4-imidazolidinyl ester.

38. A method of inhibiting the growth of unwanted aquatic vegetation which comprises contacting the vegetation or the water in which the vegetation is growing with a herbicidally-effective amount of a compound of claim 1.

39. The method of claim 38 wherein the compound is 3-[6-chloro-5-(1,1-dimethylethyl)-3-pyridazinyl]-4-hydroxy-1-methyl-2-imidazolidinone.

* * * * *